United States Patent
Azhir

(10) Patent No.: US 10,143,687 B2
(45) Date of Patent: *Dec. 4, 2018

(54) COMPOSITIONS AND METHODS FOR TREATMENT RELATED TO FALL AND FALL FREQUENCY IN NEURODEGENERATIVE DISEASES

(71) Applicant: Neurocea, LLC, Los Altos, CA (US)

(72) Inventor: Arasteh Ari Azhir, Los Altos, CA (US)

(73) Assignee: NEUROCEA, LLC, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,960

(22) Filed: Apr. 11, 2017

(65) Prior Publication Data

US 2018/0125837 A1    May 10, 2018

Related U.S. Application Data

(60) Provisional application No. 62/320,871, filed on Apr. 11, 2016.

(51) Int. Cl.
*A61K 31/465*    (2006.01)
*A61K 45/06*    (2006.01)

(52) U.S. Cl.
CPC .......... *A61K 31/465* (2013.01); *A61K 45/06* (2013.01); *A61K 2300/00* (2013.01)

(58) Field of Classification Search
CPC ... A61K 31/465; A61K 45/06; A61K 2300/00
See application file for complete search history.

(56) References Cited

U.S. PATENT DOCUMENTS

| | | |
|---|---|---|
| 4,321,387 A | 3/1982 | Chavdarian et al. |
| 4,327,725 A | 5/1982 | Cortese et al. |
| 4,332,945 A | 6/1982 | Edwards, III |
| 4,442,292 A | 4/1984 | Edwards, III |
| 4,452,984 A | 6/1984 | Edwards, III |
| 4,590,278 A | 5/1986 | Edwards, III |
| 5,232,704 A | 8/1993 | Franz et al. |
| 5,965,571 A | 10/1999 | Hutchinson |
| 5,972,389 A | 10/1999 | Shell et al. |
| 6,024,981 A | 2/2000 | Khankari et al. |
| 6,120,803 A | 9/2000 | Wong et al. |
| 6,221,392 B1 | 4/2001 | Khankari et al. |
| 6,238,689 B1 | 5/2001 | Rhodes et al. |
| 6,365,182 B1 | 4/2002 | Khankari et al. |
| 6,368,625 B1 | 4/2002 | Siebert et al. |
| 6,723,340 B2 | 4/2004 | Gusler et al. |
| 6,911,475 B1 | 6/2005 | Cesaro et al. |
| 7,229,641 B2 | 6/2007 | Cherukuri |
| 7,282,217 B1 | 10/2007 | Grimshaw et al. |
| 7,384,653 B2 | 6/2008 | Wright et al. |
| 7,718,677 B2 | 5/2010 | Quik et al. |
| 8,192,756 B2 | 6/2012 | Berner et al. |
| 2005/0021092 A1 | 1/2005 | Yun et al. |
| 2006/0053046 A1 | 3/2006 | Bonnstetter et al. |
| 2008/0260825 A1 | 10/2008 | Quik et al. |
| 2011/0268809 A1 | 11/2011 | Brinkley et al. |
| 2013/0017259 A1* | 1/2013 | Azhir .................. A61K 31/465 424/461 |
| 2016/0220553 A1 | 8/2016 | Azhir |
| 2016/0235732 A1 | 8/2016 | Quik |

FOREIGN PATENT DOCUMENTS

| | | |
|---|---|---|
| WO | WO-9712605 A1 | 4/1997 |
| WO | WO-9855107 A1 | 12/1998 |
| WO | WO-03039518 A1 | 5/2003 |
| WO | WO-03061656 A1 | 7/2003 |
| WO | WO-2009003147 A1 | 12/2008 |

OTHER PUBLICATIONS

Abraham Lieberman, Narayanan Krishnamurthi, Rohit Dhall, Naomi Salins, Pan D and Aman Deep, Comparison of Parkinson Disease Patients Who Fell Once with Patients Who Fell More than Once (Recurrent Fallers), J. Alzheimers Dis Parkinsonism, 4(2) (Year: 2014).*
Alfonso Fasano et al., Falls in Parkinson's Disease: A Complex and Evolving Picture, Movement Disorders, vol. 32, No. 11, 2017 (Year: 2017).*
Abood, et al. Structure-activity studies of carbamate and other esters: agonists and antagonists to nicotine. Pharmacol Biochem Behav. Jun. 1988;30(2):403-8.
Meshul, Charles K. et al. Nicotine Affects Striatal Glutamatergic Function in 6-OHDA Lesioned Rats. Advances in Behavioral Biology, 54 (Basal Ganglia VI), 589-598, 2003.
Chung, K.A. et al. Effects of a central cholinesterase inhibitor on reducing falls in Parkinson disease. Neurology. Oct. 5, 2010;75(14):1263-9. Epub Sep. 1, 2010.
Co-pending U.S. Appl. No. 15/853,151, filed Dec. 22, 2017.
Damaj, et al. Antinociceptive responses to nicotinic acetylcholine receptor ligands after systemic and intrathecal administration in mice. Journal Pharmacol. Exp Ther. Mar. 1998;284(3):1058-65.
International Application No. PCT/US17/68271 International Search Report and Written Opinion dated May 1, 2018.
Ishikawa, A. et al. Effects of smoking in patients with early-onset Parkinson's disease. Journal of Neurological Sciences, 117(1-2): 28-32 (Jul. 1, 1993).
Lieberman. Pharmaceutical Dosage Forms. vol. 1, 2nd ed.. New York Marcel Dekker, Inc. 1989; 195-246.
Lieberman. Pharmaceutical Dosage Forms. vol. 1, 2nd ed.. New York Marcel Dekker, Inc. 1989; 266-271.

(Continued)

*Primary Examiner* — Sarah Pihonak
*Assistant Examiner* — Jason Deck
(74) *Attorney, Agent, or Firm* — Wilson Sonsini Goodrich & Rosati

(57) ABSTRACT

The present disclosure provides methods and compositions for treating fall-related symptoms in patients with neurodegenerative diseases such as Parkinson's disease or Parkinson-related diseases. In some embodiments, the disclosure utilizes nicotine or salt thereof in combination of dopaminergic agent treatments for reducing fall-related symptoms such as reducing frequency of fall, reducing injuries related to fall, reducing severity of injuries related to fall, improving posture stability, improving locomotion ability, improving balance and gait. In some embodiments, the methods predict fall frequency and tendency of recurrent falls in patients with Parkinson's disease, in particular, patients with typical Parkinson's disease.

20 Claims, 15 Drawing Sheets

(56) References Cited

OTHER PUBLICATIONS

Quik, et al. Nicotine and Parkinson's disease: implications for therapy. Mov Disord. 2008; 23(12):1641-52.
Quik et al. Nicotine and Nicotinic Receptor. NeuroToxicology 23; 581-594 (2002).
Quik, Maryka Smoking, nicotine and Parkinson's disease, Trends in Neurosciences 27(9); 561-568 (Sep. 2004).
Villafane, Gabriel et al. Long-Term Nicotine Administration Can Improve Parkinson's Disease Report on a Case After Three Years of Treatment. Revista Neurologica Argentina, 27(2); 95-97 (2002).
U.S. Appl. No. 15/853,151 Non-Final Office Action dated Aug. 30, 2018.

* cited by examiner

COMPOSITIONS AND METHODS FOR TREATMENT RELATED TO FALL AND FALL FREQUENCY IN NEURODEGENERATIVE DISEASES

CROSS-REFERENCE

This application claims the benefit of U.S. Provisional Application No. 62/320,871 filed on Apr. 11, 2016, which is incorporated herein by reference in its entirety.

BACKGROUND

Parkinson's disease (also known as Parkinson disease, Parkinson's, idiopathic parkinsonism, primary parkinsonism, PD, or paralysis agitans) is a degenerative disorder of the central nervous system. It results from the death of dopamine-containing cells in the substantia nigra, a region of the midbrain; the cause of cell-death is unknown. Early in the course of the disease, the most obvious symptoms are movement- and balance-related, including shaking, rigidity, slowness of movement and difficulty with walking and gait. The main motor symptoms are collectively called parkinsonism, or a "parkinsonian syndrome". The pathology of the disease is characterized by the accumulation of a protein called alpha-synuclein into inclusions called Lewy bodies in neurons, and from insufficient formation and activity of dopamine produced in certain neurons of parts of the midbrain.

INCORPORATION BY REFERENCE

All publications and patent applications mentioned in this specification are herein incorporated by reference to the same extent as if each individual publication or patent application was specifically and individually indicated to be incorporated by reference.

BRIEF SUMMARY

Described herein are methods of treating fall-related symptoms in a subject with neurodegenerative disease, the methods may comprise administering to the subject a dosage form comprising nicotine or salt thereof. The fall-related symptoms may comprise fall frequency. A subject treated with the dosage form comprising nicotine may have a reduced fall frequency. The fall-related symptoms can comprise frequency of injuries related to fall. A subject treated with the dosage form comprising nicotine can have reduced frequency of injuries related to fall. The fall-related symptoms may comprise severity of fall with injuries. A subject treated with the dosage form comprising nicotine may have reduced severity of fall with injuries. The subject may have recurrent falls. The subject may have fallen at least once in past year. The improvement of symptoms can comprise utilizing one or more of evaluation tests selected from the group consisting of: Unified Parkinson's Disease Rating Scale (UPDRS), Barrow Neurological Institute (BNI) Falls Evaluation, Hoehn & Yahr Staging System, Romberg test, turning test, standing on one leg, tandem gait, step length and velocity. The evaluation utilizing the Unified Parkinson's Disease Rating Scale (UPDRS) can be selected from the group consisting of: Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS). The improvement of symptoms may comprise evaluation utilizing Reason for Fall from the Barrow Neurological Institute (BNI) Falls Evaluation. The improvement of symptoms can comprise evaluation utilizing Severity of Fall from the Barrow Neurological Institute (BNI) Falls Evaluation.

Described herein are methods of treating posture instability, static balance, locomotor disability and gait in a subject with neurodegenerative disease, the methods can comprise administering to the subject a dosage form comprising nicotine or a salt thereof. A subject treated with the dosage form comprising nicotine can have improved posture stability. A subject treated with the dosage form comprising nicotine can have improved static balance. A subject treated with the dosage form comprising nicotine can have improved locomotor ability. A subject treated with the dosage form comprising nicotine can have improved gait. Improvement of symptoms may comprise utilizing one or more of evaluation tests selected from the group consisting of: Unified Parkinson's Disease Rating Scale (UPDRS), BNI Falls Evaluation, Hoehn & Yahr Staging System, Romberg test, turning test, standing on one leg, tandem gait, step length and velocity. The evaluation utilizing the Unified Parkinson's Disease Rating Scale (UPDRS) can be selected from the group consisting of: Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS). The subject may have Parkinson's disease. The subject may have typical Parkinson's disease. The subject may have Parkinson's disease for at least five years. The subject may have Parkinson's disease for at least four years. The subject may have Parkinson's disease for at least three years. The subject may have Parkinson's disease for at least two years. The subject may have Parkinson's disease for at least one year. The subject may have dopaminergic agent treatment. The dopaminergic agent may be levodopa, carbidopa, dopamine agonist, amantadine, monoamine oxidase B inhibitor, or combination thereof. The subject may be evaluated in: an "off" period, wherein the subject may be about 16 hours off dopaminergic agent treatment; The "off" period may about 2, 4, 6, 8, 10, 12, 14, 16, 18, or 24 hours. During the "on" period the subject may be about 1 hour after usual morning dose of dopaminergic agent treatment; wherein the dopaminergic treatment may be levodopa, carbidopa, dopamine agonist, amantadine, monoamine oxidase B inhibitor, or combination thereof. The "on" period may about 0.5, 1, 2, 4, 6, 8, 10, 12, 14, 16, 18, or 24 hours. The "off" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "off" period may be at most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The "on" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "on" period may be at most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The subject can have Montreal Cognitive Assessment (MOCA) score of at least 26. The subject can have Montreal Cognitive Assessment (MOCA) score of at least or about 20, 25, 30, 35, 40, or more than 40. The subject can be excluded with disorders selected in the group consisting of: atypical Parkinson, Progressive Supranuclear Palsy (PSP), Multiple System Atrophy (MSA), Primary Freezing of Gait (PFG), Corticobasiler Degeneration, dementia with Montreal Cognitive Assessment (MOCA) score of less than 21, legally blind, orthopedic problems in hips or knees, hips or knees replacements, orthostatic hypotension, schizophrenia, schizo-affective disorder, bipolar disorder, hallucinations, psychoses, delusions, deep brain stimulation (DBS) intervention, history of recent stroke, and history of myocardial infarction. The dosage form may comprise a nicotinic receptor agonist. The dosage form may comprise at least 1 mg to 6 mg of nicotine or salt thereof for a period of 6 months, wherein the dosage form may be escalated upward at treatment intervals. The dosage form may comprise at least or about 1, 2, 3, 4, 5, 6, 7, 8, 9, 10, 11, 12, or more than 12 mg of nicotine or salt thereof. The dosage form may comprise about 2, 4, 6, 12, 18, or 24 mg of nicotine or salt thereof. The period may be at least or about 1, 2, 3, 4, 5, 6, 7, 8, 9, 10, 11, 12, or more than 12 months. The dosage form may comprise nicotine or salt thereof may be escalated upward at two weeks treatment intervals. The dosage form may comprise nicotine or salt thereof may be escalated upward at 1, 2, 3, 4, 5, 6, 7, 8, 9, 10, 11, 12, or more than 12 weeks treatment intervals. The dosage form may comprise nicotine or salt thereof comprises: at least 1 mg every 6 hours; at least 2 mg every 6 hours; at least 4 mg every 6 hours; at least 6 mg every 6 hours; wherein the dose may be escalated at two weeks treatment intervals; and wherein the dose may be maintained at 6 mg every 6 hours until completion of the treatment period of 6 months. The nicotine or salt thereof can be administered in an amount less than 24 mg in a period of 24 hours. The nicotine or salt thereof can be administered in an amount of at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 mg. The nicotine or salt thereof may be administered in an amount of about 2, 4, 6, 8, 10, 12, 18, or 24 mg. The nicotine or salt thereof can be administered in a period of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 hours. The nicotine or salt thereof can be administered at least 4 times in a period of 24 hours. The nicotine or salt thereof can be administered at least 1, 2, 3, 4, 5, 6, 7, 8, 9, 10, 11, 12, 13, 14, 15, 16, 17, 18, 19, 20, or more than 20 times. The nicotine or salt thereof can be administered about every 6 hours in a period of 24 hours. The nicotine or salt thereof can be administered about every 1, 2, 3, 4, 5, 6, 7, 8, 9, 10, 11, 12, 13, 14, 15, 16, 17, 18, 19, 20, 21, 22, or 23 hours in a period of 24 hours. The therapeutic effectiveness of the administration can evaluated regularly for a period of at least 2 to 14 months. The therapeutic effectiveness of the administration can be evaluated regularly for a period of at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 months. The therapeutic effectiveness of the administration can be evaluated regularly for a period of at least 6 months. The evaluation can be performed every 2 months. The evaluation can be performed every 1, 2, 3, 4, 5, 6, 7, 8, 9, 10, 11, 12, or more than 12 months. The dosage form may be formulated for oral, intravenous, intraarterial, parenteral, buccal, topical, transdermal, rectal, intramuscular, subcutaneous, intraosseous, transmucosal, or intraperitoneal administration. The dosage form may be formulated for oral administration. The dosage form may be formulated as a unit dosage. The composition may be formulated as a unit dosage in liquid, gel, semi-liquid, semi-solid, or solid form. The dosage form may be formulated in a tablet. The dosage form may be formulated in a capsule. The unit dosage may be formulated as a food. The unit dosage may be formulated as a beverage. The unit dosage may be formulated as a dietary supplement. The administration of said dosage form may result in a pharmacokinetic profile having plasma nicotine levels below about 7.5 ng/ml at a time point about 120 minutes after administration of said dosage form. The administration of said dosage form may result in a pharmacokinetic profile having plasma nicotine levels below about 7.5 ng/ml at a time point about 180 minutes after administration of said dosage form. The pharmacokinetic profile may have plasma nicotine levels below about 5 ng/ml at about 180 minutes after administration. The pharmacokinetic profile may have plasma nicotine levels below about 5 ng/ml at about 120 minutes after administration. The pharmacokinetic profile may have plasma nicotine levels above about 5 ng/ml at about 45 to 90 minutes after administration. The pharmacokinetic profile may have plasma nicotine levels above about 15 ng/ml at about 60 minutes after administration.

Described herein are multiparticulate formulations, wherein the formulation can deliver an immediate-release bolus of nicotine at time zero, and a second immediate-release bolus of nicotine approximately six hours after ingestion. The formulation can deliver an immediate-release bolus of nicotine at time zero, 1, 2, 3, 4, 5, 6, 7, 8, 9, or 10. The formulation can deliver a second immediate-release bolus of nicotine approximately 4, 5, 6, 7, 8, 9, 10, 11, 12, 13, 14, 15, 16, 17, 18, 19, 20 or more than 20 hours after ingestion. The multiparticulate formulation may comprise: a first population of particles coated with a drug layer comprising nicotine; and a second population of particles coated with the drug layer comprising nicotine, further coated with a delayed release coating. The first population of particles may be further coated with an immediate release coating. The immediate release coating may be an Opadry coating. The delayed release coating may comprise a polymer, a plasticizer, and an antitack agent. The polymer, the plasticizer, and the antitack agent may be present in a ratio of 6:1:3. The polymer may be Eudragit RS and/or Eudragit RL. The plasticizer may be triethyl citrate. The antitack agent may be talc. The administration of said multiparticulate formulation may result in a pharmacokinetic profile having plasma nicotine levels below about 7.5 ng/ml at a time point about 120 minutes after administration of said dosage form. The administration of said multiparticulate formulation may result in a pharmacokinetic profile having plasma nicotine levels below about 7.5 ng/ml at a time point about 180 minutes after administration of said dosage form. The pharmacokinetic profile may have plasma nicotine levels below about 5 ng/ml at about 180 minutes after administration. The pharmacokinetic profile may have plasma nicotine levels below about 5 ng/ml at about 120 minutes after administration. The pharmacokinetic profile may have plasma nicotine levels above about 5 ng/ml at about 45 to 90 minutes after administration. The pharmacokinetic profile may have plasma nicotine levels above about 15 ng/ml at about 60 minutes after administration.

Described herein are methods of treating cognitive-related symptoms in a subject with neurodegenerative disease, the methods can comprise administering to the subject a dosage form comprising nicotine or salt thereof. The cognitive-related symptoms can be impairments in visuospatial memory, executive functioning, short term memory, working memory, long-term memory, attention, language, abstraction, or spatial orientation. The improvement of symptoms can comprise utilizing one or more of evaluation tests Montreal Cognitive Assessment. The subject may have Parkinson's disease. The subject may have typical Parkinson's disease. The subject may have subject Parkinson's disease for at least five years. The subject may have subject Parkinson's disease for at least four years. The subject may have subject Parkinson's disease for at least three years. The subject may have subject Parkinson's disease for at least two years. The subject may have subject Parkinson's disease for at least one years. The subject may have dopaminergic agent treatment. The dopaminergic agent may be levodopa, carbidopa, dopamine agonist, amantadine, monoamine oxidase B inhibitor, or combination thereof. The subject may be evaluated in: an "off" period, wherein the subject can be about 16 hours off dopaminergic agent treatment; an "on" period, wherein the subject can be about 1 hour after usual morning dose of dopaminergic agent treatment; wherein the dopaminergic treatment can be levodopa, carbidopa, dopamine agonist, amantadine, monoamine oxidase B inhibitor, or combination thereof. The "off" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "off" period may be most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The "on" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "on" period may be most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The subject can have Montreal Cognitive Assessment (MOCA) score of at least 26. The dosage form may comprise a nicotinic receptor agonist. The dosage form may comprise at least 1 mg to 6 mg of nicotine or salt thereof for a period of 6 months, wherein the dosage form can be escalated upward at treatment intervals. The dosage form may comprise at least or about 1, 2, 3, 4, 5, 6, 7, 8, 9, 10, 11, 12, or more than 12 mg of nicotine or salt thereof. The period may be at least or about 1, 2, 3, 4, 5, 6, 7, 8, 9, 10, 11, 12, or more than 12 months. The dosage form may comprise nicotine or salt thereof can be escalated upward at two weeks treatment intervals. The dosage form may comprise nicotine or salt thereof can be escalated upward at 1, 2, 3, 4, 5, 6, 7, 8, 9, 10, 11, 12, or more than 12 weeks treatment intervals. The dosage form may comprise nicotine or salt thereof comprises: at least 1 mg every 6 hours; at least 2 mg every 6 hours; at least 4 mg every 6 hours; at least 6 mg every 6 hours; wherein the dose can be escalated at two weeks treatment intervals; and wherein the dose can be maintained at 6 mg every 6 hours until completion of the treatment period of 6 months. The dosage form may comprise nicotine or salt thereof of at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 mg. The dosage form may comprise nicotine or salt thereof administered in a period of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 hours. The dosage form may be escalated at 1, 2, 3, 4, 5, 6, 7, 8, 9, 10, 11, 12, or more than 12 weeks treatment intervals. The dose may be maintained at least or about at 1, 2, 3, 4, 5, 6, 7, 8, 9, 10, 11, 12 or more than 12 mg. The dose may be maintained every 1, 2, 3, 4, 5, 6, 7, 8, 9, 10, 11, 12, 13, 14, 15, 16, 17, 18, 19, 20, 21, 22, 23, 24, or more 24 hours. The treatment period may be at least or about 1, 2, 3, 4, 5, 6, 7, 8, 9, 10, 11, 12, 13, 14, 15, 16, 17, 18, 19, 20, 21, 22, 23, 24, or more than 24 months. until completion of the treatment period of 6 months. The nicotine or salt thereof may be administered in an amount less than 24 mg in a period of 24 hours. The nicotine or salt thereof may be administered at least 4 times in a period of 24 hours. The nicotine or salt thereof may be administered about every 6 hours in a period of 24 hours. The nicotine or salt thereof can be administered at least 1, 2, 3, 4, 5, 6, 7, 8, 9, 10, 11, 12, 13, 14, 15, 16, 17, 18, 19, 20, or more than 20 times. The nicotine or salt thereof can be administered about every 6 hours in a period of 24 hours. The nicotine or salt thereof can be administered about every 1, 2, 3, 4, 5, 6, 7, 8, 9, 10, 11, 12, 13, 14, 15, 16, 17, 18, 19, 20, 21, 22, or 23 hours in a period of 24 hours. The therapeutic effectiveness of the administration can evaluated regularly for a period of at least 2 to 14 months. The therapeutic effectiveness of the administration can be evaluated regularly for a period of at least 6 months. The therapeutic effectiveness of the administration can be evaluated regularly for a period of at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 months. The evaluation can be performed every 2 months. The evaluation can be performed every 1, 2, 3, 4, 5, 6, 7, 8, 9, 10, 11, 12, or more than 12 months. The said dosage form can be formulated for oral, intravenous, intraarterial, parenteral, buccal, topical, transdermal, rectal, intramuscular, subcutaneous, intraosseous, transmucosal, or intraperitoneal administration. The said dosage form can be formulated for oral administration. The said dosage form can be formulated as a unit dosage. The said dosage form can be formulated as a unit dosage in liquid, gel, semi-liquid, semi-solid, or solid form. The said dosage form can be formulated in a tablet. The said dosage form can be formulated in a capsule. The said dosage form can be formulated as a food. The said dosage form can be formulated as a beverage. The said dosage form can be formulated as a dietary supplement. The said dosage form can be formulated as a dietary supplement. The administration of said dosage form can result in a pharmacokinetic profile having plasma nicotine levels below about 7.5 ng/ml at a time point about 120 minutes after administration of said dosage form. The said dosage form can be formulated as a dietary supplement. The administration of said dosage form can result in a pharmacokinetic profile having plasma nicotine levels below about 7.5 ng/ml at a time point about 180 minutes after administration of said dosage form. The pharmacokinetic profile may have plasma nicotine levels below about 5 ng/ml at about 180 minutes after administration. The pharmacokinetic profile may have nicotine levels below about 5 ng/ml at about 120 minutes after administration. The pharmacokinetic profile may have plasma nicotine levels above about 5 ng/ml at about 45 to 90 minutes after administration. The pharmacokinetic profile may have plasma nicotine levels above about 15 ng/ml at about 60 minutes after administration. The dosage form may be the multiparticulate formulation. The dosage form may provide a 1 ng/mL to 20 ng/ml plasma concentration of nicotine about 2 h after administration of a dopaminergic agent. The dosage form may provide a 1, 2, 3, 4, 5, 6, 7, 8, 9, 10, 11, 12, 13, 14, 15, 16, 17, 18, 19, 20, 25, 30, 35, or more than 35 ng/mL plasma concentration of nicotine about 1, 2, 3, 4, 5, 6, 7, 8, 9, 10, 11, 12 or more than 12 hours after administration of a dopaminergic agent. The neurodegenerative disease may be selected from the group consisting of: Parkinson's disease, schizophrenia, mild cognitive impairment, Alzheimer's Disease, vascular cognitive impairment, Subcortical Ischaemic Vascular Dementia, Frontotemporal Mild Cognitive Impairment, and Frontotemporal Dementia.

Described herein are methods of administration of a nicotine dosage form, wherein said administration can result in a pharmacokinetic profile having plasma nicotine levels below about 7.5 ng/ml at a time point about 120 minutes after administration of said dosage form. The administration of said dosage form can result in a pharmacokinetic profile having plasma nicotine levels below about 7.5 ng/ml at a time point about 180 minutes after administration of said dosage form. The pharmacokinetic profile can have plasma nicotine levels below about 5 ng/ml at about 180 minutes after administration. The pharmacokinetic profile can have plasma nicotine levels below about 5 ng/ml at about 120 minutes after administration. The pharmacokinetic profile can have plasma nicotine levels above about 5 ng/ml at about 45 to 90 minutes after administration. The pharmacokinetic profile can have plasma nicotine levels above about 15 ng/ml at about 60 minutes after administration.

Described herein are formulations comprising nicotine or a salt thereof, wherein administration can result in a pharmacokinetic profile having plasma nicotine levels below about 7.5 ng/ml at a time point about 120 minutes after administration of said dosage form. The administration of said dosage form can result in a pharmacokinetic profile having plasma nicotine levels below about 7.5 ng/ml at a time point about 180 minutes after administration of said dosage form. The pharmacokinetic profile can have plasma nicotine levels below about 5 ng/ml at about 180 minutes after administration. The pharmacokinetic profile can have has plasma nicotine levels below about 5 ng/ml at about 120 minutes after administration. The pharmacokinetic profile can have plasma nicotine levels above about 5 ng/ml at about 45 to 90 minutes after administration. The pharmacokinetic profile can have plasma nicotine levels above about 15 ng/ml at about 60 minutes after administration.

Described herein are methods of treating fall-related symptoms in a subject with neurodegenerative disease, the methods can comprise administering to the subject a dosage form comprising a nicotinic acetylcholine receptor (nAChR) agonist. The nAChR agonist may be specific for the α7, β2, or α7 and β2 subunit of the nAChR. The nAChR agonist may be a full agonist. The nAChR agonist may be selected from Varenicline, A-85380, sazetidine, TC-2696, TI-10165, TC-8831, TC-10600, ABT-089, ABT-894, AZD1446, ABT-107, AQW051, ABT-894 and ABT-107, 3-Bromocytisine, Acetylcholine, Cytisine, Epibatidine, A-84,543, A-366,833, ABT-418, Altinicline, Dianicline, Ispronicline, Pozanicline, Rivanicline, Tebanicline, TC-1827, Sazetidine A, N-(3-pyridinyl)-bridged bicyclic diamines, (+)-N-(1-azabicyclo [2.2.2]oct-3-yl)benzo[b]furan-2-carboxamide, A-582941, AR-R17779, Amyloid beta, TC-1698, TC-5619, EVP-6124, GTS-21, PHA-543,613, PNU-282,987, PHA-709829, SSR-180,711, Tropisetron, WAY-317,538, Anabasine, and ICH-3. The nAChR agonist may be selected from ABT-894, ABT-107, TC-8831, ABT-089, AZD1446, and AQW051. The nAChR agonist may be selected from ABT-894 and ABT-107. The fall-related symptoms may comprise fall frequency. A subject treated with the dosage form comprising the nAChR agonist may have a reduced fall frequency. The fall-related symptoms may comprise frequency of injuries related to fall. A subject treated with the dosage form comprising the nAChR agonist may have reduced frequency of injuries related to fall. The fall-related symptoms may comprise severity of fall with injuries. A subject treated with the dosage form comprising the nAChR agonist may have reduced severity of fall with injuries. The subject may have recurrent falls. The subject may have fallen at least once in past year. The improvement of symptoms may comprise utilizing one or more of evaluation tests selected from the group consisting of: Unified Parkinson's Disease Rating Scale (UPDRS), Barrow Neurological Institute (BNI) Falls Evaluation, Hoehn & Yahr Staging System, Romberg test, turning test, standing on one leg, tandem gait, step length and velocity. The evaluation utilizing the Unified Parkinson's Disease Rating Scale (UPDRS) may be selected from the group consisting of: Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS). The improvement of symptoms may comprise evaluation utilizing Reason for Fall from the Barrow Neurological Institute (BNI) Falls Evaluation. The improvement of symptoms may comprise evaluation utilizing Severity of Fall from the Barrow Neurological Institute (BNI) Falls Evaluation.

Described herein are methods of treating posture instability, static balance, locomotor disability and gait in a subject with neurodegenerative disease, the methods may comprise administering to the subject a dosage form comprising nicotinic acetylcholine receptor (nAChR) agonist. The nAChR agonist may be specific for the α7, β32, or α7 and β2 subunit of the nAChR. The nAChR agonist may be a full agonist. The nAChR agonist may be selected from Varenicline, A-85380, sazetidine, TC-2696, TI-10165, TC-8831, TC-10600, ABT-089, ABT-894, AZD1446, ABT-107, AQW051, ABT-894 and ABT-107, 3-Bromocytisine, Acetylcholine, Cytisine, Epibatidine, A-84,543, A-366,833, ABT-418, Altinicline, Dianicline, Ispronicline, Pozanicline, Rivanicline, Tebanicline, TC-1827, Sazetidine A, N-(3-pyridinyl)-bridged bicyclic diamines, (+)-N-(1-azabicyclo [2.2.2]oct-3-yl)benzo[b]furan-2-carboxamide, A-582941, AR-R17779, Amyloid beta, TC-1698, TC-5619, EVP-6124, GTS-21, PHA-543,613, PNU-282,987, PHA-709829, SSR-180,711, Tropisetron, WAY-317,538, Anabasine, and ICH-3. The nAChR agonist may be selected from ABT-894, ABT-107, TC-8831, ABT-089, AZD1446, and AQW051. The nAChR agonist may be selected from ABT-894 and ABT-107. A subject treated with the dosage form comprising nicotine may have improved posture stability. A subject treated with the dosage form comprising nicotine may have improved static balance. A subject treated with the dosage form comprising nicotine may have improved locomotor ability. A subject treated with the dosage form comprising nicotine may have improved gait. The improvement of symptoms may comprise utilizing one or more of evaluation tests selected from the group consisting of: Unified Parkinson's Disease Rating Scale (UPDRS), BNI Falls Evaluation, Hoehn & Yahr Staging System, Romberg test, turning test, standing on one leg, tandem gait, step length and velocity. The evaluation utilizing the Unified Parkinson's Disease Rating Scale (UPDRS) may be selected from the group consisting of: Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS). The subject may have Parkinson's disease. The subject may have typical Parkinson's disease. The subject may have Parkinson's disease for at least five years. The subject may have Parkinson's disease for at least four years. The subject may have Parkinson's disease for at least three years. The subject may have Parkinson's disease for at least two years. The subject may have Parkinson's disease for at least one year. The subject may have dopaminergic agent treatment. The dopaminergic agent may be levodopa, carbidopa, dopamine agonist, amantadine, monoamine oxidase B inhibitor, or combination thereof. The subject may be evaluated in: an "off" period, wherein the subject can be about 16 hours off dopaminergic agent treatment; an "on" period, wherein the subject can be about 1 hour after usual morning dose of dopaminergic agent treatment; "off" wherein the dopaminergic treatment can be levodopa, carbidopa, dopamine agonist, amantadine, monoamine oxidase B inhibitor, or combination thereof. The "off" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "off" period may be most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The "on" period may be at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or more than 75 hours. The "on" period may be most 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 75 hours. The subject can have Montreal Cognitive Assessment (MOCA) score of at least 26. The subject can have Montreal Cognitive Assessment (MOCA) score of at least or about 20, 25, 30, 35, 40, or more than 40. The subject may be excluded with disorders selected in the group consisting of: atypical Parkinson, Progressive Supranuclear Palsy (PSP), Multiple System Atrophy (MSA), Primary Freezing of Gait (PFG), Corticobasiler Degeneration, dementia with Montreal Cognitive Assessment (MOCA) score of less than 21, legally blind, orthopedic problems in hips or knees, hips or knees replacements, orthostatic hypotension, schizophrenia, schizo-affective disorder, bipolar disorder, hallucinations, psychoses, delusions, deep brain stimulation (DBS) intervention, history of recent stroke, and history of myocardial infarction. The dosage form may comprise at least 1 mg to 6 mg of the nAChR agonist for a period of 6 months, wherein the dosage form can be escalated upward at treatment intervals. The dosage form may comprise at least or about 1, 2, 3, 4, 5, 6, 7, 8, 9, 10, 11, 12, or more than 12 mg of nAChR agonist. The period may be at least or about 1, 2, 3, 4, 5, 6, 7, 8, 9, 10, 11, 12, or more than 12 months. The dosage form comprises nAChR agonist may be escalated upward at two weeks treatment intervals. The dosage form comprises nAChR agonist may be escalated upward at 1, 2, 3, 4, 5, 6, 7, 8, 9, 10, 11, 12, or more than 12 weeks treatment intervals. The nAChR agonist may administered in an amount less than 24 mg in a period of 24 hours. The nAChR agonist can be administered in an amount of at least or about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 mg. The nAChR agonist can be administered in a period of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 hours. The nAChR agonist can be administered at least 4 times in a period of 24 hours. The nAChR agonist may be administered at least 1, 2, 3, 4, 5, 6, 7, 8, 9, 10, 11, 12, 13, 14, 15, 16, 17, 18, 19, 20, or more than 20 times. The nAChR agonist can be administered about every 6 hours in a period of 24 hours. The nAChR agonist can be administered about every 1, 2, 3, 4, 5, 6, 7, 8, 9, 10, 11, 12, 13, 14, 15, 16, 17, 18, 19, 20, 21, 22, or 23 hours in a period of 24 hours. The therapeutic effectiveness of the administration can be evaluated regularly for a period of at least 2 to 14 months. The therapeutic effectiveness of the administration can evaluated regularly for a period of at least 6 months. The therapeutic effectiveness of the administration can be evaluated regularly for a period of at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, or more than 60 months. The evaluation can be performed every 2 months. The evaluation can be performed every 1, 2, 3, 4, 5, 6, 7, 8, 9, 10, 11, 12, or more than 12 months. The dosage form can be formulated for oral, intravenous, intraarterial, parenteral, buccal, topical, transdermal, rectal, intramuscular, subcutaneous, intraosseous, transmucosal, or intraperitoneal administration. The dosage form can be formulated for oral administration. The dosage form can be formulated as a unit dosage. The composition can be formulated as a unit dosage in liquid, gel, semi-liquid, semi-solid, or solid form. The dosage form can be formulated in a tablet. The dosage form can be formulated in a capsule. The dosage form can be formulated as a food. The dosage form can be formulated as a beverage. The dosage form can be formulated as a dietary supplement.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
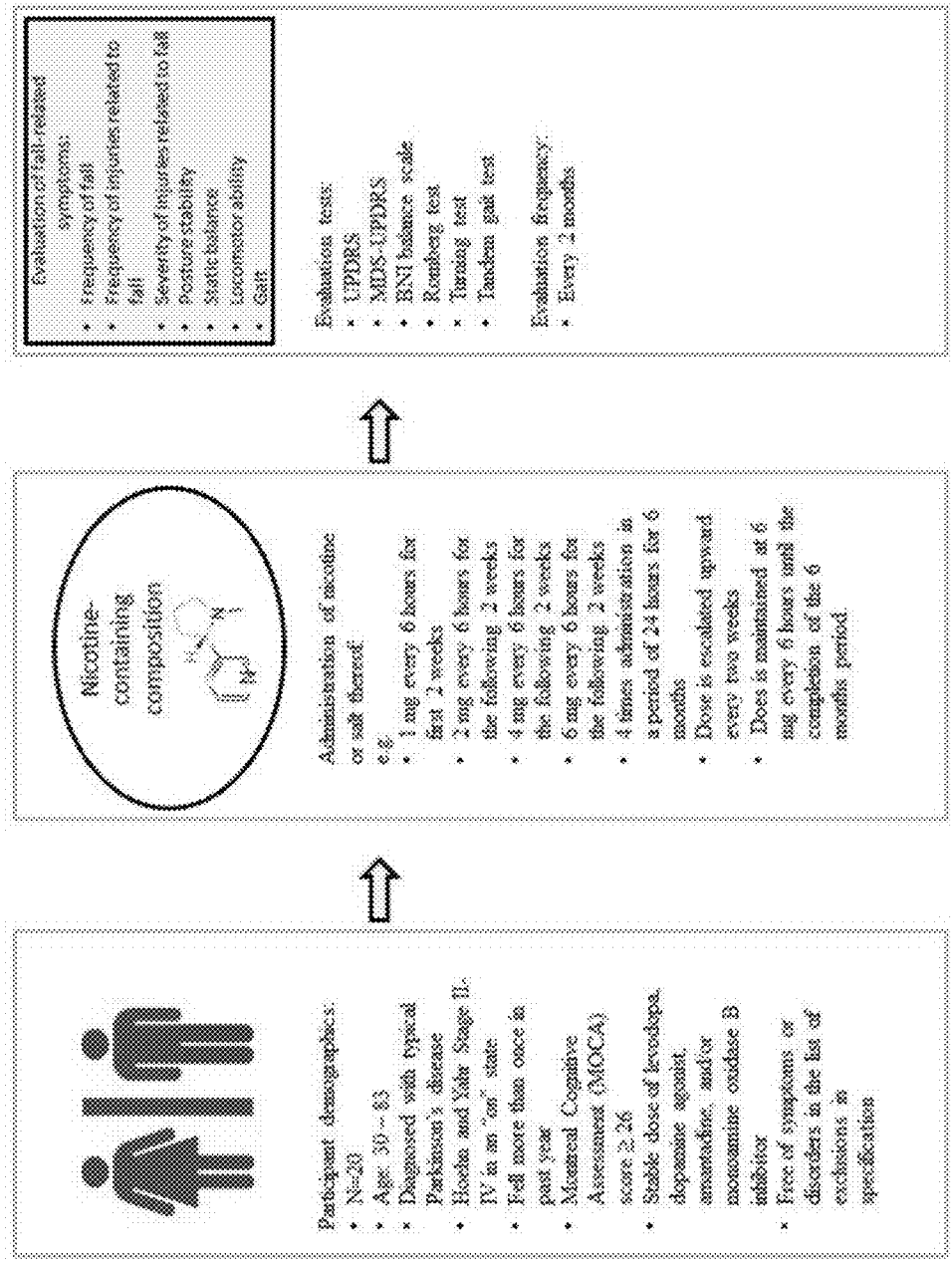
FIG. 1 illustrates a method for treating and evaluation fall-related symptoms in subjects with Parkinson's disease.

As used herein, the term "postural instability" (PI) refers to impaired balance.

As described herein, the term 'balance' refers to a multisystem function that strives to keep the body upright while sitting or standing and while changing posture.

As used herein, the term "zero-order release" refers to a uniform or nearly uniform rate of release of a drug from a dosage form during a given period of release, a rate of release that is independent of the concentration of drug in the dosage form. A dosage form with a zero-order release profile is referred to herein as a "zero-order dosage form." Any zero-order dosage form has the advantage of providing maximum therapeutic value while minimizing side effects.

The term "oral administration," as used herein, refers a form of delivery of a dosage form of a drug to a subject, wherein the dosage form is placed in the mouth of the subject and swallowed.

The term "orally deliverable" herein means suitable for oral administration.

The term "enteric coating," as used herein, refers to a tablet coating that is resistant to gastric juice, and which dissolves after a dosage form with the enteric coating passes out of the stomach, after oral administration to a subject.

A "therapeutic effect," as that term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

The term "excipient," as used herein, means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients can include, by way of illustration and not limitation, diluents, disintegrates, binding agents, adhesives, wetting agents, lubricants, glidants, substances added to mask or counteract a disagreeable taste or odor, flavors, dyes, fragrances, and substances added to improve appearance of the composition.

The term "pH independent release" refers to a rate of release of a drug from a dosage form that does not change when the pH of the environment in which the dosage form is found is changed, e.g., from an acidic pH to a higher pH. The term "pH dependent release" refers to a rate of release of a drug from a dosage form that changes when the pH of the environment in which the dosage form is found is changed from, e.g., an acidic pH to a higher pH.

The terms "NC001" and "NP002" as used herein refer to Nicotine Bitartrate and can be used interchangeably.

In various aspects, the present disclosure relates to compounds, compositions, and methods for treating fall-related symptoms of an individual suffering from diseases associated with neurodegenerative disorders, for example, Parkinson's disease (PD) and PD-related disorders, Alzheimer's disease (AD), dementias, amyotrophic lateral disease (ALS) or Lou Gehrig's disease, Huntington's disease (HD), multiple sclerosis (MS), Spinocerebellar ataxia (SCA), Spinal muscular atrophy (SMA), motor neuron disease (MND) and prion disease. In some embodiments, this is accomplished by administering a therapeutically effective amount of nicotine or salt thereof or a nicotinic receptor modulator to an individual suffering from the diseases. In some embodiments, the present disclosure also relates to compositions comprising nicotine or salt thereof or a nicotinic receptor modulator and a pharmaceutical carrier formulated for administration to an individual suffering from the diseases. As disclosed herein, administering the effective amount of nicotine or salt thereof or a nicotinic receptor modulator to a subject with neurodegenerative diseases reduces fall-related symptoms such as reducing frequency of fall, reducing frequency of injuries related to fall, and reducing severity of injuries related to fall, improving posture stability, improving static balance, improving locomotor ability, and improving gait. In some embodiments, the subject has Parkinson's disease (PD) or PD-related disorders, In some embodiments, the subject has typical Parkinson's disease. In some embodiments, the subject has dopaminergic agent treatment.

Fall and Parkinson's Disease

People with neurodegenerative diseases fall more often. Falls, especially recurrent falls, are a major cause of disability in neurodegenerative diseases such as PD (Temlett and Thompson, "Reasons for admission to hospital for Parkinson's disease", Intern Med J 36:524-526, Jul. 7, 2006; Johnell et al., "Fracture risk in patients with parkinsonism: a population-based study in Olmsted County, Minnesota", Age Aging 21: 32-38, January 1992). Falls occur because of impaired, slowed, locomotion and impaired postural stability (balance). Falls, single falls, early in PD (within 1-5 years of after diagnosis), usually occur from impaired, slow locomotion, and usually respond to dopaminergic drugs (e.g., levodopa, dopamine agonists, and monoamine oxidase type B inhibitors). Falls, recurrent falls, falls with injuries, usually occur later (5 or more years after diagnosis).

In a study of 761 hospital admissions for PD 39% were for falls (Temlett and Thompson, "Reasons for admission to hospital for Parkinson's disease", Intern Med J 36:524-526, Jul. 7, 2006). And in a study of 138 persons with PD followed for 10 years, 27% fractured a major bone because of a fall (Johnell et al., "Fracture risk in patients with parkinsonism: a population-based study in Olmsted County, Minnesota", Age Aging 21: 32-38, January 1992). Patients with PD who fall once may do so because of the underlying disease or because of factors such as dementia, visual impairment, leg weakness, orthopedic problems and environmental hazards (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140; Voss et al., "Fall frequency and risk assessment in early Parkinson's disease," Parkinsonism Relat Disord 18: 837-841, Apr. 26, 2012; Wielinski et al., "Falls and injuries resulting from falls among patients with Parkinson's disease and other parkinsonian syndromes", Mov Disord 20: 410-415, Dec. 3, 2004).

Fall-related injuries in addition to reducing mobility and independence are costly. The costs associated with falls in older people, for example, people 65 years or older, are high and estimated, by the Rand Corporation, to reach $30 billion by 2020 (Shekelle et al, "Evidence Report and Evidence-Based Recommendations Falls Prevention Interventions in the Medicare Population Rand Corporation Contract for US Department of Health & Human Services", Sep. 30, 1998-Sep. 29, 2003). These figures are higher in PD, because more people with PD fall more often (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140). If falls can be reduced in PD, they probably can be reduced in the normal elderly and in elderly people with other disorders.

Approximately a third of community-living older adults fall at least once every year in developed countries. The incidence increases with age; falls occur in approximately 50% of community-living older adults aged 85 years or older. Patients with neurological disease, such as Parkinson's disease (PD), multiple sclerosis, stroke or Alzheimer's disease (AD), experience falls more frequently. Reports suggest that 80% of these patients experience at least one fall in a year and typically many experience multiple falls. Falls profoundly impact the health and quality of life of older people. Between 5 and 10% of falls result in serious injuries, such as head injuries or fractures. Even in the absence of a history of falling or when there is no physical injury after a fall, approximately a third of older adults develop a fear of falling that leads to self-imposed restrictions in mobility, reduced activity, depression, social isolation and subsequent increased fall risk. It is not surprising, therefore, that falls and fall-related injuries are a huge medical concern representing an enormous burden to individuals, society and healthcare systems. In 2008, nonfatal and fatal fall-related costs were estimated at US$23.3 billion in the USA and US$1.6 billion just in the UK. National fall-related costs of prevalence-based studies are a dramatic 0.85-1.5% of total healthcare expenditures.

People with neurodegenerative diseases fall more often. Falls, especially recurrent falls, are a major cause of disability in neurodegenerative diseases such as PD (Temlett and Thompson, "Reasons for admission to hospital for Parkinson's disease", Intern Med J 36:524-526, Jul. 7, 2006; Johnell et al., "Fracture risk in patients with parkinsonism: a population-based study in Olmsted County, Minnesota", Age Aging 21: 32-38, January 1992). Falls occur because of impaired, slowed, locomotion and impaired postural stability (balance). Falls, single falls, early in PD (within 1-5 years of after diagnosis), usually occur from impaired, slow locomotion, and usually respond to dopaminergic drugs (e.g., levodopa, dopamine agonists, and monoamine oxidase type B inhibitors). Falls, recurrent falls, falls with injuries, usually occur later (5 or more years after diagnosis).

In a study of 761 hospital admissions for PD 39% were for falls (Temlett and Thompson, "Reasons for admission to hospital for Parkinson's disease", Intern Med J 36:524-526, Jul. 7, 2006). And in a study of 138 persons with PD followed for 10 years, 27% fractured a major bone because of a fall (Johnell et al., "Fracture risk in patients with parkinsonism: a population-based study in Olmsted County, Minnesota", Age Aging 21: 32-38, January 1992). Patients with PD who fall once may do so because of the underlying disease or because of factors such as dementia, visual impairment, leg weakness, orthopedic problems and environmental hazards (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140; Voss et al., "Fall frequency and risk assessment in early Parkinson's disease," Parkinsonism Relat Disord 18: 837-841, Apr. 26, 2012; Wielinski et al., "Falls and injuries resulting from falls among patients with Parkinson's disease and other parkinsonian syndromes", Mov Disord 20: 410-415, Dec. 3, 2004).

Fall-related injuries in addition to reducing mobility and independence are costly. The costs associated with falls in older people, for example, people 65 years or older, are high and estimated, by the Rand Corporation, to reach $30 billion by 2020 (Shekelle et al, "Evidence Report and Evidence-Based Recommendations Falls Prevention Interventions in the Medicare Population Rand Corporation Contract for US Department of Health & Human Services", Sep. 30, 1998-Sep. 29, 2003). These figures are higher in PD, because more people with PD fall more often (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140). If falls can be reduced in PD, they probably can be reduced in the normal elderly and in elderly people with other disorders.

Falls are a major risk for Parkinson's disease (PD) patients. Falls occur mostly due to impaired, slowed, locomotion and impaired postural stability or balance. Recent researches show that people with PD often have single falls or recurrent falls (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140). Single falls, such as falls occur once in a year, in older people may be related to underlying disease or may be accidental. Recurrent falls, such as falls occur more than once in a year, are more likely to be related to the underlying disease. Recurrent falls may also cause injuries or increase the severity of injuries related to fall.

Recurrent fallers, known as people who have recurrent falls, differed significantly from single and non-fallers, known as people who have single fall or do not fall, in duration and severity of PD. They also differed significantly from single and non-fallers in freezing of gait (FOG), postural instability (e.g., the "pull test") and static balance (e.g., inability to stand on one leg<3 seconds).

People with PD fall more often than people without PD. Single falls are common in people with PD within 1-5 years of diagnosis. Usually, single falls can be treated with dopaminergic drugs, for example, levodopa, carbidopa, dopamine agonists, monoamine oxidase type B inhibitors and amantadine. Recurrent falls are common in people diagnosed with PD for at least 5 years.

Falls early in PD, probably arise from impaired, slowed locomotion. Slowed locomotion is corrected by dopaminergic drugs, hence falls early in PD are decreased by such drugs. Later in PD (5 or more years after diagnosis) recurrent falls occur despite such drugs. Falls late in PD occur possibly because of impaired postural stability, and impaired postural stability does not respond to dopaminergic drugs or may be made worse by such drugs (Chen R Paradoxical worsening of gait with levodopa in Parkinson disease Neurology 2012 78: 446-447, Hely M A, Morris G L, Wayne G J Sydney Multicenter Study of Parkinson's Disease: Non L-Dopa Responsive Problems Dominate at 15 Years Movement Disorders 20; 2005: 190-199). In some cases, people fall late in PD have recurrent falls and occasionally may be made worse by dopaminergic drug treatments.

Recurrent fallers have PD longer and are more disabled: they have higher Unified Parkinson Disease Rating Scale (UPDRS) scores than single fallers. As a non-limiting example, recurrent fallers are more likely to be unable to stand on one foot for <3 seconds. In some cases, the ability to stand on one foot for <3 seconds can be used to predict recurrent falls in patients with or without freezing of gait. Recurrent fallers are more likely to have freezing of gait, which can serve as a good predictor of recurrent falls but not as good as an inability to stand on one foot for <3 seconds. Together, inability to stand on one foot for <3 seconds and freezing of gait are more likely to predict recurrent falls than the subtests of gait, and postural stability (the "pull test") of the UPDRS.

Besides of the stand on one foot <3 seconds test and the freezing of gait test, the Barrow Neurological Institute balance scale can be a useful addition to the UPDRS scale especially in predicting recurrent falls.

Currently, there is variability in the reported prevalence of falls in PD from 11% to 68%. The variability depends on whether specific risk factors are excluded such as dementia, visual loss, neuropathy resulting in leg weakness or proprioceptive loss, major orthopedic problems involving the hips or knees, orthostatic hypotension resulting from anti-hypertensives, diuretics, anti-depressants or dehydration, imbalance resulting from tranquillizers, sedatives, or alcohol. The variability in reporting also depends upon whether only serious falls (requiring medical attention) or non-serious falls (not requiring medical attention) were recorded.

The variability is affected by whether patients with atypical Parkinson disorders such as Progressive Supranuclear Palsy (PSP), Corticobasilar Degeneration (CBD), Multiple System Atrophy (MSA), or Primary Freezing of Gait (PFG), a small number of persons but with a high propensity to fall, are excluded (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140; Voss et al., "Fall frequency and risk assessment in early Parkinson's disease," Parkinsonism Relat Disord 18: 837-841, Apr. 26, 2012). Falls in atypical Parkinson disorders occur early, falls in PD usually occur late in the disease.

Fall severity can be categorized as falls that require medical attention or falls that do not require medical attention. Typically a serious fall is one that requires medical attention, and can be defined with the following criteria: 1) the person falls on the floor, without loss of consciousness, all 4 limbs or the skull hitting the ground; 2) the person needed help in arising; 3) the person twisted a joint or sustained a fracture. Typically, the persons with PD may visit an Emergency Room or an Urgent Care Center.

A single fall, although serious, may be only partly related or even unrelated to PD. However some people with PD fall repeatedly (Lieberman et al, "Comparison of Parkinson disease patients who fell once with patients who fell more than once (Recurrent fallers)", J. Alzheimers Dis Parkinsonism, 4(2), Mar. 15, 2014; doi: 10.4172/2161-0460.1000140; Lieberman A, "Falls in Parkinson disease: the relevance of short steps", J Nov Physiother 4(3), Apr. 18, 2014; doi: 10.4172/2165-7025.1000209). In these studies, the role of impaired postural stability was stressed. The mechanisms underlying impaired postural stability are not known. Attention, however, is focused on the central nervous system (CNS) cholinergic system (Chung K A, Lobb B M, Nutt J G, Horak F B, "Effects of a central cholinesterase inhibitor on reducing falls in Parkinson disease", Neurology 2010 75: 1263-1269; Sep. 1, 2010).

Locomotion, e.g. short steps, is significantly decreased in recurrent versus single fallers and less decreased in single versus non-fallers. Impaired balance, not locomotion, is the main cause of falls in PD. Without being limited by any theory, cholinergic mechanisms related to cholinergic centers in the basal forebrain and the pre-peduncular nucleus (PPN) may play a key role in maintaining postural stability and may play a key role in preventing or ameliorating falls.

NP002, a central cholinergic agonist, was recently evaluated as a possible treatment for levodopa-induced dyskinesias (LIDs) in PD as disclosed in U.S. patent application Ser. No. 12/901,354, filed Oct. 8, 2010. NP002 is a small molecule, a usually orally available nicotinic receptor agonist, that has been shown in preclinical studies to reduce LIDs without affecting Parkinsonian symptoms. NP002 may also be helpful in PD patients with impaired postural stability who fall.

Posture Instability and Balance

Postural instability (PI), or impaired balance, is common in PD patients such as idiopathic Parkinson's disease (IPD), especially as the disease severity advances (Bronte-Stewart et al., "Postural instability in idiopathic Parkinson's disease: the role of medication and unilateral pallidotomy", Brain 125: 2100-2114, September 2002). Faulty balance mechanisms may contribute to fall-related injuries, restriction of gait patterns and decreased mobility. These disabilities lead to loss of functional independence and social isolation.

Balance is needed to keep the body oriented appropriately while performing voluntary activity, during external perturbations and when the support surface or environment changes. Horak et al. (Horak et al., "Postural inflexibility in parkinsonian subjects", J Neurol Sci 111: 46-58; 1992) proposed that balance or postural stability requires three distinct processes: (i) sensory organization, in which one or more of the orientational senses (somatosensory, visual and vestibular) are involved and integrated within the CNS; (ii) a motor adjustment process involved with executing coordinated and properly scaled neuromuscular responses; and (iii) the background tone of the muscles, through which changes in balance are effected.

Organization of the orientational senses is understood to be an adaptive hierarchical system. There are two main reference frames for the sensory representation of the body posture with respect to space. On a lower level, a weighted combination of orientational inputs directly mediates the activity of postural muscles and mainly controls the horizontal centre of gravity (COG) position (the bottom-up organization). On a higher level, vestibular inputs provide the orientational reference, against which conflicts in support surface and visual orientation are identified and the combination of inputs adapted to the task conditions (the top-down organization). For postural stability, the information from the lower level must be coherent with the inertial-gravitational reference of the higher level, and any conflicting orientation inputs must be quickly suppressed in favour of those congruent with the internal reference. Thus, in adults, the sensory organizational process is context specific due to the rapid weighting and re-weighting of sensory inputs to/from the lower level by the higher level adaptive process.

Clinical measures of postural control in PD are typically derived from items in standardized clinical rating scales, such as the Unified Parkinson's Disease Rating Scale (UP-DRS) (Fahn S, Elton R L, members of the UPDRS Development Committee. Unified Parkinson's Disease Rating Scale. In: Fahn S, Marsden C, Calne D, editors. Recent developments in Parkinson's disease. Florham Park (NJ): Macmillan Healthcare Information; 1987. P. 153-163). The commonly accepted Postural Instability and Gait Disorder (PIGD) subscore comprises historical questions relating to falling, walking and freezing, and objective ratings of the patient's ability to change posture, walk and maintain equilibrium during a retropulsive or propulsive pull (Lozano et al., "Effect of GPi pallidotomy on motor function in Parkinson's disease", Lancet 346: 1383-1387; 1995).

There are limitations of the MDS-UPDRS motor scale in evaluating postural stability or balance, only 24 out of 132 points are devoted to axial or midline testing. As a supplementary approach, testing which better reflects problems in posture stability or balance can be further assessed utilizing Romberg test, Turning test, Standing on one leg test, and Tandem gait test.

Postural instability (PI), or impaired balance, is common in PD patients such as idiopathic Parkinson's disease (IPD), especially as the disease severity advances (Bronte-Stewart et al., "Postural instability in idiopathic Parkinson's disease: the role of medication and unilateral pallidotomy", Brain 125: 2100-2114, September 2002). Faulty balance mechanisms may contribute to fall-related injuries, restriction of gait patterns and decreased mobility. These disabilities lead to loss of functional independence and social isolation.

Cognitive Impairment

The relationship between attention and the control of posture and gait have been widely described in patients with Parkinson Disease (PD). There is evidence that cholinergic mechanisms related to cholinergic centers in the basal forebrain and the prepeduncular nucleus (PPN) play a key role in maintaining postural stability. They also play a key role in preventing or ameliorating falls. Subtle disturbances in gait can be observed in ageing and in (preclinical) subtypes of dementia that are not known for prominent motor disturbances, supporting a close relationship between gait and cognition. Some examples of these dementias are mild cognitive impairment, Alzheimer's Disease, vascular cognitive impairment, Subcortical Ischemic Vascular Dementia, Frontotemporal Mild Cognitive Impairment, and Frontotemporal Dementia.

Brain neuroimaging findings may link cognition, gait and fall risk and white matter changes may be linked to postural instability, gait disturbances and falls in older adults. If cognitive deficits are in the causal pathway and they exacerbate the risk of falls or prevent appropriate compensatory mechanisms, improvement of cognitive abilities, at least certain aspects, may improve gait and reduce the risk of falls, especially in more challenging conditions that rely on executive function.

Many research studies show findings that indicate that all aspects of balance control deteriorate with increasing severity of cognitive impairment and that executive function plays an important role in balance control. It has been established that gait impairments predict cognition, and cognition impairment is a risk factor for falls in PD. Several cognitive operations within the brain are a function of intact neuronal nicotinic acetylcholine receptors (neuronal nAChRs) localized in discrete neuroanatomical pathways. Dementia of the Alzheimer's type offers an example of the correlation between profound cognitive impairment and impaired neuronal nAChR function. Nicotine regulates ACh release from areas involved in cognition that are putatively defective in schizophrenia. There is ample evidence that these receptors are involved in normal cognitive operations within the brain.

Nicotine offers the ability to enhance cognition and provide neuroprotection. nACHR agonists could act as therapeutic agents for treating cognition impairment in Alzheimer's Disease and schizophrenia, and most notably in Parkinson's Disease. As PD progresses, the treatment of non-motor symptoms such as cognitive impairment takes precedence over the treatment of non-motor symptoms such as cognitive impairment takes precedence over the treatment of motor symptoms. The majority of the morbidity and mortality associated with PD si related to non-motor aspects, including cognition, and gait and balance. Falls and postural instability are major problems in Parkinson disease (PD) and, unlike gait, are largely unresponsive to dopaminergic replacement. Falls, injuries related to falls and fear of falling pose a major problem in PD. Improving postural stability and reducing falls improves the lives of PD patients.

Nicotine

In one aspect, the present disclosure provides methods and compositions utilizing nicotine or salt thereof for treating fall-related symptoms as well as cognitive symptoms in a subject with neurodegenerative disease, e.g. Parkinson's disease or Parkinson-related disease. Details of the disclosure are described herein.

Nicotine may be isolated and purified from nature or synthetically produced in any manner. This term "nicotine" is also intended to encompass the commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23. The systematic name of nicotine is (S)-3-[1-methylpyrrolidin-2-yl]pyridine and its structure is:

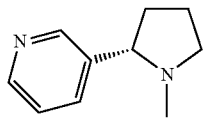

Unless specifically indicated otherwise, the term "nicotine" further includes any pharmacologically acceptable derivative or metabolite of nicotine which exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof A number of useful derivatives of nicotine are disclosed within the Physician's Desk Reference (most recent edition) as well as Harrison's Principles of Internal Medicine. Methods for production of nicotine derivatives and analogues are well known in the art. See, e.g., U.S. Pat. Nos. 4,590,278; 4,321,387; 4,452,984; 4,442,292; and 4,332,945.

The compounds of the present invention may have asymmetric carbon atoms. All isomers, including diastereomeric mixtures such as racemic mixtures and pure enantiomers are considered as part of the invention.

Without being limited to any one theory, one mechanism of action can be that after a prolong exposure to nicotinic receptor agonist nicotinic receptors become desensitized and the nicotinic receptor agonists start working as nicotinic receptor antagonists. In some embodiments, the nicotinic receptor agonists work as antagonists to reduce or eliminate a side effect induced by a dopaminergic agent.

In some embodiments, the disclosure provides a composition for administration of nicotine to an animal. In some embodiments, the disclosure provides a composition for administration of nicotine to an animal to reduce a symptom of a neurodegenerative disorder, e.g., for the oral delivery of nicotine, that contain at least about 1, 5, 10, 20, 30, 40, 50, 60, 70, 80, 90, 95, 99, 99.5, 99.9, or 99.99% nicotine. In some embodiments, the disclosure provides a composition for administration of nicotine to an animal to reduce a side effect of a dopaminergic agent, e.g., for the oral delivery of nicotine, that contain at least about 1, 5, 10, 20, 30, 40, 50, 60, 70, 80, 90, 95, 99, 99.5, 99.9, or 99.99% nicotine. In some embodiments, the disclosure provides a composition for the oral delivery of nicotine that contains no more than about 2, 5, 10, 20, 30, 40, 50, 60, 70, 80, 90, 95, 99, 99.5, 99.9, 99.99, or 100% nicotine. In some embodiments, the disclosure provides a composition that contains about 1-100% nicotine, or about 10-100% nicotine, or about 20-100% nicotine, or about 50-100% nicotine, or about 80%-100% nicotine, or about 90-100% nicotine, or about 95-100% nicotine, or about 99-100% nicotine. In some embodiments, the disclosure provides a composition that contains about 1-90% nicotine, or about 10-90% nicotine, or about 20-90% nicotine, or about 50-90% nicotine, or about 80-90% nicotine. In some embodiments, the disclosure provides a composition that contains about 1-75% nicotine, or about 10-75% nicotine, or about 20-75% nicotine, or about 50-75% nicotine. In some embodiments, the disclosure provides a composition that contains about 1-50% nicotine, or about 10-50% nicotine, or about 20-50% nicotine, or about 30-50% nicotine, or about 40-50% nicotine. In some embodiments, the disclosure provides a composition that contains about 1-40% nicotine, or about 10-40% nicotine, or about 20-40% nicotine, or about 30-40% nicotine. In some embodiments, the disclosure provides a composition that contains about 1-30% nicotine, or about 10-30% nicotine, or about 20-30% nicotine. In some embodiments, the disclosure provides a composition that contains about 1-20% nicotine, or about 10-20% nicotine. In some embodiments, the disclosure provides a composition that contains about 1-10% nicotine. In some embodiments, the disclosure provides a composition that contains about 1, 2, 5, 10, 20, 30, 40, 50, 60, 70, 80, 90, 95, 96, 97, 98, or 99% nicotine.

In some embodiments, the a concentration of nicotine is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, a concentration of nicotine is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25% 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25% 7%, 6.75%, 6.50%, 6.25% 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, a concentration of nicotine is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, a concentration of nicotine is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of nicotine is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of nicotine is equal or greater than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Nicotinic Receptor Modulators

In some embodiments, the disclosure provides compositions and methods utilizing a nicotinic receptor modulator, e.g., to reduce or eliminate a side effect associated with dopaminergic agent treatment. A nicotinic receptor modulator can be an agonist or it can be an antagonist. Details of the disclosure are described herein.

In one aspect, The term "agonist" as used herein refers to a molecule having the ability to initiate or enhance a biological function of a target polypeptide. Accordingly, the term "agonist" is defined in the context of the biological role of the target polypeptide. While preferred agonists herein specifically interact with (e.g. bind to) the target, molecules that enhance a biological activity of the target polypeptide by interacting with other members of the signal transduction pathway of which the target polypeptide is a member are also specifically included within this definition. Agonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

The term "antagonist" as used herein refers to a molecule having the ability to inhibit a biological function of a target polypeptide. Accordingly, the term "antagonist" is defined in the context of the biological role of the target polypeptide. While preferred antagonists herein specifically interact with (e.g. bind to) the target, molecules that inhibit a biological activity of the target polypeptide by interacting with other members of the signal transduction pathway of which the target polypeptide is a member are also specifically included within this definition. Antagonists, as defined herein, without limitation, include antibodies, antibody derivatives, antibody fragments and immunoglobulin variants, peptides, peptidomimetics, simple or complex organic or inorganic molecule, antisense molecules, oligonucleotide decoys, proteins, oligonucleotide, vitamin derivatives, carbohydrates, and toxins.

In some embodiments, the nicotinic receptor modulator modulates a nicotinic receptor in the brain. In some embodiments, the nicotinic receptor modulator modulates a nicotinic receptor in the striatum or substantia niagra. In some embodiments, the nicotinic receptor modulator modulates a nicotinic receptor comprising at least one α subunit or a nicotinic receptor containing at least one α subunit and at least one β subunit. In some embodiments, the α subunit is selected from the group consisting of α2, α3, α4, α5, α6, α7, α8, α9, and α10 and the β subunit is selected from the group consisting of β2, β3 and β4. In some embodiments, the nicotinic receptor modulator modulates a nicotinic receptor comprising subunits selected from the group consisting of α4β2, α6β2, α4α6β2, α4β5β2, α4α6β2β3, α6β2β3 and α4α2β2. In some embodiments, the nicotinic receptor modulator modulates a nicotinic receptor comprising at least one α subunit selected from the group consisting of α4, α6, and α7.

The nicotinic receptor agonist of the disclosure may be any ligand that binds to and activates the nicotinic receptor, thereby resulting in a biological response. The potential of a given substance to act as a nicotinic receptor agonist may be determined using standard in vitro binding assays and/or standard in vivo functionality tests.

Other nicotinic receptor agonists include choline esterase inhibitors (e.g., that increase local concentration of acetylcholine), derivatives of epibatidine that specifically bind the neuronal type of nicotinic receptors (with reduced binding to the muscarinic receptor) and having reduced deleterious side-effects (e.g., Epidoxidine, ABT-154, ABT418, ABT-594; Abbott Laboratories (Damaj et al. (1998) J. Pharmacol Exp. Then 284:1058 65, describing several analogs of epibatidine of equal potency but with high specificity to the neuronal type of nicotinic receptors). Further nicotinic receptor agonists of interest include, but are not necessarily limited to, N-methylcarbamyl and N-methylthi-O-carbamyl esters of choline (e.g., trimethylaminoethanol) (Abood et al. (1988) Pharmacol. Biochem. Behay. 30:403 8); acetylcholine (an endogenous ligand for the nicotinic receptor); and the like.

Multiple nicotinic acetylcholine receptors (nAChRs) exist throughout the body. The nAChRs $\alpha1\beta1$, $\alpha3\beta4$ and $\alpha7$ nAChRs are the major subtypes in the peripheral nervous system and $\alpha4\beta2$, $\alpha6\beta2$ and $\alpha7$ nAChRs the primary subtypes in the brain. Varenicline, which acts at all nAChRs, as well as several $\beta2$ selective drugs (A-85380, sazetidine, TC-2696, TI-10165, TC-8831 and TC-10600) may reduce LIDs. Similarly, other $\beta2$ selective agonists such as ABT-089, a partial $\beta2$ nAChR agonist (Ki=17 nM) and the full $\beta2$ agonist ABT-894 (Ki=0.3 nM) may decrease LIDs. AZD1446, a $\beta2$ nAChR agonist of relatively low affinity (Ki=30 nM) may also reduce LIDs, while full high affinity $\beta2$ nAChR agonists may be more effective. In addition, $\alpha7$ nAChR agonist ABT-107 (Ki=0.5 nM) and AQW051 (Ki=27 nM) may also reduce LIDs and the greatest reduction in LIDs may be associated with higher affinity ($\geq10$ nM) full nAChR agonists such as ABT-894 and ABT-107. Partial agonists or drugs with lower affinities (such as varenicline, TC-8831, ABT-089, AZD1446, AQW051) may also be efficacious. An important consideration is side effects and drugs such as varenicline and TC-8831 are associated with nausea, and thus may be less desirable. The antidyskinetic effect of nicotine may be receptor-mediated via both $\beta2$ and $\alpha7$ nAChRs and LIDs may be preferably reduced with agonists to $\beta2$ and $\alpha7$ nAChRs. The $\beta2$ and $\alpha7$ nAChRs are in some cases paired with other nAChR subunits. The $\beta2$ and $\alpha7$ nAChRs agonists are selected from known agonists, such as 3-Bromocytisine, Acetylcholine, Cytisine, Epibatidine, A-84,543, A-366,833, ABT-418, Altinicline, Dianicline, Ispronicline, Pozanicline, Rivanicline, Tebanicline, TC-1827, Sazetidine A, N-(3-pyridinyl)-bridged bicyclic diamines, (+)-N-(1-azabicyclo[2.2.2]oct-3-yl)benzo[b]furan-2-carboxamide, A-582941, AR-R17779, Amyloid beta, TC-1698, TC-5619, EVP-6124, GTS-21, PHA-543,613, PNU-282,987, PHA-709829, SSR-180,711, Tropisetron, WAY-317,538, Anabasine, or ICH-3. The $\beta2$ and $\alpha7$ nAChRs agonists are also new agonists developed to target these receptors.

Dopaminergic Agents

In some embodiments, the disclosure provides compositions and methods to reduce or eliminate the side effects of a dopaminergic agent. In some embodiments, the compositions and methods retain or enhance a desired effect of the dopaminergic agent, e.g., antiparkinsonian effect. The methods and compositions of the disclosure apply to any dopaminergic agent for which it is desired to reduce one or more side effects. In some embodiments, the compositions and methods of the disclosure utilize a dopamine precursor. In some embodiments, the compositions and methods of the disclosure utilize a dopamine agonist. Dopaminergic agents include a dopamine precursor or a dopamine receptor agonist. Examples of dopaminergic agents include levodopa, bromocriptine, pergolide, pramipexole, cabergoline, ropinorole, apomorphine, carbidopa, dopamine agonists, monoamine oxidase type B inhibitors, amantadine or a combination thereof.

In some embodiments, the compositions and methods of the disclosure utilize one or more agents used in the art in combination with a dopamine agent treatment to achieve a therapeutic effect. For instance, in one exemplary embodiment the compositions and methods of the invention utilize levodopa in combination with an agent such as carbidopa, which blocks the conversion of levodopa to dopamine in the blood. In yet another exemplary embodiment, the compositions and methods of the disclosure utilize levodopa in combination with a dopaminergic agonist. In yet another exemplary embodiment, the compositions and methods of the disclosure utilize levodopa in combination with monoamine oxidase type B (MAO-B) inhibitor such as selegiline. In yet another exemplary embodiment, the compositions and methods of the disclosure utilize levodopa in combination with amantadine. In yet another exemplary embodiment, the compositions and methods of the disclosure utilize levodopa in combination with a COMT Inhibitor, such as entacapone.

Levodopa

Levodopa, an aromatic amino acid, is a white, crystalline compound, slightly soluble in water, with a molecular weight of 197.2. It is designated L-3,4-dihydroxyphenylalanine or (S)-2-amino-3-(3,4-dihydroxyphenyl) propanoic acid. Its structural formula is:

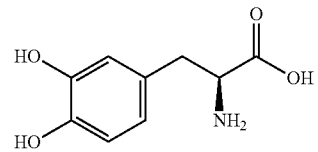 [SMILES: N[C@@H](Cc1ccc(O)c(O)c1)C(=O)O]

Levodopa is used for the treatment of Parkinson's disease. Parkinson's disease is a progressive, neurodegenerative disorder of the extrapyramidal nervous system affecting the mobility and control of the skeletal muscular system. Its characteristic features include resting tremor, rigidity, and bradykinetic movements. Current evidence indicates that symptoms of Parkinson's disease are related to depletion of dopamine in the corpus striatum. Administration of dopamine is ineffective in the treatment of Parkinson's disease apparently because it does not cross the blood-brain barrier. However, levodopa, the metabolic precursor of dopamine, does cross the blood brain barrier, and presumably is converted to dopamine in the brain. This is thought to be the mechanism whereby levodopa relieves symptoms of Parkinson's disease.

However, although initially very effective, long term treatment with levodopa gives rise to multiple complications. Levodopa treatment may cause nausea, vomiting, involuntary movements (e.g. dyskinesias), mental disturbances, depression, syncope, and hallucinations. The precise pathophysiological mechanisms of levodopa side effects are still enigmatic, but are thought to be due to increased brain dopamine following administration of levodopa. Previous work has shown that levodopa induced dyskinesias (LIDs) arise due to enhanced intermittent stimulation of D1, D2 and/or other dopamine receptor subtypes. This results in an imbalance in activity of the two major striatal output pathways, possibly through activation of D1 and inhibition of D2 receptors on the direct and indirect dopaminergic pathways, respectively, although there is some overlap between striatal efferents. Recent data suggest that D1 receptors, through enhanced G-protein coupling, may play a more prominent role in functional hypersensitivity associated with levodopa-induced dyskinesias, while D2 receptor activation may be more closely linked to the anti-parkinsonian action of dopaminergic drugs.

Carbidopa

Carbidopa is a white, crystalline compound, slightly soluble in water, with a molecular weight of 244.3. It is designated chemically as (−)-L-α-hydrazino-α-methyl-β-(3, 4-dihydroxybenzene) propanoic acid monohydrate. Its structural formula is:

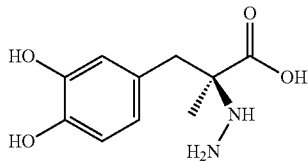 [SMILES: C[C@@](Cc1ccc(O)c(O)c1)(NN)C(=O)O]

Carbidopa is a drug given to people with Parkinson's disease and is used in tandem with levodopa. Administration of carbidopa with levodopa can increase the plasma half-life of levodopa from 50 minutes to 1½ hours. Carbidopa typically does not cross the blood brain barrier and can inhibit peripheral aromatic-L-amino acid decarboxylase (DOPA Decarboxylase or DDC). Without being bound by any theory, carbidopa can inhibit peripheral metabolism of levodopa, prevents the conversion of levodopa to dopamine peripherally, and allow a greater proportion of peripheral levodopa to cross the blood brain barrier for central nervous effect, thereby reducing the side effects caused by dopamine on the periphery, as well as increasing the concentration of levodopa and dopamine in the brain.

Carbidopa is commonly used to inhibit the activity of dopamine decarboxylase, an enzyme known to break down levodopa in the periphery and converts it to dopamine. This can results in the newly formed dopamine being unable to cross the blood brain barrier and the effectiveness of levodopa treatments is greatly decreased. Carbidopa can reduce the amount of levodopa required to produce a given response by about 75% and, when administered with levodopa, increases both plasma levels and the plasma half-life of levodopa, and decreases plasma and urinary dopamine and homovanillic acid. Carbidopa can also eliminate the half-life of levodopa by about 1.5 hours.

In some cases, carbidopa and levodopa are administered in a combined composition. Examples commercially available medicament of the combination of carbidopa/levodopa includes the brand names of Kinson, Sinemet, Parcopa and Atamet, while Stalevo further comprises entacapone, which enhances the bioavailability of carbidopa and levodopa.

Dopamine Agonist

A dopamine agonist is a compound that activates dopamine receptors in the absence of that receptor's physiological ligand, the neurotransmitter dopamine. Dopamine agonists can treat hypodopaminergic (low dopamine) conditions; they are typically used for treating Parkinson's disease, attention deficit/hyperactivity disorder (in the form of stimulants) and certain pituitary tumors (prolactinoma), and may be useful for restless legs syndrome (RLS). Both Requip (Ropinirole) and Mirapex (Pramipexole) are FDA-approved for the treatment of RLS. There is also an ongoing clinical trial to test the effectiveness of the dopamine agonist Requip (ropinirole) in reversing the symptoms of SSRI-induced sexual dysfunction and Post-SSRI sexual dysfunction (PSSD).

Some drugs can act as dopamine agonist. Typically, there are two classes of commercially available dopamine agonists, partial agonist and agonist of full/unknown efficacy. Examples of partial agonist include, but not limited to, Aripiprazole, Quinpirole, and Salvinorin. Examples of agonist of full/unknown efficacy include, but not limited to, apomorphine, bromocriptine, cabergoline, ciladopa, dihydrexidine, dinapsoline, doxanthrine, epicriptine, lisuride, pergolide, piribedil, pramipexole, propylnorapomorphine, quinagolide, ropinirole, rotigotine, roxindole, sumanirole, and fenoldopam.

Amantadine

Amantadine, commercially known as Symmetrel (Endo Pharmaceuticals) is a drug that has the Food and Drug Administration of the United States approval for use both as an antiviral and an antiparkinsonian drug. It is the organic compound 1-adamantylamine or 1-aminoadamantane, meaning it consists of an adamantane backbone that has an aminio group substituted at one of the four methyne positions. Its structural formula is:

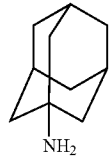

Rimantadine is a closely related derivative of adamantane with similar biological properties.

Amantadine is a weak antagonist of the NMDA-type glutamate receptor. It can increase dopamine release, block dopamine reuptake, and can be a therapy for Parkinson's disease. Although, as an anti-parkinsonian, it can be used as monotherapy, or together with levodopa to treat levodopa-related motor fluctuations such as shortening of levodopa duration of clinical effect, and levodopa-related dyskinesias.

Monoamine Oxidase B Inhibitor

Monoamine oxidase inhibitors (MAOIs) are chemicals which inhibit the activity of the monoamine oxidase enzyme family. MAOIs can prevent the breakdown of monoamine neurotransmitters and can increase their availability. MAOIs have a long history of use as medications prescribed for the treatment of depression, particularly atypical depression, Parkinson's disease and several other disorders.

MAOIs such as selegiline is typically used in the treatment of Parkinson's disease. MAOIs can also be used in the treatment of Parkinson's disease by targeting MAO-B in particular and affecting dopaminergic neurons, as well as providing an alternative for migraine prophylaxis.

Inhibition of both MAO-A and MAO-B is also used in the treatment of clinical depression and anxiety. MAOIs appear to be particularly indicated for outpatients with "neurotic depression" complicated by panic disorder or hysteroid dysphoria, which involves repeated episodes of depressed mood in response to feeling rejected.

MAOIs have also been found to be effective in the treatment of panic disorder with agoraphobia, social phobia, atypical depression or mixed anxiety and depression, bulimia, and post-traumatic stress disorder, as well as borderline personality disorder. MAOIs appear to be particularly effective in the management of bipolar depression according to a recent retrospective-analysis. In some cases, MAOI may be effective in the treatment of obsessive-compulsive disorder (OCD), trichotillomania, dysmorphophobia, and avoidant personality disorder.

Without being limited to any theory, MAOIs act by inhibiting the activity of monoamine oxidase, thus preventing the breakdown of monoamine neurotransmitters and and thereby increasing their availability. There are two isoforms of monoamine oxidase, MAO-A and MAO-B. MAO-A preferentially deaminates serotonin, melatonin, epinephrine, and norepinephrine. MAO-B preferentially deaminates phenylethylamine and trace amines. Dopamine is equally deaminated by both types.

Side Effects

The principal adverse reactions of dopaminergic agent include headache, diarrhea, hypertension, nausea, vomiting, involuntary movements (e.g. dyskinesias), mental disturbances, depression, syncope, hallucinations, and abnormal renal function.

The disclosure provides compositions and methods utilizing nicotine or salt thereof, or a nicotinic receptor modulator that reduces or eliminates a side effect associated with dopaminergic agent treatment. In some embodiments, the disclosure provides compositions and methods utilizing a nicotinic receptor modulator that reduces or eliminates dyskinesias associated with dopaminergic agent treatment. Without being limited to any theory, one possibility is that nicotinic receptor modulator exerts its effect by acting at nicotinic acetylcholine receptors (nAChR), which are expressed in the striatum. There is a dense cholinergic innervation in striatum that closely coincides with dopaminergic neurons. Under physiological conditions, these cholinergic interneurons tonically release acetylcholine, which stimulates nicotinic receptors on dopaminergic nerve terminals to release dopamine. Similarly, exogenously applied agents such as nicotine result in a release of dopamine from striatal terminals Methods of Treatment In one aspect, the present disclosure provides for a method of treating fall-related symptoms in a subject with neurodegenerative disease comprising administering nicotine or salt thereof to the subject. In some embodiments, the nicotine and salt thereof is administered in dosage form. The administration of nicotine or salt thereof can reduce frequency of fall, reduce frequency of injuries related to fall, and/or reduce severity of injuries related to fall in a subject with neurodegenerative diseases, e.g. Parkinson's disease or Parkinson's-related diseases. In some embodiments, the subject has typical Parkinson's disease. In some embodiments, the subject is diagnosed for Parkinson's disease for at least 5 years. In some embodiments, the subject is on dopaminergic agent treatment. In some embodiments, the subject has fallen or recurrent falls in past year.

In various embodiments, the present disclosure provides for a method of treating fall-related symptoms in a subject with neurodegenerative disease comprising administering a composition comprising a nicotinic receptor modulator to the subject. In some embodiments, the composition is administered in dosage form. In some embodiments, the nicotinic receptor modulator is a nicotinic receptor agonist or antagonist. The administration of the composition can reduce frequency of fall, reduce frequency of injuries related to fall, and/or reduce severity of injuries related to fall in a subject with neurodegenerative diseases, e.g. Parkinson's disease or Parkinson's-related diseases. In some embodiments, the subject has typical Parkinson's disease.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the subject has Parkinson's disease or Parkinson's-related diseases. In some embodiments, the subject has fallen and recurrent falls in past year. In some embodiments, the subject has fallen at least 1 time, 2 times, 3 times, 4 times, 5 times, 6 times, or more in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the subject has Parkinson's disease or Parkinson's-related diseases. In some embodiments, the subject has increased frequency of fall in past year compared to the year before. In some embodiments, the frequency of fall is increased by at least 1 time, 2 times, 3 times, 4 times, 5 times, 6 times, 7 times, 8 times, 9 times, 10 times, 20 times, 50 times, 100 times, 1000 times or more in past year. In some embodiments, the frequency of fall is increased between about 1 to 1000 times in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the subject has Parkinson's disease or Parkinson's-related diseases. In some embodiments, present disclosure provides a method for reducing frequency of fall in subject with neurodegenerative disease. In some embodiments, the frequency of fall is reduced by at least 1 time, 2 times, 3 times, 4 times, 5 times, 6 times, 7 times, 8 times, 9 times, 10 times, 20 times, 50 times, 100 times, 1000 times or more in past year. In some embodiments, the frequency of fall is increased between about 1 to 1000 times in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the subject has increased frequency of injuries related to fall in past year compared to the year before. The frequency of injuries related to fall is by at least 1 to 1000 times. In some embodiments, the frequency of injuries related to fall is increased between about 1 to 1000 times in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the present disclosure provides a method for reducing the frequency of injuries related to fall. In some embodiments, the frequency of injuries related to fall is reduced by at least 1 to 1000 times. In some embodiments, the frequency of injuries related to fall is increased between about 1 to 1000 times in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the subject has increased severity of injuries related to fall in past year compared to the year before. In some embodiments, the severity of injuries related to fall is increased by at least 1 to 1000 times. In some embodiments, the severity of injuries related to fall is increased between about 1 to 1000 times in past year.

In some embodiments, the present disclosure utilizes a nicotinic receptor agonist, such as nicotine or salt thereof for treatment of fall-related symptoms in a subject with neurodegenerative diseases. The method comprises administering nicotine or salt thereof to a subject in need thereof. In some embodiments, the present disclosure provides a method for reducing the severity of injuries related to fall. In some embodiments, the severity of injuries related to fall is reduced by at least 1 time, 2 times, 3 times, 4 times, 5 times, 6 times, 7 times, 8 times, 9 times, 10 times, 20 times, 50 times, 100 times, 1000 times or more in past year. In some embodiments, the severity of injuries related to fall is increased between about 1 to 1000 times in past year.

In various embodiments, the present disclosure provides for a method of predicting recurrent falls in in a subject with neurodegenerative disease comprising administering nicotine or salt thereof to the subject. In some embodiments, the nicotine and salt thereof is administered in dosage form. The administration of nicotine or salt thereof can reduce frequency of fall, reduce frequency of injuries related to fall, and/or reduce severity of injuries related to fall in a subject with neurodegenerative diseases, e.g. Parkinson's disease or Parkinson's-related diseases. In some embodiments, the subject has typical Parkinson's disease. In some embodiments, the subject is diagnosed for Parkinson's disease for at least 5 years. In some embodiments, the subject is on dopaminergic agent treatment. In some embodiments, the subject has fallen at least once and/or has recurrent falls in past year.

In some embodiments, the present disclosure provides for a method of treating fall-related symptoms in a subject with Parkinson's disease or Parkinson's-related diseases comprising administering nicotine or salt thereof to the subject. The administration of nicotine or salt thereof can reduce frequency of fall, reduce frequency of injuries related to fall, and/or reduce severity of injuries related to fall in the subject. In some embodiments, the subject is on dopaminergic agent treatment. Non limiting examples of dopaminergic agents includes levodopa, bromocriptine, pergolide, pramipexole, cabergoline, ropinorole, apomorphine, carbidopa, dopamine agonists, monoamine oxidase type B inhibitors, amantadine or a combination thereof. In some embodiments, the subject is on levodopa, carbidopa, dopamine agonist, amantadine, monoamine oxidase B inhibitor, or combination thereof.

In various embodiments, disclosed herein are methods and compositions for reducing fall-related symptoms in a subject with Parkinson's disease or Parkinson-related disease and is on dopaminergic agent treatment, e.g. levodopa/carbidopa, the methods and compositions comprising administering nicotine or salt thereof to the subject. In some embodiments, the subject has fallen at least or has recurrent falls in past year. The administration of nicotine or salt thereof in combination with a dopaminergic agent can reduce fall-related symptoms, e.g. frequency of fall, frequency of injuries related to fall, severity of injuries related to fall. In various embodiments, utilization of the disclosed methods and compositions reduces side effects related to dopaminergic agent treatment, for example, reducing dyskinesia and improving response fluctuations: "wearing off and of off".

In one aspect, the present disclosure provides for a method of improving posture stability and gait in a subject with neurodegenerative disease comprising administering nicotine or salt thereof to the subject. In some embodiments, the nicotine and salt thereof is administered in dosage form. In some embodiments, administration of nicotine or salt thereof improves posture stability, static balance, locomotor ability, and/or gait in a subject with neurodegenerative diseases, e.g. Parkinson's disease or Parkinson's-related diseases. In some embodiments, the subject has typical Parkinson's disease. In some embodiments, the subject is diagnosed for Parkinson's disease for at least 5 years. In some embodiments, the subject is on dopaminergic agent treatment. In some embodiments, the subject has fallen or recurrent falls in past year.

In some embodiments, the present disclosure provides for a method of improving posture stability and gait in a subject with neurodegenerative disease comprising administering a nicotinic receptor modulator to the subject. In some embodiments, the nicotinic receptor modulator is administered in dosage form. In various embodiments, the nicotinic receptor modulator is a nicotinic receptor agonist. In various embodiments, the nicotinic receptor modulator is a nicotinic receptor antagonist. In some embodiments, administration of the nicotinic receptor modulator improves posture stability, static balance, locomotor ability, and/or gait in a subject with neurodegenerative diseases, such as Parkinson's disease or Parkinson's-related diseases. In some embodiments, the subject has typical Parkinson's disease. In some embodiments, the subject is diagnosed for Parkinson's disease for at least 5 years. In some embodiments, the subject has fallen at least once or has recurrent falls in past year.

In some embodiments, the present disclosure provides for a method of improving posture stability in a subject with neurodegenerative disease comprising administering nicotine or salt thereof to the subject. In some embodiments, the nicotinic receptor agonist is administered in dosage form. In some embodiments, administration of nicotine or salt thereof improves posture stability by least 1 time, 2 times, 3 times, 4 times, 5 times, 6 times, 7 times, 8 times, 9 times, 10 times, 20 times, 50 times, 100 times, 1000 times or more. In some embodiments, posture stability of the treated subject is improved by between about 1 to 1000 times.

In some embodiments, the present disclosure provides for a method of improving static balance in a subject with neurodegenerative disease comprising administering nicotine or salt thereof to the subject. In some embodiments, the nicotinic receptor agonist is administered in dosage form. In some embodiments, administration of nicotine or salt thereof improves static balance by least 1 time, 2 times, 3 times, 4 times, 5 times, 6 times, 7 times, 8 times, 9 times, 10 times, 20 times, 50 times, 100 times, 1000 times or more. In some embodiments, static balance of the treated subject is improved by between about 1 to 1000 times.

In some embodiments, the present disclosure provides for a method of improving locomotor abilities in a subject with neurodegenerative disease comprising administering nicotine or salt thereof to the subject. In some embodiments, the nicotinic receptor agonist is administered in dosage form. In some embodiments, administration of nicotine or salt thereof improves locomotor abilities by least 1 time, 2 times, 3 times, 4 times, 5 times, 6 times, 7 times, 8 times, 9 times, 10 times, 20 times, 50 times, 100 times, 1000 times or more. In some embodiments, locomotor ability of the treated subject is improved by between about 1 to 1000 times.

In some embodiments, the present disclosure provides for a method of improving gait such as freezing of gait and tandem gait in a subject with neurodegenerative disease comprising administering nicotine or salt thereof to the subject. In some embodiments, the nicotinic receptor agonist is administered in dosage form. In some embodiments, administration of nicotine or salt thereof improves gait such as freezing of gait and tandem gait by least 1 time, 2 times, 3 times, 4 times, 5 times, 6 times, 7 times, 8 times, 9 times, 10 times, 20 times, 50 times, 100 times, 1000 times or more. In some embodiments, gait such as freezing of gait and tandem gait of the treated subject is improved by between about 1 to 1000 times.

In some embodiments, the subject has impaired locomotion, slowed locomotion, impaired stability, freezing of gait (FOG), posture instability, static balance problems, loss of balance, unstable walking, and/or short steps. Administering nicotine or salt thereof, or a nicotinic receptor modulator to the subject improves locomotion, gait, posture stability, balance and/or walking. In some embodiments, the subject has improved locomotion, gait, posture stability, balance and/or walking by at least least 1 time, 2 times, 3 times, 4 times, 5 times, 6 times, 7 times, 8 times, 9 times, 10 times, 20 times, 50 times, 100 times, 1000 times, or more, compared to the past year. In some embodiments, the subject has improved locomotion, gait, posture stability, balance and/or walking by between about 1 to 1000 times compared to the past year.

In some embodiments, improvements of fall-related symptoms are evaluated by utilizing standard tests. Exemplary tests are Unified Parkinson's Disease Rating Scale (UPDRS), Barrow Neurological Institute (BNI) Falls Evaluation, Hoehn & Yahr Staging System, Tinetti score, Romberg test, turning test, standing on one leg, tandem gait, step length and velocity.

In some embodiments, the present method comprises evaluating a subject with neurodegenerative disease under dopaminergic agent treatment, the method comprises: (a) an "off" period when the subject is about 16 hours off dopaminergic agent treatment, and (b) an "on" period when the subject is about 1 hour after usual morning dose of dopaminergic agent treatment. In some embodiments, the subject is under dopaminergic agent treatment such as levodopa, carbidopa, dopamine agonists, monoamine type B oxidase inhibitors, and/or amantadine. In some embodiments, the subject has Parkinson's disease or Parkinson-related disease.

Unified Parkinson's Disease Rating Scale (UPDRS)

The Unified Parkinson's Disease Rating Scale (UPDRS) is typically used to follow the longitudinal course of Parkinson's disease. In general, the UPDRS is made up of five sections: Part I: evaluation of mentation, behavior and mood; Part II: self-evaluation of the activities of daily life (ADLs) including speech, swallowing, handwriting, dressing, hygiene, falling, salivating, turning in bed, walking and cutting food; Part III: clinical-scored monitored motor evaluation; Part IV: Hoehn and Yahr staging of severity of Parkinson's disease; and Part V: Schwab and England ADL scale.

These UPDRS sections are evaluated by interview and clinical observation. In some cases, a section may require multiple grades assigned to each extremity. Typically, a clinician or a healthcare profession, or a researcher would use the UPDRS and the motor section in particular to follow the progression of a person's Parkinson's disease. For example, a research may use it to measure the benefits from a given therapy. As another example, a healthcare profession may use it in clinical practice to follow the progression of their patients' symptoms. Following the UPDRS scores over time can provide insight into the patient's disease progression. Typically, the "mentation, behavior and mood" scores increase later in the disease.

The Unified Parkinson's Disease Rating Scale (UPDRS) is the most utilized test for evaluating patients with Parkinson's disease. The original UPDRS has a question in the activities of daily living, on falls. This question is absent on the revised Movement Disorder Society UPDRS (MDS-UPDRS). Both the original UPDRS and the MDS-UPDRS have only one subtest on balance (postural instability), known as the "pull test". This subtest makes up only 4 points out of a total of 132 points, which is about 3% of the motor examination and is a small part for assessing fall in Parkinson's disease patients.

The Movement Disorder Society Revised UPDRS (MDS-UPDRS)

The Movement Disorder Society (MDS) published a revision of the UPDRS, known as the MDS-UPDRS. The revision highlights the limitations of the original UPDRS. Two major limitations include the lack of consistent anchor among subscales and the low emphasis on the nonmotor features of PD. The modified UPDRS retains the four-scale structure with a reorganization of the various subscales. The scales are titled; (1) nonmotor experiences of daily living (13 items), (2) motor experiences of daily living (13 items), (3) motor examination (18 items), and (4) motor complications (six items). Each subscale now has 0-4 ratings, where 0=normal, 1=slight, 2=mild, 3=moderate, and 4=severe.

Tinetti Test (TT)

The Tinetti Test (TT), also known as Performance Oriented Mobility Assessment (POMA) is a common clinical test for assessing a person's static and dynamic balance abilities. The test is in two short sections, one examining static balance abilities in a chair and then standing; the other one is gait. In some cases, the two sections can be used as separate tests.

Barrow Neurological Institute (BNI)

Unlike the Tinetti score typically used for assessing balance, the Barrow Neurological Institute (BNI) balance scale focuses on Parkinson's disease and addresses issues that result in falls in Parkinson's disease (Lieberman et al., "A quick and easy-to-use clinical scale to assess balance in Parkinson's disease", Journal of Parkinsonism & Restless Legs Syndrome, 2: 67-71, Nov. 30, 2012). Non-limited examples of issues result in falls in Parkinson's disease include, turning, standing on one foot while reaching or walking up or down stairs, and walking in confined spaces. In addition, the BNI balance scale does not duplicate any part of the MDS-UPDRS. As such, the BNI balance scale can be used as a complement to the MDS-UPDRS.

The BNI balance scale comprises five subtest under three major categories for assessing balance and predicting fall. The BNI balance scale incorporates subtests relevant for Parkinson's disease that are related to falls, of which turning and standing on one leg are subtests of the Tinett (item 8 of the balance section) and Berg (items 11 and 14) scales. Patients are assessed for turning, standing on one foot and tandem gait. Patient performance is evaluated by scores with a maximum of 20 points. Details of assessment are described herein.

Patients taking the Turning test are asked to turn 360° and assessed for a score system of 8 points (Table 1). First, patients are asked turn to the right which scores 4 points. Second, patients are asked to turn to the left which scores 4 points. In general, scoring is similar to the Berg, except 4 is normal or baseline on the Berg and 0 is normal or the baseline on the BNI.

TABLE 1

BNI balance scale Turning test

| Score (points) | Description |
|---|---|
| 0 | Accomplished 360° turn in ≤4 seconds (usually in four steps) |
| 1 | Accomplished 360° turn in more than 4 seconds (usually in five or six steps) |
| 2 | Accomplished 360° turn safely but slowly (usually in seven or eight steps) |
| 3 | Accomplished 360° turn, but patient needs close (usually in nine or ten steps) |
| 4 | Needs assistance in turning (or can't turn) |

Patients taking the Standing on one foot test are asked to lift one leg independently and hold for a period of time. First, patients are asked to stand on right foot alone which scores 4 points. Second, patients are asked to stand on left foot alone which scores 4 points. The ability of holding a lifted leg is assessed for a score system of 8 points (Table 2). In general, scoring is similar to the Berg, except 4 is normal or the baseline on the Berg and 0 is normal of the baseline on the BNI.

TABLE 2

BNI balance scale Standing on one foot test

| Score (points) | Description |
|---|---|
| 0 | Able to lift leg independently and hold for more than 10 seconds (with no assistance or support) |
| 1 | Able to lift leg independently and hold for 5-10 seconds (with no assistance or support) |
| 2 | Able to lift leg independently and hold for ≥3 seconds (with no assistance or support) |
| 3 | Able to lift leg independently and hold for less than 3 seconds (may require assistance or support) |
| 4 | Unable to try |

In general, the Tandem gait test requires patients to take ten steps, placing one foot in front of the other, the heel of one foot touching to toe of the other. Patients are assessed for a score system of 4 points (Table 3). A score of 0 point is normal or the baseline.

TABLE 3

BNI balance scale Tandem gait test

| Score (points) | Description |
|---|---|
| 0 | Can walk ten steps, with no missteps (deviation from the midline) |
| 1 | Can walk ten steps, with one misstep |
| 2 | Can walk ten steps, with two, three, or four missteps |
| 3 | Can walk ten steps, with five or more missteps; usually, patient cannot take five or more consecutive steps |
| 4 | Cannot tandem walk |

In some embodiments, improvements of fall-related symptoms are evaluated by utilizing Reason for Fall from the Barrow Neurological Institute (BNI) Falls Evaluation. In some embodiments, improvements of fall-related symptoms are evaluated by utilizing Severity of Fall from the Barrow Neurological Institute (BNI) Falls Evaluation.

In some embodiments, the possibility of fall in a subject with neurological disease is predicted using the Barrow Neurological Institute (BNI) balance scale. As a non-limiting example, patients who have had at least three falls during the month prior to the test are considered fallers and typically score at least 3 points on the BNI Standing on one foot test, at least 3 points on the BNI Turning test, and at least 2 points on the BNI Tandem gait test. As another non-limited example, a patient who reported balance difficulty on the BNI question may also have a MDS-UPDRS posture stability (PS) score at least 2 points, the patient may fall at least three times per month.

In some embodiments, the present disclosure provides methods for evaluating fall-related symptoms in a subject with neurodegenerative disease such as Parkinson's disease or Parkinson's-related disease utilizing the modified BNI Balance Scale constituted of the original UPDRS, the MDS-UPDRS, the Romberg Test, the Turning test, the Standing On One Leg test, and the Tandem gait test. Exemplary tests include Dyskinesias from questions 32-35 from original UPDRS, Response fluctuation from questions 36-39 from original UPDRS, Sleep disturbance from question 40 from original UPDRS, Hoehn & Yahr Staging System (0-V), MDS-UPDRS 132 points, Axial, Midline Part of MDS-UPDRS 24 points, Gait Subtest from MDS-UPDRS, Postural Stability, known as the "pull test", from MDS-UPDRS, and Freezing of Gait (FOG) Subtest from MDS-UPDRS.

In some embodiments, the present disclosure provides methods for evaluating fall-related symptoms in a subject with neurodegenerative disease such as Parkinson's disease or Parkinson's-related disease. In some embodiments, the subject is evaluated by the ability to walk 25 feet or an equivalent of 7.62 meters. The numbers of steps the subject taken to walk 25 feet or an equivalent of 7.62 meters are counted and timed.

In some embodiments, the present disclosure provides methods for evaluating fall-related symptoms in a subject with neurodegenerative disease such as Parkinson's disease or Parkinson's-related disease. In some embodiments, the subject is evaluated for Freezing of Gait in the "on" and "off" state with FOG questions 2.13 from MDS-UPDRS and the MDS-UPDRS subtest of FOG (Espay A J, Fasano A, van Nuenen BFL, "On state freezing of gait in Parkinson's disease: a paradoxical levodopa-induced complication", Neuerology 78:454-457, Jan. 18, 2012).

In some embodiments, the present disclosure provides methods and compositions for treating fall-related symptoms in a subject with Parkinson's disease or Parkinson-related disease comprising administering the compositions to the subject and evaluating the subject's response to the treatment. In some embodiments, the compositions are administered to the subject over a period of 6 months (Fahn S, Elton R L, Members of the UPDRS Development Committee Unified Parkinson's Disease Rating Scale, Fahn S, Marsden C D, Calne D, Goldstein M, "Recent Developments in Parkinson's Disease", Macmillan Healthcare Information Florham Park N.J., pp 3-163, 1988). The effectiveness of the treatment is evaluated by the subject's performance on "on off" testing. In some embodiments, an evaluation is performed every 2 months for up to 6 months. After completion of the six months period, the subject is administered with placebo and is evaluated by "on off" testing 2 months after the cross-over. In some cases, the subject is given two months after the cross-over for treatment re-titration. After the cross-over and re-titration period, the subject's performance on "on off" testing are then evaluated every 2 months for up to 6 months.

In some embodiments, the present disclosure provides methods and compositions for treating fall-related symptoms in a subject with Parkinson's disease or Parkinson-related disease, the methods comprise administering the compositions comprising nicotine or salt thereof to the subject and evaluating the subject's response to the treatment. In some embodiments, a placebo is administered to the subject over a period of 6 months. The effectiveness of the treatment is evaluated by the subject's performance on "on off" testing. In some embodiments, an evaluation is performed every 2 months for up to 6 months. After six months, the subject is administered with the compositions comprising nicotine and salt thereof to serve as his/her own control. Without being limited by any theory, subjects who are on placebo may not be able to tolerate full dose of the present compositions, the subject may undergo another titration period of the treatment. After 2 months of the cross-over and completion of the re-titration, the treatment effectiveness is evaluated by the subject's performance on "on off" testing every 2 months for up to 6 months.

In some embodiments, the present disclosure provides methods and compositions for treating fall-related symptoms in a subject with Parkinson's disease or Parkinson-related disease, the methods comprise administering the compositions comprising nicotine or salt thereof to the subject and evaluating the subject's response to the treatment. In some embodiments, the present compositions are administered to the subject over a period of 6 months. The effectiveness of the treatment is evaluated by the subject's performance on "on off" testing every 2 months for up to 6 months. After six months, the subject is administered with placebo to serve as his/her own control. After 2 months of the cross-over and completion of the re-titration, the treatment effectiveness is evaluated by the subject's performance on "on off" testing every 2 months for up to 6 months.

In some embodiments, the effectiveness of treating fall-related symptoms in a subject with Parkinson's disease or Parkinson-related disease is monitored regularly by evaluating the subject's response to the treatment. The evaluation can be done by a health professional who provides such as preventive, curative, promotional or rehabilitative health care services in a systematic way to people, families or communities. A health professional can be a health care practitioner. Examples of health care practitioner include physicians, dentists, pharmacists, physician assistants, nurses (including advanced practice registered nurses), surgeons, surgeon's assistant, surgical technologist, midwives (obsterics), dietitians, therapists, psychologists, chiropractors, clinical officers, social workers, phlebotomists, physical therapists, respiratory therapists, occupational therapists, audiologists, speech pathologists, optometrists, emergency medical technicians, paramedics, medical laboratory scientists, medical prosthetic technicians, radiographers and a wide variety of other human resources trained to provide some type of health care service. They often work in hospitals, health care centers, and other service delivery points, but also in academic training research, and administration. Some provide care and treatment services for patients in private homes. In some cases, a community health worker can work outside of formal health care institutions. Health care practitioners are commonly grouped into a number of professions: medical (including generalists and specialists); nursing (including various professional titles); Midwifery (Obstetrics); dentistry; and other health professions, including occupational therapy, pharmacy, physical therapy, paramedicine respiratory therapy, radiographer and many other health specialists.

In some embodiments, the effectiveness of the treating fall-related symptoms using the present methods and compositions is evaluated by monitoring the subject's response to the treatment such as the subject's performance on "on off" testing. In some embodiments, the subject is evaluated every 2 months for at least 6 to 14 months. In some embodiments, the subject is evaluated for at least four times over a period of 6 months. For example, the subject is evaluated upon receiving treatment, as known as the initial visit, 2 months after receiving initial treatment; 4 months after receiving initial treatment; and 6 months after receiving initial treatment. In various embodiments, the subject undergoes treatment cross-over and a re-titration period for about 2 months. The subject is evaluated for performance on "on off" testing. After completion of the re-titration period, the subject is then evaluated every 2 months for at least 6. In some embodiments, the subject is evaluated for at least four times over a period of 6 months after the treatment cross-over and re-titration period. For example, the subject is evaluated upon completion of the treatment-cross over and re-titration; 2 months after treatment cross-over and completion of re-titration; 4 months after treatment cross-over and completion of re-titration; and 6 months after treatment cross-over and completion of re-titration.

The present disclosure also provides methods for evaluating fall-related symptoms or predicting recurrent falls in a subject with neurodegenerative disease such as Parkinson's disease or Parkinson-related diseases. In various embodiments, the subject is diagnosed with typical Parkinson's disease. The subject can be male or female between ages of 30 to 83. The subject is in an "on" state of the Hoehn and Yahr Stage II, III, IV and has Montreal Cognitive Assessment (MOCA) score≥26. In some embodiments, the subject has fallen at least once in past year. The subject is also on stable dose of levodopa, dopamine agonist, amantadine, and/or monoamine oxidase B inhibitor.

In some embodiments, a subject with neurodegenerative disease and fall-related symptoms can be treated with the present methods and compositions. The subject may not have atypical Parkinson's disease, or disorders that while infrequent, result in a high number of falls especially early in the disease. These disorders include Progressive Supranuclear Palsy (PSP), Multiple System Atrophy (MSA), Primary Freezing of Gait (PFG), and Corticobasiler Degeneration. The subject may not have Parkinson's disease and dementia. Excluded are also subjects who are legally blind, subjects who have major orthopedic problems of their hips or knees, patients who needed hip or knee replacements. Although orthostatic hypotension, reflecting involvement of the autonomic nervous system (ANS), can be part of Parkinson's disease, it can also result from the use of anti-hypertensives, diuretics, selected anti-depressants, and dehydration. It is often difficult to determine if a fall from orthostatic hypotension resulted from impairment of the ANS or from drugs and dehydration, subjects with orthostatic hypotension are excluded. Also excluded are subjects with a history of schizophrenia, schizo-affective disorder, bipolar disorder, hallucinations, psychoses or delusions, subjects who had deep brain stimulation (DBS) intervention, and/or subjects with a history of recent stroke or myocardial infarction.

In one aspect, the present disclosure provides for a method of treating cognitive-related symptoms in a subject with neurodegenerative disease comprising administering nicotine or salt thereof to the subject. In some embodiments, the nicotine and salt thereof is administered in dosage form. The administration of nicotine or salt thereof can reduce cognitive impairment in a subject with a neurodegenerative disease such as Parkinson's disease, schizophrenia, mild cognitive impairment, Alzheimer's Disease, vascular cognitive impairment, Subcortical Ischaemic Vascular Dementia, Frontotemporal Mild Cognitive Impairment, and Frontotemporal Dementia. In some embodiments, the subject has typical Parkinson's disease. In some embodiments, the subject is diagnosed for Parkinson's disease for at least 5 years. In some embodiments, the subject is on dopaminergic agent treatment. In some embodiments, the subject has fallen or recurrent falls in past year.

In various embodiments, the present disclosure provides for a method of treating cognitive-related symptoms in a subject with neurodegenerative disease comprising administering a composition comprising a nicotinic receptor modulator to the subject. In some embodiments, the composition is administered in dosage form. In some embodiments, the nicotinic receptor modulator is a nicotinic receptor agonist or antagonist. The administration of the composition can reduce cognitive impairment in a subject with neurodegenerative diseases such as Parkinson's disease, schizophrenia, mild cognitive impairment, Alzheimer's Disease, vascular cognitive impairment, Subcortical Ischaemic Vascular Dementia, Frontotemporal Mild Cognitive Impairment, and Frontotemporal Dementia. In some embodiments, the subject has typical Parkinson's disease.

In some embodiments, the present disclosure provides for a method of treating cognitive-related symptoms in a subject with Parkinson's disease, schizophrenia, mild cognitive impairment, Alzheimer's Disease, vascular cognitive impairment, Subcortical Ischaemic Vascular Dementia, Frontotemporal Mild Cognitive Impairment, or Frontotemporal Dementia comprising administering nicotine or salt thereof to the subject. The administration of nicotine or salt thereof can reduce cognitive impairments. In some embodiments, the subject is on dopaminergic agent treatment. Non limiting examples of dopaminergic agents includes levodopa, bromocriptine, pergolide, pramipexole, cabergoline, ropinorole, apomorphine, carbidopa, dopamine agonists, monoamine oxidase type B inhibitors, amantadine or a combination thereof. In some embodiments, the subject is on levodopa, carbidopa, dopamine agonist, amantadine, monoamine oxidase B inhibitor, or combination thereof.

In various embodiments, disclosed herein are methods and compositions for reducing cognitive-related symptoms in a subject with Parkinson's disease, schizophrenia, mild cognitive impairment, Alzheimer's Disease, vascular cognitive impairment, Subcortical Ischaemic Vascular Dementia, Frontotemporal Mild Cognitive Impairment, or Frontotemporal Dementia and is on dopaminergic agent treatment, e.g. levodopa/carbidopa, the methods and compositions comprising administering nicotine or salt thereof to the subject. The administration of nicotine or salt thereof in combination with a dopaminergic agent can reduce cognitive-related symptoms. In various embodiments, utilization of the disclosed methods and compositions reduces side effects related to dopaminergic agent treatment, for example, reducing dyskinesia and improving response fluctuations: "wearing off and of off".

Pharmaceutical Composition

In some embodiments, the present disclosure provides for a pharmaceutical composition comprising nicotine or salt thereof for treating fall-related and cognitive-related symptoms in a subject with neurodegenerative disease. In some embodiments, the composition can be any nicotine-containing composition described herein. In some embodiments, the pharmaceutical composition is formulated in dosage form for administration. In a related embodiment, the composition comprises a nicotinic receptor modulator, such as nicotine or salt thereof described herein. In some embodiments, the nicotinic receptor modulator is a nicotinic receptor agonist.

In a related embodiment, the dosage form is a pharmaceutical composition comprising a pharmaceutically acceptable carrier, examples of which are described herein.

Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in water emulsion, or a water-in-oil liquid emulsion. Such dosage forms can be prepared by any of the methods of pharmacy, but all methods include the step of bringing the active ingredient into association with the carrier, which constitutes one or more necessary ingredients.

In some embodiments, the composition comprises nicotine or salt thereof at the amount of between about 0.001 to 1000 mg, 0.01 to 100 mg, 0.1 to 200 mg, 3 to 200 mg, 5 to 500 mg, 10 to 100 mg, 10 to 1000 mg, 50 to 200 mg, or 100 to 1000 mg of nicotine or salt thereof. In some embodiments, the pharmaceutical composition comprises about or more than about 0.001 mg, 0.0.1 mg, 0.1 mg, 0.5 mg, 1 mg, 2 mg, 3 mg, 4 mg, 5 mg, 6 mg, 7 mg, 8 mg, 9 mg, 10 mg, 15 mg, 18 mg, 20 mg, 24 mg, 25 mg, 50 mg, 100 mg, 200 mg, 500 mg, 1000 mg, or more of nicotine or salt thereof.

In some embodiments, the composition comprises nicotine or salt thereof at the amount of between about 0.1 mg to 5 mg, between about 1 mg to 3 mg, between about 2 mg to 20 mg, between about 10 mg to 25 mg, between about 15 mg to 50 mg, between about 20 mg to 200 mg, between about 100 mg to 500 mg, between about 150 mg to 1000 mg. In some embodiments, the amount of nicotine or salt thereof is between about 1 mg to 24 mg. In some embodiments, the amount of nicotine or salt thereof is about 0.001 mg, about 0.01 mg, about 0.1 mg, about 1 mg about 2 mg, about 3 mg, about 4 mg, about 5 mg, about 6 mg, about 7 mg, about 8 mg, about 9 mg, about 10 mg, about 12 mg, about 14 mg, about 16 mg, about 18 mg, about 20 mg, about 25 mg, about 30 mg, about 50 mg, about 100 mg, about 150 mg, about 200 mg, about 500 mg, about 1000 mg. In some embodiments, the amount of nicotine or salt thereof is less than about 0.001 mg, less than about 0.01 mg, less than about 0.1 mg, less than about 1 mg, less than about 2 mg, less than about 3 mg, less than about 4 mg, less than about 5 mg, less than about 6 mg, less than about 7 mg, less than about 8 mg, less than about 9 mg, less than about 10 mg, less than about 12 mg, less than about 14 mg, less than about 16 mg, less than about 18 mg, less than about 20 mg, less than about 25 mg, less than about 30 mg, less than about 50 mg, less than about 100 mg, less than about 150 mg, less than about 200 mg, less than about 500 mg, less than about 1000 mg. In some embodiments, the nicotine or salt thereof is present at about 1 mg. In some embodiments, the nicotine or salt thereof is present at about 2 mg. In some embodiments, the nicotine or salt thereof is present at about 4 mg. In some embodiments, the nicotine or salt thereof is present at about 6 mg.

Formulation

In some embodiments, the composition is formulated for administering to a subject in need thereof wherein the composition comprises nicotine or salt thereof in an amount effective to reduce fall-related symptoms. The treatment comprises reducing fall-related symptoms such as reducing fall frequency, reducing injuries related to fall, reducing severity of injuries related to fall, and improving balance, posture stability and gait. The treatment may also comprise reducing cognitive-related symptoms. The composition is formulated in dosage form. In some embodiments, the composition is formulated in dosage form comprising a nicotinic receptor modulator such as a nicotinic receptor agonist. In various embodiments, the composition is formulated for administering in combination with a dopaminergic agent, e.g. levodopa, carbidopa, dopamine agonists, amantadine, and monoamine oxidase B inhibitor, or combination thereof.

In various embodiments, the composition comprises between about 00.001 to 1000 mg, 0.01 to 100 mg, 0.1 to 200 mg, 3 to 200 mg, 5 to 500 mg, 10 to 100 mg, 10 to 1000 mg, 50 to 200 mg, or 100 to 1000 mg of nicotine or salt thereof. In some embodiments, the pharmaceutical composition comprises about or more than about 0.001 mg, 0.0.1 mg, 0.1 mg, 0.5 mg, 1 mg, 2 mg, 3 mg, 4 mg, 5 mg, 6 mg, 7 mg, 8 mg, 9 mg, 10 mg, 15 mg, 20 mg, 25 mg, 50 mg, 2.0 mg, 100 mg, 200 mg, 500 mg, 1000 mg, or more of nicotine or salt thereof. In some embodiments, the pharmaceutical composition comprises at least about 1 mg of nicotine or salt thereof. In some embodiments, the pharmaceutical composition comprises at least about 2 mg of nicotine or salt thereof. In some embodiments, the pharmaceutical composition comprises at least about 4 mg of nicotine or salt thereof. In some embodiments, the pharmaceutical composition comprises at least about 6 mg of nicotine or salt thereof. In some embodiments, the pharmaceutical composition comprises an amount between about 1-10 mg of nicotine or salt thereof.

In some embodiments, the composition is formulated to provide a therapeutically effective amount of a compound of the present disclosure as the active ingredient, or a pharmaceutically acceptable salt, ester, prodrug, solvate, hydrate or derivative thereof. Where desired, the pharmaceutical composition contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject composition disclosed herein can be formulated for administration via oral, intravenous injection, and/or topical. In some embodiments, the disclosed pharmaceutical composition is formulated for topical administration.

In some embodiments, the composition further comprises a carrier compatible with intravenous, intraarterial, oral, parenteral, buccal, topical, transdermal, rectal, intramuscular, subcutaneous, intraosseous, transmucosal, inhalation, or intraperitoneal administration.

In some embodiments, the composition is formulated as a unit dosage in liquid, gel, semi-liquid, semi-solid, and/or solid form.

In some embodiments, the composition is formulated as a topical cream.

In some embodiments, the composition is formulated in a food. In some embodiments, the composition is formulated in a beverage. In some embodiments, the composition is formulated in a dietary supplement.

Pharmaceutical Composition for Oral Administration

In some embodiments, the disclosure provides a pharmaceutical composition for oral administration containing a nicotinic receptor modulator such as nicotine or salt thereof, and a pharmaceutical excipient suitable for oral administration. The composition may be in the form of a solid, liquid, gel, semi-liquid, or semi-solid. In some embodiments, the composition further comprises a second agent.

Pharmaceutical composition of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, which typically include the step of bringing the active ingredient into association with the carrier. In general, the composition are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical composition and dosage forms of the disclosure can be prepared using anhydrous or low moisture containing ingredients and low moisture or low humidity conditions. Pharmaceutical composition and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous composition may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

In various embodiments, the present disclosure provides for a dosage form includes capsules or tablets comprising an effective amount of nicotine or salt thereof for treatment of fall-related symptoms in a subject with neurodegenerative disease such as Parkinson's disease and Parkinson-related diseases. The capsules and tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

In various embodiments, the dosage form of the present disclosure is a capsule. In various embodiments, the dosage form is formulated for pulsatile release. In some embodiments, the capsule comprises a powder comprising nicotine for providing said first release peak upon administration to a patient, and said capsule further comprises beads comprising nicotine for providing said second, third, and fourth release peaks upon administration to a patient. Beads may be coated with immediate release coatings or delayed release coatings. Beads are selected from the group consisting of enteric-coated beads, erodible-matrix beads, wax-coated beads, ethylcellulose-coated beads, silicone elastomer coated beads, and combinations thereof. In various embodiments, said capsule comprises a water-swellable matrix to provide a gastroretentive formulation with repeated pulsatile release in the stomach. A water-swellable matrix may comprise polyethylene oxide, hydroxypropylmethylcellulose, and combinations thereof. The pulsatile release formulation may provide for a 1 ng/mL to 20 ng/ml plasma concentration of nicotine about 2 h after administration of a dopaminergic agent.

In some embodiments, the dosage form is a tablet. In various embodiments, the dosage form is formulated for pulsatile release. Tablets comprising at least one coating and a core, wherein an outermost coating comprises nicotine for the first release peak, and said core comprises nicotine for the second, third, and fourth release peaks, are encompassed. In various embodiments, the coating is selected from an enteric coating, an erodible-matrix coating, a wax coating, an ethylcellulose coating, a silicone elastomer coating, and combinations thereof.

In some embodiments, the disclosure includes a multi-layer tablet comprising an immediate release layer and pulsatile release layer(s). In some embodiments, the immediate release layer comprises nicotine or a metabolite. In some embodiments, each pulsatile release layer comprises nicotine or a metabolite. In some embodiments, the immediate release layer and each pulsatile release layer comprise nicotine or a metabolite.

The tablet core of the dosage form of the present invention can comprise a matrix of a drug and a water soluble polymer, suitable for pulsatile release upon entry and following exit of the tablet from the acidic environment of the stomach and dissolution of the coating upon entry into the higher pH environment of the intestine.

The tablet core can be prepared by conventional dry granulation methods without using a solvent. Typically, the enteric coating is applied using a conventional process known in the art.

In some embodiments, the dosage form comprises an enteric coating comprising an enteric polymer. Suitable enteric polymers include, but are not limited to, methacrylic acid/methacrylic acid ester copolymer, a methacrylic acid/acrylic acid ester copolymer, cellulose acetate phthalate, hydroxypropyl methylcellulose pthalate, hydroxypropyl methyl cellulose acetate succinate, cellulose acetate trimellitate, and polyvinyl acetate phthalate.

Enteric polymers suitable for use in the present disclosure include, but are not limited to polyacrylate copolymers such as methacrylic acid/methacrylic acid ester copolymers or methacrylic acid/acrylic acid ester copolymers, such as USP/NF, Types A, B, or C, which are available from Rohm GmbH under the brand name Eudragit™; cellulose derivatives, such as cellulose acetate phthalate, hydroxypropyl methylcellulose pthalate, hydroxypropyl methyl cellulose acetate succinate, and cellulose acetate trimellitate; and polyvinyl acetate phthalate, such as is available from Colorcon, under the brand name SURETERIC®, and the like. In some embodiments, the enteric polymer is a polyvinyl acetate phtalate.

Suitable water soluble pore-forming agents for use in the enteric coating in the dosage forms of the present disclosure include, but are not limited to, povidone K 30, polyvinyl alcohol, cellulose derivatives such as hydroxypropyl cellulose, hydroxypropyl methyl cellulose, methyl cellulose or sodium carboxymethylcellulose; sucrose; xylitol, sorbitol, mannitol, maltose, xylose, glucose, potassium chloride, sodium chloride, polysorbate 80, polyethylene glycol, propylene glycol, sodium citrate, or combinations of any of the above. The pore-forming agent preferably comprises hydroxypropyl methyl cellulose.

The composition of the enteric coating is preferably designed to ensure adherence of the coating to the tablet core. Methods for selection of coating compositions that adhere to compressed tablets are known. See, for example, Pharmaceutical Dosage Forms: Tablets, 2nd ed., vol. 1, Lieberman et al., ed. (Marcel Dekker, Inc.; New York, N.Y.; 1989), pp. 266-271, incorporated herein by reference. Additionally, the cores can be subcoated prior to coating with an enteric coating. The subcoat can function; to provide that pores in the core are filled in prior to coating with an enteric coat to insure against coating failure. The sub-coat can consist of any film forming formulation examples include Opadry (Colorcon), Opadry II (Colorcon), AMT (Colorcon) and HPMC.

The enteric coating can be about 3% to about 10% by weight of the dosage form of the present invention. In some cases, the enteric coating can be about 4%, 5%, 6%, 7%, 8%, 9%, 10%, 11%, 12%, 13%, 14%, 15%, 16%, 17%, 18%, 19%, or 20% by weight of the dosage form of the present disclosure.

In some embodiments, the tablet core of a dosage form of the disclosure comprises at least one hydrophilic polymer. Suitable hydrophilic polymers include, but are not limited to, hydroxypropyl methylcellulose (hereinafter, "HPMC"), hydroxypropylcellulose, or other water soluble or swellable polymers such as sodium carboxymethyl cellulose, xanthan gum, acacia, tragacanth gum, guar gum, karaya gum, alginates, gelatin, and albumin The hydrophilic polymers can be present in amounts ranging from about 5% to about 95% by weight of the system. In some embodiments, the hydrophilic polymers are selected from the group consisting of cellulose ethers, such as hydroxypropylmethylcellulose, hydroxypropylcellulose, methylcellulose, and mixtures thereof.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Injection

In some embodiments, the disclosure provides a pharmaceutical composition for injection containing a nicotinic receptor modulator such as nicotine or salt thereof and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation

Composition for inhalation or insufflation include solutions and suspensions in pharmaceutically acceptable, aqueous or organic solvents, or mixtures thereof, and powders. The liquid or solid composition may contain suitable pharmaceutically acceptable excipients as described supra. Preferably the composition are administered by the oral or nasal respiratory route for local or systemic effect. Composition in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder composition may be administered, preferably orally or nasally, from devices that deliver the formulation in an appropriate manner.

Other Pharmaceutical Composition

Pharmaceutical composition may also be prepared from composition described herein and one or more pharmaceutically acceptable excipients suitable for sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Food

In some aspects, the disclosed pharmaceutical composition is a food composition comprises a food carrier. In some embodiments, the food composition comprises nicotine or salt thereof between about 0.001 to 1000 mg, 0.01 to 100 mg, 0.1 to 200 mg, 3 to 200 mg, 5 to 500 mg, 10 to 100 mg, 10 to 1000 mg, 50 to 200 mg, or 100 to 1000 mg of nicotine or salt thereof. In some embodiments, the food composition comprises about or more than about 0.001 mg, 0.0.1 mg, 0.1 mg, 0.5 mg, 1 mg, 2 mg, 3 mg, 4 mg, 5 mg, 6 mg, 7 mg, 8 mg, 9 mg, 10 mg, 15 mg, 20 mg, 25 mg, 50 mg, 100 mg, 200 mg, 500 mg, 1000 mg, or more of nicotine or salt thereof. In some embodiments, the food composition comprises between about 0.01 to 10 mg of nicotine or salt thereof. In some embodiments, the food composition comprises at least about 1 mg of nicotine or salt thereof. In some embodiments, the food composition comprises at least about 2 mg of nicotine or salt thereof. In some embodiments, the food composition comprises at least about 3 mg of nicotine or salt thereof. In some embodiments, the food composition comprises at least about 4 mg of nicotine or salt thereof. In some embodiments, the food composition comprises at least about 5 mg of nicotine or salt thereof. In some embodiments, the food composition comprises at least about 6 mg of nicotine or salt thereof.

Packaging of the disclosed food composition can be achieved with any known skill in the art. Without being bound by any theory, the disclosed food composition may be packaged as a beverage, a solid food, and/or a semi-solid food. In some cases, the disclosed food composition is packaged as a food product such as one or more forms in the group consisting of a snack bar, cereal product, bakery product, and dairy product.

Pharmaceutical Components

Dosage forms of the present disclosure may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Diluents can be incorporated into the tablet core of a dosage form. Dosage forms of the invention, preferably a tablet core matrix, optionally comprise one or more pharmaceutically acceptable diluents as excipients. Non-limiting examples of suitable diluents include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of amorphous cellulose (e.g., Rexcel™) and powdered cellulose; calcium carbonate; glycine; bentonite; polyvinylpyrrolidone; and the like. Such diluents, if present, constitute in total about 5% to about 99%.

In another embodiment of the disclosure, a gastric retained dosage form of nicotine or salt thereof is provided. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107, and U.S. Pat. No. 8,192,756, the contents of each of which are incorporated by reference in their entirety.

In yet another embodiment, a bi, tri, or quad-layer tablet releases nicotine or salt thereof to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

In some embodiments, nicotine is orally administered using an orally disintegrating tablet. Examples of orally disintegrating tablets are known, such as disclosed in U.S. Pat. Nos. 7,282,217; 7,229,641; 6,368,625; 6,365,182; 6,221,392; and 6,024,981.

Another embodiment of the disclosure uses a gastric retained swellable tablet having a matrix comprised of polyethylene oxide and hydroxypropylmethylcellulose. Further details may be found in Gusler, et al. "Optimal Polymer Mixtures for Gastric Retentive Tablets," granted as U.S. Pat. No. 6,723,340, the disclosure of which is incorporated herein by reference.

Pharmaceutically acceptable carriers for therapeutic use are well known in the pharmaceutical art, and are described, for example, in Remington's Pharmaceutical Sciences, Mack Publishing Co. (A. R. Gennaro edit., 1985). Preservatives, stabilizers, dyes and other ancillary agents may be provided in the pharmaceutical composition. For example, sodium benzoate, sorbic acid and esters of p-hydroxybenzoic acid may be added as preservatives. In addition, antioxidants and suspending agents may be used.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate,

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: NP002 in Combination With Dopaminergic Drugs for Treatment of Fall-Related Symptoms and Improvement of Posture Stability A total of 20 patients with Parkinson disease, for five years or more, who have impaired postural stability (balance) and have fallen are enrolled in an interventional study. The patients are randomly assigned to NP002 or an identical placebo in addition to their regular PD dopaminergic medication. Major entry criteria are as follows: 1) clinical diagnosis of typical Parkinson's disease, 2) male or female between ages of 30 to 83, 3) Hoehn and Yahr Stage II-IV while in an "on" state, 4) has had fallen more than once in past year, 5) has Montreal Cognitive Assessment (MOCA) score$\geq$21, 6) be stable dose of levodopa/caribodpa. They may be on additional dopaminergic drugs including dopamine agonists and/or monoamine type B oxidase inhibitors or amantadine. See FIG. 1.

Patients with the following disorders or symptoms are excluded from enrollment:

Excluded are patients with atypical Parkinson, disorders that while infrequent, result in a high number of falls especially early in the disease. These disorders include Progressive Supranuclear Palsy (PSP), Multiple System Atrophy (MSA), Primary Freezing of Gait (PFG), and Corticobasiler Degeneration.

Excluded are patients with dementia MOCA$\geq$21. Although dementia is part of PD and can be a risk for falling, more than half of our patients with PD and dementia are without a care-giver for at least 4 hours and we are uncertain if they report all their falls.

Excluded are patients who are legally blind.

Excluded are patients with major orthopedic problems of their hips or knees, patients who needed hip or knee replacements.

Excluded are patients with orthostatic hypotension. Although orthostatic hypotension, reflecting involvement of the autonomic nervous system (ANS), can be part of PD, it can also result from the use of anti-hypertensives, diuretics, selected anti-depressants, and dehydration. As we often cannot determine if a fall from orthostatic hypotension resulted from impairment of the ANS or from drugs and dehydration we exclude such persons.

Excluded are patients with a history of schizophrenia, schizo-affective disorder, bipolar disorder Excluded are patients with hallucinations, psychoses or delusions.

Excluded are patients that had deep brain stimulation (DBS) Intervention.

Excluded are patients with a history of recent stroke or myocardial infarction.

Figure 2:
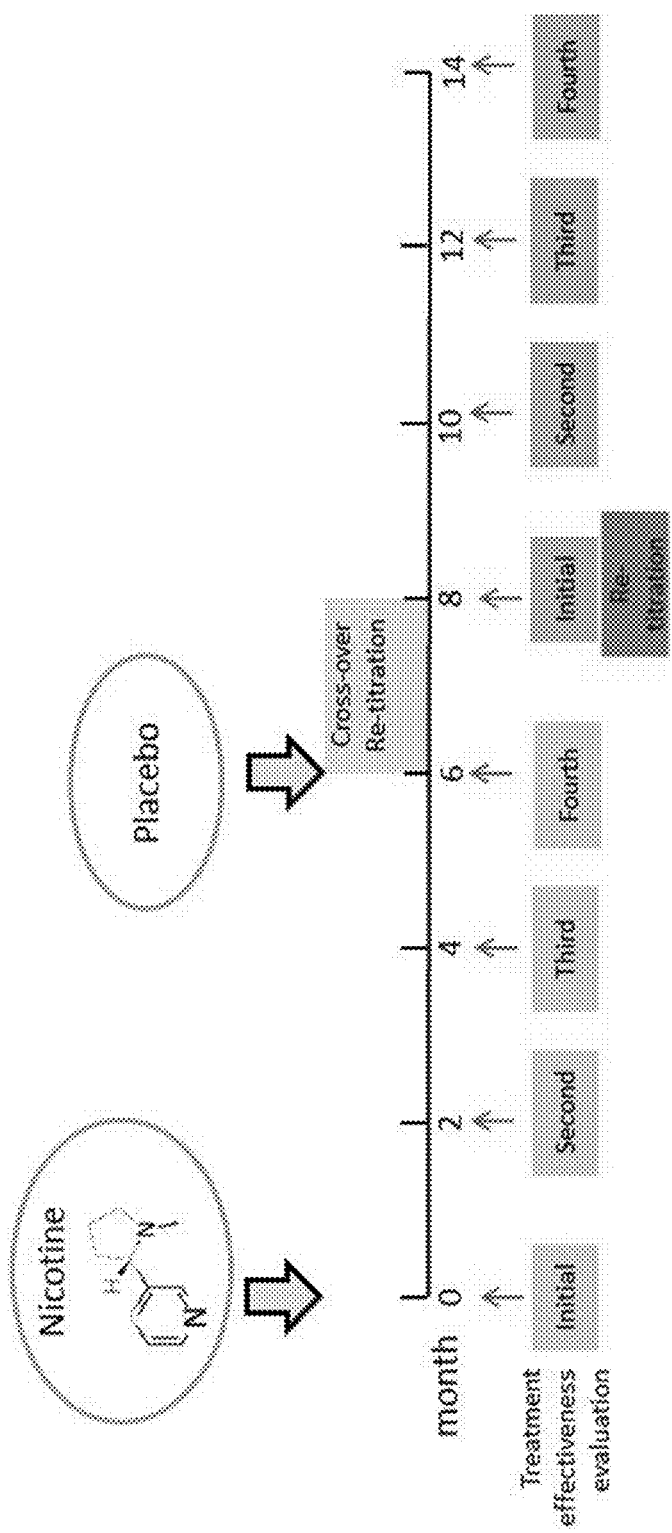
FIG. 2 illustrates a timeline of evaluating effectiveness of nicotine or salt thereof in treating fall-related symptoms in subjects with Parkinson's disease.

The study consists of 3 phases: a treatment period of 6 months, a treatment re-titration period of 2 months, a crossover treatment period of 6 months. See FIG. 2. Subjects are randomly assigned to receive either NP002 comprising nicotine or salt thereof, or placebo. All patients are on stable levodopa/carbidopa treatment. Patients may have additional dopaminergic drugs including dopamine agonists and/or monoamine type B oxidase inhibitors or amantadine. Patients are evaluated in an "off" period, 16 hours off levodopa/carbidopa and then in an "on" period, one hour after usual morning dose of levodopa/carbidopa. NP002 or placebo in a 1:1 ratio is administered as an oral capsule 4 times a day in a blinded fashion for 6 months, and then a crossover for another 6 months. In between the treatment regimes, subjects are given a treatment re-titration period for 2 months. Dosing begins at 1 mg every 6 hours, total daily dose is 4 mg and escalated upward at 2 week intervals as follows:

Two mg every 6 hours total daily dose 8 mg for 2 weeks.
Four mg every 6 hours total daily dose 16 mg for 2 weeks.
Six mg every 6 hours total daily dose 24 mg for 2 weeks.

Patients are maintained on this dose for the duration of the next few weeks of the study until the cross-over. Because patients who are on placebo have not been exposed to nicotine, the original escalation schedule is repeated.

Safety is assessed by incidences of adverse experiences (AE), clinical laboratory tests, serum cotinine, ECG and vital signs. Impulsive symptoms are assessed using the Jay Modified Minnesota Impulsive Disorders Interview (JayMidi). Withdrawal symptoms are evaluated using the Minnesota Nicotine Withdrawal Scale (MNWS-R).

Efficacy is assessed using the Unified Parkinson's Disease Rating Scale (UPDRS), Barrow Neurological Institute (BNI) Falls Evaluation, Hoehn & Yahr Staging System, Romberg test, turning test, standing on one leg, tandem gait, step length and velocity, Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS).

Improvements of axial UPDRS subtests in either "on" or "off" or both "on or off" periods, including improvement in Gait subtest, Pull test, and FOG subtests, improvement in turning, in standing on one leg, in tandem gait, in step length and velocity, improvement in quantitative tests.

All or most of these patients may have response fluctuations: "wearing off" and/or "on off" Some of these patients may have freezing of gait (FOG).

Example 2: NP002 in Combination with Dopaminergic Drugs for Reducing Dyskinesia and Improving Response Fluctuations Example 1 is repeated. This is a Phase II single center, randomized, double-blind, placebo controlled, efficacy, safety and tolerability study. A total of 20 male and female patients with typical Parkinson's disease with recurrent falls are included. The study consists of an initial evaluation, evaluation every 2 months for 6 months, a cross-over, and then an evaluation every 2 months for 6 months.

Example 3: Effect of NC001, a Central Cholinergic Agonist on Gait, Postural Stability and Falls in Parkinson Disease Falls and postural instability (impaired balance) are major problems in Parkinson disease (PD) and are largely unresponsive to dopaminergic replacement. Central cholinergic neurons and nicotinic receptors in the striatum, the brainstem (pedunculopontine nucleus) and thalamus mediate postural stability. There is growing evidence that central cholinomimetic drugs may improve postural stability and reduce falls. A major problem is the relative lack of effective central cholinomimetic drugs. A secondary problem is the lack of effective means of continuously monitoring locomotion (gait) and postural stability in PD patients who are at risk for falling. Such continuous monitoring, utilizing wearable Inertial Measuring Units, IMUs, combined with traditional means of evaluating gait and postural stability (motor part of the Unified Parkinson Disease Rating Scale, UPDRS, tests of balance, motor control time (MCT), and postural perturbations utilizing a Neurocom System, offer the best means of documenting and quantifying the effects of drugs on improving postural stability and reducing falls.

NC001 ((formerly NP002), Nicotine Bitartrate) a central cholinergic agonist was shown to improve gait and balance in a small but well conducted study on the effect of a central cholinomimetic drug on dyskinesias. From the study it was unclear if the improvement in gait and balance was secondary to a direct effect on gait and postural stability or from a secondary effect: a reduction in dyskinesias. Several other studies suggest that central cholinomimetic drugs may improve postural stability and reduce falls. A problem is that these drugs, unlike NC001, do not readily penetrate the central nervous system (CNS).

Weakness of Study: Nicotine is a highly potent central cholinergic agonist and may improve postural stability and reduce falls. The population chosen, however, may have disease too advanced to be improved: perhaps the intervention should be earlier, in patients with less advanced PD. Adverse effects of nicotine may be of concern in older patients with advanced PD.

Falling, injuries related to falling, and fear of falling pose a major burden to PD patients. Falls are a major cause of hospitalization for PD patients. Annual incidence of falls range from 50% to 70% in patients with advanced PD and are a major cause of disability resulting in loss of independence.

NC001, nicotine bitartrate, is a known central cholinergic agonist. Nicotine (in cigarettes) has been associated with a reduced risk of developing PD (after factoring in the adverse effects of nicotine on the cardio-vascular system and on the development of cancer). Whether this is from a neuroprotective effect of nicotine on CNS cholinergic neurons or from a therapeutic effect on gait and postural stability is unknown. Central cholinergic neurons mediating gait and postural stability have been identified in the striatum, pedunculopontine nucleus and in the thalamus. Nicotine, administered orally, is an effective cholinomimetic agonist. Gait speed, postural stability, and reduction of falls have been associated with a reduction in degeneration of cholinergic neurons in the CNS. Available cholinomimetic agents with relatively poor CNS penetration (rivastigmine, donepezil) have, nonetheless had a mild, but variable effect on reducing falls.

The primary objective of the study is to determine whether treatment with NC001 versus placebo in addition to dopaminergic drugs improve postural stability and reduce falls and/or severity of falls in PD patients. This is achieved by demonstrating improvement of selected MDS-UPDRS subtests in either "on" or "off" or both periods. The subtests include the "Gait" and "Pull test." The objective is achieved by demonstrating improvement on subtests such as "Standing on One Leg" and Step Length.

Since there are limitations to the above semi-quantitative tests they are complemented by tests of motor control time (MCT) and postural perturbations utilizing a Neurocom system.

The PD patient population chosen has advanced PD, is on levodopa, and is having "wearing off." Some of these patients may have dyskinesias. They are evaluated in an "off" period, 16 hours without levodopa, at a time when they are without dyskinesias. This is important as we want to be able to see the effects of NC001 on gait and postural stability in the absence of dyskinesias. Patients are then evaluated in an "on" period an hour after they receive their usual daily dose of levodopa.

A problem with such evaluations is that they capture the patient's gait and postural stability, including phenomena such as freezing of gait (FOG), a risk factor for falls, over a short period of time. The evaluation of patients in their "on" and "off" period is complemented by continuous monitoring, utilizing wearable Inertial Measuring Units incorporating accelerometers and gravitometers that monitor gait, FOG, postural stability, and falls. Patients are monitored for up to three days with the IMUs. The monitoring is supplemented by dairies kept by the patient.

The study population includes 20 patients with PD who have had PD for at least five years, who have impaired postural stability, who have fallen at least twice in a year, who are on levodopa, who are having "wearing off" (and who usually fall when they are "off"). Half of the patients are randomized to NC001 and half to placebo. The group is treated for six months and then they are switched.

A secondary objective of the study is to evaluate the efficacy of adding NC001 versus placebo in reducing dyskinesias and in improving response fluctuations: "wearing off."

Because of the effects of impaired cognition (dementia) on gait, postural stability, and falls we exclude patients with dementia. At a later time we will study NC001 in patients with dementia who fall.

Parkinson disease is characterized by a loss of nigrostriatal dopamine neurons. Nicotine receptors are located in the striatum as well as the pedunculopontine nucleus and various thalamic nuclei. NC001 or placebo in a 1:1 ratio is administered as an oral capsule four times a day in a blinded fashion for six months. Then, after a crossover, for another six months. In the double blind treatment phase dosing is begun at one mg every six hours to a total daily dose of 4 mg. Then the dose is escalated to a total dose of 24 mg per day.

Example 4: Formulations and Production of GMP Material for a Human Clinical Trial The primary formulation target is to develop a 2 pulse formulation that will deliver an immediate-release bolus at time zero, and deliver a second immediate-release bolus of nicotine approximately six hours after ingestion. This 2 pulse dosage form is intended to be administered 2 times in a day spaced 12 hours apart (q12 hr) in order to mimic the PK profile previously evaluated in the Phase 2 studies. There have been a number of formulation approaches that have achieved a bolus release of drug after an extended lag time after oral ingestion, and these approaches are characterized in the literature (Sharma, G. S. et al., 2010). This approach has been used successfully in many drug development programs, and there are approved drug products on the market in the US and the rest of the world that are designed as multiparticulate dosage forms, including Zohydro E R, Adderall X R, Ritalin L A, Moxatag, Carbatrol, Equetro and others. In each case, the specific formulation was tailored to the molecule and to the target pharmacokinetic profile for the drug product. This formulation development program focuses on a multiparticulate immediate-release dosage form that is coated with a semi-permeable membrane. This membrane, once hydrated, allows water flow into the dosage form, but does not allow drug to leak out through the membrane. In addition to the active drug substance, the core of the dosage form may contain organic salts, swellable materials, or superdisintegrants that provide the driving force for the water uptake and help dictate the timing of the programmed drug release.

A 15% solution of nicotine is prepared including hypromellose (HPMC) as a binder and succinic acid as the organic acid modifier. This solution is coated onto nonpareil seeds using a fluid bed dryer fitted with a precision coater apparatus until a 20% solids weight gain is achieved on the pellets. The final drug layer formulation contains nicotine, HPMC, and succinic acid in a 5:3.5:1.5 ratios. If necessary, alternative binders may be used in order to improve the quality of the adherence of the drug layer to the nonpareil seed. This core drug-loaded pellet may be coated with an immediate release polymer such as Opadry for aesthetics and used as the immediate release component of the composite dosage form. For the delayed release pellets, a separate population of the core drug loaded pellets is further coated with a separate functional polymer film coat. An aqueous solution of Eudragit RS is prepared with triethyl citrate as the plasticizer and talc functioning as the antitack agent in a 6:1:3 ratios. This solution is coated onto the drug loaded pellets using a fluid bed dryer fitted with a precision coater to total solids weight gain of approximately 70%. The optimum weight gain is determined experimentally by using in vitro dissolution as the feedback mechanism. Alternative polymer materials such as Eudragit RL may also be included in the polymer film coating formulation to modify the lag time or release rate of the nicotine from the delayed release pellets.

Length of the lag time and strength of the drug release may be tailored based on coating formulation and coat weight gain. Initial formulation development experiments are conducted on small, laboratory scale equipment and batch sizes (10-50 g/batch). These batches are manufactured at the laboratory or benchtop scale, and manufacturing instructions and conditions are documented in a notebook. This material is suitable for in vitro testing but not for clinical use.

Formulation prototypes are evaluated using a standard drug product testing approach, including evaluation of drug product content assay, impurities evaluation, uniformity of dosage units, and in vitro drug nicotine release rate evaluation. An important tool for evaluation of solid, oral dosage forms, including modified-release dosage forms, is in vitro dissolution testing. Dissolution testing is the industry standard for evaluation of the release rate for all solid, oral dosage forms, both immediate-release and modified-release. It is used during development to assess the performance of the prototype formulations, during routine commercial batch release to ensure consistency for product that is marketed to patients, and can be used to predict the in vivo performance with an in vivo/in vitro correlation (IVIVC). Once an IVIVC has been established, the pharmacokinetic profile of the dosage form can be predicted by evaluation of the in vitro release rate. The dissolution test conditions can be tailored in order to mimic conditions in the gastrointestinal tract, and provide insight and sometime predict the in vivo drug release rate. Specifically, the immediate release formulations are evaluated in dilute HCl, with a pH of 1.1, to mimic the fasted stomach conditions, and a pH 4.5 buffer to mimic the fed stomach conditions. Delayed release formulations can be challenged in dilute HCl media, with a change to pH 6.8 media to mimic the movement from the stomach to the small intestine.

The in vitro evaluation of the immediate release pulse and the delayed release components of the dosage form are evaluated in a dissolution bath with paddles rotating at 50 RPM at 37° C. The media that is employed is a dilute HCl solution at pH 1.1 to simulate the condition in the gastric cavity, and a 50 mM phosphate buffer solution, pH 6.8, that is used to mimic the intestinal conditions. A successful immediate release formulation releases at least 80% of the labelled amount of nicotine within 30 or 45 minutes. The delayed release formulation is evaluated by the amount of drug released at 6 hours (the leak) and how quickly the entire dose of the drug is released once the drug release is initiated. The nicotine concentration is measured in samples of the media removed from the dissolution vessel over time and injecting the sample onto a High Performance Liquid Chromatography (HPLC) system with UV detection. The amount of nicotine released is measured as a percentage of the target drug load in the dosage form (i.e. ~4 mg of drug released from an 8 mg total dose would provide a 50% dissolved result). A successful delayed release formulation releases at least 80% of the labelled amount of nicotine over approximately 30-45 minutes beginning 6 hours after the first release. The target is to minimize the amount of leak in the delayed-release formulation, and maximize the rate of drug release once the release is initiated. This results in a strong pulse of drug release and is intended to perform similarly to the immediate-release dosage form that is administered 6 hours after the first dose.

Four different formulations are developed under GMP guidelines ready for the human study. Once the lead formulations have been selected, they are scaled-up to larger equipment and batch sizes. The manufacturing parameters are further developed for that scale of equipment, and these experiments are documented in a laboratory notebook. Clinical Trial Material (CTM) drug product is tested in order to assure their correct quality, identity, strength, purity, and potency. CTM is then produced in a section of the facility that is qualified and operated in accordance with Good Manufacturing Practices (GMPs). A GMP is a system for ensuring that products are consistently produced and controlled according to quality standards. It is designed to minimize the risks involved in any pharmaceutical production that cannot be eliminated through testing the final product. GMP covers all aspects of production from the starting materials, premises and equipment to the training and personal hygiene of staff. Detailed, written procedures are essential for each process that could affect the quality of the finished product. There must be systems to provide documented proof that correct procedures are consistently followed at each step in the manufacturing process—every time a product is made. These batches are manufactured using materials that have been released by a quality unit, and the manufacturing instructions are specified in a pre-approved batch record. These batches are tested using methods that have been appropriately qualified, and they are released by a quality unit prior to dosing in a human clinical trial.

Example 5: Human Normal Volunteer Study of 12-Hr Release Formulations

Up to four 12-hr release formulations are tested in man. A 12 mg Pulsatile Release (PR) is intended to provide 2 spikes over 12 hours. The Study is a Bioequivalence Phase 1 study in 12 normal healthy normal males and females, who are non-smokers, or previous smokers who are currently non-smokers x3 months or social smokers who are willing and able to abstain from tobacco use for the duration of the study. Healthy normal volunteers are used to conduct the study, as the goal is to obtain the highest quality data with minimal interference from confounding factors. Healthy volunteer PK studies have been shown to be superior to PK studies in populations where extended overnight stays are challenging and compliance is low. For example, subjects who are ill may have a difficult time refraining from eating, and food may interfere with the interpretation of data.

Comparative PK/bioavailability of immediate-release and four different 12-hr release formulations of nicotine:
Strength/Form:
(A) Immediate Release (IR) 6 mg q6 h×4 doses
(B) Pulsatile Release (PR) 12 mg Form 1 q12 h×2 doses
(C) Pulsatile Release (PR) 12 mg Form 2 q12 h×2 doses
(D) Pulsatile Release (PR) 12 mg Form 3 q12 h×2 doses
(E) Pulsatile Release (PR) 12 mg Form 4 q12 h×2 doses Each subject has a washout time of a minimum of 3 days prior to entering into the next period. The time of confinement include Day −1 through to AM of Day 2 (2 bed nights in each period).

Safety assessments focus on ensuring that all subjects entering the study are normal and healthy using a screening and pre-first-dose-vital Signs and Physical Exam, ECG and Standard Clinical Lab tests. During the study, close attention is paid to hemoglobin due to the large blood volume from PK sampling to ensure that subject's levels are within normal range at the beginning of each period and at the end of the 5th period. PK Sampling: The PK Sampling Schedule is identical for each period and is as follows: Pre-dose (0 hr), 0.5, 1, 1.5, 2, 2.5, 3, 4, 6, 6.5, 7, 7.5, 8, 8.5, 9, 10, 12, 12.5, 13, 13.5, 14, 14.5, 15, 16, 18, 18.5, 19, 19.5, 20, 20.5, 21, 22, 24.

Analyte(s): Nicotine and cotinine. Nicotine in plasma or serum, once quantified bioanalytically, are analyzed using descriptive statistics to summarize the concentration in samples by treatment and time point. Each individual subject, by treatment, concentration versus time profiles are analyzed using non-compartmental pharmacokinetic (PK) methods to derive the PK parameters of interest. Of main interest, is the peak (Cmax) exposure, overall systemic exposure (AUC) over a 24-hour period for the various treatment regimens. In addition, the time to peak (Tmax), minimum concentration over the 24-hr interval, and half-life, are computed where possible. The main exposure parameters are compared statistically by an analysis of variance (ANOVA) according to the two, one-sided equivalence approach. Results are presented as the geometric mean ratio between the proposed modified-release nicotine regimens and the immediate-release formulation, with corresponding 90% confidence interval for the difference in means.

Example 6: NP002 in Combination with Dopaminergic Drugs for Treatment of Cognitive-Related Symptoms and Cognitive Impairment A total of 20 patients with Parkinson disease, for five years or more, who have impaired cognitive symptoms are enrolled in an interventional study. The patients are randomly assigned to NP002 or an identical placebo in addition to their regular PD dopaminergic medication. Major entry criteria are as follows: 1) clinical diagnosis of typical Parkinson's disease, 2) male or female between ages of 30 to 83, 3) Hoehn and Yahr Stage II-IV while in an "on" state, and 4) be on a stable dose of levodopa/carbidopa. They may be on additional dopaminergic drugs including dopamine agonists and/or monoamine type B oxidase inhibitors or amantadine.

The study consists of 3 phases: a treatment period of 6 months, a treatment re-titration period of 2 months, a crossover treatment period of 6 months. Subjects are randomly assigned to receive either NP002 comprising nicotine or salt thereof, or placebo. All patients are on stable levodopa/carbidopa treatment. Patients may have additional dopaminergic drugs including dopamine agonists and/or monoamine type B oxidase inhibitors or amantadine. Patients are evaluated in an "off" period, 16 hours off levodopa/carbidopa and then in an "on" period, one hour after usual morning dose of levodopa/carbidopa. NP002 or placebo in a 1:1 ratio is administered as an oral capsule 4 times a day in a blinded fashion for 6 months, and then a crossover for another 6 months. In between the treatment regimes, subjects are given a treatment re-titration period for 2 months. Dosing begins at 1 mg every 6 hours, total daily dose is 4 mg and escalated upward at 2 week intervals as follows:

Two mg every 6 hours total daily dose 8 mg for 2 weeks.
Four mg every 6 hours total daily dose 16 mg for 2 weeks.
Six mg every 6 hours total daily dose 24 mg for 2 weeks.

Patients are maintained on this dose for the duration of the next few weeks of the study until the cross-over. Because patients who are on placebo have not been exposed to nicotine, the original escalation schedule is repeated.

Safety is assessed by incidences of adverse experiences (AE), clinical laboratory tests, serum cotinine, ECG and vital signs. Impulsive symptoms are assessed using the Jay Modified Minnesota Impulsive Disorders Interview (JayMidi). Withdrawal symptoms are evaluated using the Minnesota Nicotine Withdrawal Scale (MNWS-R).

Efficacy is assessed using the Montreal Cognitive Assessment scale.

Example 7: NP002 in Combination with Dopaminergic Drugs for Reducing Cognitive Impairments Example 1 is repeated. This is a Phase II single center, randomized, double-blind, placebo controlled, efficacy, safety and tolerability study. A total of 20 male and female patients with typical Parkinson's disease with cognitive impairments are included. The study consists of an initial evaluation, evaluation every 2 months for 6 months, a cross-over, and then an evaluation every 2 months for 6 months.

Example 8: Nicotine Reduces LIDs LIDs by Acting at Nicotinic Acetylcholine Receptors (nAChRs)

Nicotine generally exerts its effect by acting at nAChRs. Multiple receptors exist throughout the body with $\alpha1\beta1^*$, $\alpha3\beta4^*$ and $\alpha7$ nAChRs being the major subtypes in the peripheral nervous system and $\alpha4\beta2^*$, $\alpha6\beta2^*$ and $\alpha7$ nAChRs the primary ones in the brain. The *asterisk denotes the presence of other nAChR subunits in the receptor. To determine the receptors relevant for nicotine's antidyskinetic effect, nAChR subtype selective drugs were tested in rats with a unilateral 6-hydroxydopamine lesion, which is a model for LID. Varenicline, which acts at all nAChRs, as well as several $\beta2^*$ selective drugs (A-85380, sazetidine, TC-2696, TI-10165, TC-8831 and TC-10600) reduced LIDs to varying extents in this parkinsonian animal model of LIDs. These data indicate that nicotine reduces LIDs by acting at nAChRs. Studies with genetically modified mice further support the idea that nicotine mediates its antidyskinetic effect via nAChRs. L-dopa-treated parkinsonian $\alpha6\beta2^*$ nAChR null mutant mice showed a 50% reduction in baseline LIDs. Nicotine did not exert an antidyskinetic effect in $\alpha4\beta2^*$ nAChR knockout mice. By contrast, there was an increase in LIDs in L-dopa-treated parkinsonian $\alpha7$ nAChR knockout mice. Thus the pharmacological and genetic studies indicate that the antidyskinetic effect of nicotine is receptor-mediated and that both $\beta2^*$ and $\alpha7$ nAChRs play an important role.

Example 9: nAChR Drugs Reduce LIDs in Parkinsonian Nonhuman Primates nAChR drugs reduce LIDs in parkinsonian nonhuman primates. Pharmacological studies were performed to investigate the therapeutic potential of nAChR in 1-methyl-4-phenyl-1,2,3,6-tetrahydropyridine (MPTP) monkeys, an animal model that closely resembles PD. Initial work showed that varenicline, a general nAChR agonist, and the $\beta2^*$ agonist TC-8831 decreased LIDs ~50% in monkeys with no tolerance, although a limitation of these drugs was the development of emesis (Table 1). Several other $\beta2^*$ selective agonists were therefore tested (Table 4). These were ABT-089, a partial $\beta2^*$ nAChR agonist (Ki=17 nM) and the full $\beta2^*$ agonist ABT-894 (Ki=0.3 nM). ABT-089 maximally decreased LIDs by 40% and ABT-894 reduced LIDs up to 60% (Zhang et al., 2014b). These effects persisted for months, with no detectable side effects and no emesis. None of the agonists worsened Parkinsonism. AZD1446, a $\beta2^*$ nAChR agonist of relatively low affinity (Ki=30 nM) was also tested. It maximally reduced LIDs by 30%. Full high affinity $\beta2^*$ nAChR agonists may be more effective. Two $\alpha7$ nAChR agonist ABT-107 (Ki=0.5 nM) and AQW051 (Ki=27 nM) also reduced LIDs in parkinsonian monkeys with varying efficacy which may relate to their affinity and agonist properties. Of note, the maximum decline in LIDs was ~60% with any one nAChR drug or with combined treatment with an β2* and α7 agonist (Table 4).

A summary of the monkey data (Table 4) show that the greatest reduction in LIDs is associated with higher affinity (≥10 nM) full nAChR agonists such as nicotine, ABT-894 and ABT-107. Partial agonists or drugs with lower affinities (such as varenicline, TC-8831, ABT-089, AZD1446, AQW051) appear less efficacious. Another important consideration is side effects; drugs such as varenicline and TC-8831 can be associated with nausea, and thus in some cases, would be less desirable.

TABLE 4 nAChR agonists reduce LIDs in monkeys

| Drug | nAChR subtype | Type of agonist | Ki | Decline in LIDs in monkeys | Dose to reduce LIDs (mg/kg) | Side effects in monkeys |
|---|---|---|---|---|---|---|
| Nicotine | All | Full | 1-3 nM | 60% | 1.0 | None |
| ABT-894 | β2 | Full | 0.3 nM | 60% | 0.01 | None |
| ABT-107 | α7 | Full | 0.5 nM | 60% | 0.10 | None |
| ABT-894 + ABT-107 | β2 + α7 | Full | — | 60% | 0.01 + 0.1 | None |
| Varenicline | All | Partial | 0.1 nM | 50% | 0.03 | Some nausea |
| TC-8831 | β2 | Full | 1-3 nM | 30-50% | 0.10 | Nausea |
| ABT-089 | β2 | Partial | 17 nM | 30-50% | 0.10 | None |
| AZD1446 | β2 | Full | 30 nM | 30% | 1.0 | None |
| AQW051 | α7 | Partial | 27 nM | 0% 60% | 8.0 15.0 | None |

Example 10: nAChR Agonists in Combination with Dopaminergic Drugs for Treatment of Fall-Related Symptoms and Improvement of Posture Stability A total of 20 patients with Parkinson disease, for five years or more, who have impaired postural stability (balance) and have fallen are enrolled in an interventional study. The patients are randomly assigned to a β2 or α7 selective nAChR agonist (such as ABT-894 or ABT-107) or an identical placebo in addition to their regular PD dopaminergic medication. Major entry criteria are as follows: 1) clinical diagnosis of typical Parkinson's disease, 2) male or female between ages of 30 to 83, 3) Hoehn and Yahr Stage II-IV while in an "on" state, 4) has had fallen more than once in past year, 5) has Montreal Cognitive Assessment (MOCA) score≥21, 6) be stable dose of levodopa/caribodpa. They may be on additional dopaminergic drugs including dopamine agonists and/or monoamine type B oxidase inhibitors or amantadine.

Patients with the following disorders or symptoms are excluded from enrolment:

Excluded are patients with atypical Parkinson, disorders that while infrequent, result in a high number of falls especially early in the disease. These disorders include Progressive Supranuclear Palsy (PSP), Multiple System Atrophy (MSA), Primary Freezing of Gait (PFG), and Corticobasiler Degeneration.

Excluded are patients with dementia MOCA≥21. Although dementia is part of PD and can be a risk for falling, more than half of our patients with PD and dementia are without a care-giver for at least 4 hours and we are uncertain if they report all their falls.

Excluded are patients who are legally blind.

Excluded are patients with major orthopedic problems of their hips or knees, patients who needed hip or knee replacements.

Excluded are patients with orthostatic hypotension. Although orthostatic hypotension, reflecting involvement of the autonomic nervous system (ANS), can be part of PD, it can also result from the use of anti-hypertensives, diuretics, selected anti-depressants, and dehydration. As it often cannot determined if a fall from orthostatic hypotension resulted from impairment of the ANS or from drugs and dehydration such persons are excluded.

Excluded are patients with a history of schizophrenia, schizo-affective disorder, bipolar disorder Excluded are patients with hallucinations, psychoses or delusions.

Excluded are patients that had deep brain stimulation (DBS) Intervention.

Excluded are patients with a history of recent stroke or myocardial infarction.

The study consists of 3 phases: a treatment period of 6 months, a treatment re-titration period of 2 months, a crossover treatment period of 6 months. Subjects are randomly assigned to receive either nAChR agonist (such as ABT-894 or ABT-107), or placebo. All patients are on stable levodopa/carbidopa treatment. Patients may have additional dopaminergic drugs including dopamine agonists and/or monoamine type B oxidase inhibitors or amantadine. Patients are evaluated in an "off" period, 16 hours off levodopa/carbidopa and then in an "on" period, one hour after usual morning dose of levodopa/carbidopa. Either the β2 or the α7 selective nAChR agonist (such as ABT-894 or ABT-107) or placebo in a 1:1 ratio is administered as an oral capsule 4 times a day in a blinded fashion for 6 months, and then a crossover for another 6 months. In between the treatment regimes, subjects are given a treatment re-titration period for 2 months. Dosing begins at 1 mg every 6 hours, total daily dose is 4 mg and escalated upward at 2 week intervals as follows:

Two mg every 6 hours total daily dose 8 mg for 2 weeks.
Four mg every 6 hours total daily dose 16 mg for 2 weeks.
Six mg every 6 hours total daily dose 24 mg for 2 weeks.

Patients are maintained on this dose for the duration of the next few weeks of the study until the cross-over. Because patients who are on placebo have not been exposed to a nAChR agonist such as ABT-894 or ABT-107, the original escalation schedule is repeated.

Safety is assessed by incidences of adverse experiences (AE), clinical laboratory tests, serum cotinine, ECG and vital signs. Impulsive symptoms are assessed using the Jay Modified Minnesota Impulsive Disorders Interview (JayMidi).

Efficacy is assessed using the Unified Parkinson's Disease Rating Scale (UPDRS), Barrow Neurological Institute (BNI) Falls Evaluation, Hoehn & Yahr Staging System, Romberg test, turning test, standing on one leg, tandem gait, step length and velocity, Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS).

Improvements of axial UPDRS subtests in either "on" or "off" or both "on or off" periods, including improvement in Gait subtest, Pull test, and FOG subtests, improvement in turning, in standing on one leg, in tandem gait, in step length and velocity, improvement in quantitative tests. All or most of these patients may have response fluctuations: "wearing off" and/or "on off" Some of these patients may have freezing of gait (FOG).

Example 11: Effect of NC001, a Central Cholinergic Agonist on Gait, Postural Stability and Falls in Parkinson Disease Falls and postural instability are major problems in Parkinson disease (PD) and unlike gait are largely unresponsive to dopaminergic replacement. Falls, injuries related to falls and fear of falling pose a major problem in PD. Improving postural stability and reducing falls will improve the lives of PD patients. Central cholinergic neurons and nicotinic receptors in the striatum, the pedunculopontine nucleus and thalamus mediate postural stability. There is evidence that cholinomimetic drugs improve postural stability and reduce falls. A problem is the lack of an effective central cholinomimetic drug. A secondary problem is the lack of effective means of continuously monitoring postural stability. Such continuous monitoring, utilizing wearable Inertial Measuring Units, IMUs, combined with traditional means of evaluating gait and postural stability (the Unified Parkinson Disease Rating Scale, motor control time (MCT), and postural perturbations utilizing the Neurocom System offer the best means of documenting and quantifying the effects of drugs on improving postural stability and reducing falls.

NC001 ((formerly NP002), Nicotine Bitartrate), a central cholinergic agonist was shown to improve gait and balance in a study on the effect of the drug on dyskinesias. In the study it was unclear if the improvement in gait and balance was secondary to a direct effect on gait and postural stability or from a secondary effect on reducing dyskinesias. Several studies suggest that cholinomimetic drugs improve postural stability and reduce falls. A problem is that these drugs, unlike NC001, do not readily penetrate the central nervous system (CNS).

We propose to study NC001 versus placebo in a group of 20 PD patients who have fallen and are at risk for additional falls utilizing traditional monitoring, MCT and postural perturbations utilizing the Neurocom system and continuous monitoring utilizing wearable IMUs. Patients are randomized to NC001 or placebo and treated for six months after which they are crossed-over.

Falls and postural instability (impaired balance) are major problems in Parkinson disease (PD) and are largely unresponsive to dopaminergic replacement. Central cholinergic neurons and nicotinic receptors in the striatum, the brainstem (pedunculopontine nucleus) and thalamus mediate postural stability. There is growing evidence that central cholinomimetic drugs may improve postural stability and reduce falls. A major problem is the relative lack of effective central cholinomimetic drugs. A secondary problem is the lack of effective means of continuously monitoring locomotion (gait) and postural stability in PD patients who are at risk for falling. Such continuous monitoring, utilizing wearable Inertial Measuring Units, IMUs, combined with traditional means of evaluating gait and postural stability (motor part of the Unified Parkinson Disease Rating Scale, UPDRS, tests of balance, motor control time (MCT), and postural perturbations utilizing a Neurocom System, offer the best means of documenting and quantifying the effects of drugs on improving postural stability and reducing falls.

NC001 (formerly NP002), Nicotine Bitartrate) a central cholinergic agonist was shown to improve gait and balance in a small but well conducted study on the effect of a central cholinomimetic drug on dyskinesias. From the study it was unclear if the improvement in gait and balance was secondary to a direct effect on gait and postural stability or from a secondary effect: a reduction in dyskinesias. Several other studies suggest that central cholinomimetic drugs may improve postural stability and reduce falls. A problem is that these drugs, unlike NC001, do not readily penetrate the central nervous system (CNS). We propose to study NC001, a potent central cholinergic agonist, versus placebo, in a group of PD patients with impaired postural stability who have fallen and are at risk for additional falling utilizing traditional monitoring (the motor part of the UPDRS), balance tests, MCT and postural perturbations combined with continuous monitoring utilizing wearable IMUs.

Weakness of Study: Nicotine is a highly potent central cholinergic agonist and may improve postural stability and reduce falls. The population chosen, however, may have disease too advanced to be improved: perhaps the intervention should be earlier, in patients with less advanced PD. Adverse effects of nicotine may be of concern in older patients with advanced PD.

Indication

Falling, injuries related to falling, and fear of falling pose a major burden to PD patients. Falls are a major cause of hospitalization for PD patients. Annual incidence of falls range from 50% to 70% in patients with advanced PD and are a major cause of disability resulting in loss of independence. Improving postural stability, reducing falls and the fear of falling may improve the lives of PD patients, and their caregivers.

Target & Pathway

NC001, nicotine bitartrate, is a known central cholinergic agonist. Nicotine (in cigarettes) has been associated with a reduced risk of developing PD (after factoring in the adverse effects of nicotine on the cardio-vascular system and on the development of cancer). Whether this is from a neuroprotective effect of nicotine on CNS cholinergic neurons or from a therapeutic effect on gait and postural stability is unknown. Central cholinergic neurons mediating gait and postural stability have been identified in the striatum, pedunculopontine nucleus and in the thalamus. Nicotine, administered orally, is an effective cholinomimetic agonist. Gait speed, postural stability, and reduction of falls have been associated with a reduction in degeneration of cholinergic neurons in the CNS. Available cholinomimetic agents with relatively poor CNS penetration (rivastigmine, donepezil) have, nonetheless had a mild, but variable effect on reducing falls.

Stage of Development

The primary objective of the study is to determine whether treatment with NC001 versus placebo in addition to dopaminergic drugs improves postural stability and reduce falls and/or severity of falls in PD patients. This is achieved by demonstrating improvement of selected MDS-UPDRS subtests in either "on" or "off" or both periods. The subtests include the "Gait" and "Pull test." The objective is achieved by demonstrating improvement on subtests such as "Standing on One Leg" and Step Length.

Since there are limitations to the above semi-quantitative tests they are complemented by tests of motor control time (MCT) and postural perturbations utilizing a Neurocom system.

The PD patient population chosen has advanced PD, is on levodopa, and is having "wearing off" Some of these patients may have dyskinesias. They are evaluated in an "off" period, 16 hours without levodopa, at a time when they are without dyskinesias. This is important as we want to be able to see the effects of NC001 on gait and postural stability in the absence of dyskinesias. Patients are then evaluated in an "on" period an hour after they receive their usual daily dose of levodopa.

A problem with such evaluations is that they capture the patient's gait and postural stability, including phenomena such as freezing of gait (FOG), a risk factor for falls, over a short period of time. The evaluation of patients in their "on" and "off" period is complemented by continuous monitoring, utilizing wearable Inertial Measuring Units incorporating accelerometers and gravitometers that monitor gait, FOG, postural stability, and falls. Patients are monitored for up to three days with the IMUs. The monitoring is supplemented by dairies kept by the patient.

The study population includes 20 patients with PD who have had PD for at least five years, who have impaired postural stability, who have fallen at least twice in a year, who are on levodopa, who are having "wearing off" (and who usually fall when they are "off"). Half of the patients are randomized to NC001 and half to placebo. The group is treated for six months and then they are switched.

A secondary objective of the study is to evaluate the efficacy of adding NC001 versus placebo in reducing dyskinesias and in improving response fluctuations: "wearing off."

Because of the effects of impaired cognition (dementia) on gait, postural stability, and falls we exclude patients with dementia. At a later time we may study NC001 in patients with dementia who fall. Parkinson disease is characterized by a loss of nigrostriatal dopamine neurons. Nicotine receptors are located in the striatum as well as the pedunculopontine nucleus and various thalamic nuclei. NC001 or placebo in a 1:1 ratio is administered as an oral capsule four times a day in a blinded fashion for six months. Then, after a crossover, for another six months. In the double blind treatment phase dosing is begun at one mg every six hours to a total daily dose of 4 mg. Then the dose is escalated to a total dose of 24 mg per day.

Development Plan

The present study is in a population most at risk for falling: a population with the most to gain from a successful outcome. If NC001 improves postural stability and reduces falls, we will explore the utility of NC001 in a population of PD patients with dementia who are at risk for falling. We may also explore the possible improvement of NC001 on cognition and alertness.

IP/Patient Landscape

The Inertial Measuring Units (IMUs) developed by Dr. Lockhart, can be adapted to I-phones. They are easily wearable. There are competing devices on the market. If Dr. Lockhart's IMUs prove useful in the study, they may become the standard for monitoring PD. While this will be beneficial to Arizona State University, their low cost and utility will be even more beneficial to PD patients.

Future Objectives

At present the treatment of PD centers around dopaminergic drugs: levodopa, dopamine agonists, MAO-B inhibitors. For selected patients who develop "wearing off", dyskinesias, or FOG, deep brain stimulation (DBS) of the globus pallidum interna and the subthalamic nucleus, and less commonly the pedunculopontine nucleus (for DBS) are options. Dopaminergic drugs or DBS do not appreciably reduce fall risk or falls in patients with advanced PD. Neither do they halt the progression of PD. Centrally acting cholinomimetic drugs may reduce fall risk or falls, may improve cognition, and could, possibly, slow disease progression. Another class of drugs would be most welcome in the treatment of PD.

Example 12: Development of NC001 Formulations

PD is a neurodegenerative disorder that is characterized, in part, by a progressive loss of dopaminergic neurons in the substantia nigra pars compacta. It affects 1.5% (VisionGain, 2008) of the global population over 65 years of age. The lack of dopamine causes the classical motor symptoms of bradykinesia, rigidity and resting tremors (Rascol et al., 2011; Schapira and Jenner, 2011; Poewe et al., 2012; Connolly and Lang, 2014; Vijverman and Fox, 2014). These symptoms are dramatically improved by current dopamine replacement strategies, which include levodopa (L-dopa), the precursor of dopamine and dopamine receptor agonists, as well as monoamine oxidase B (MAO B) inhibitors and catechol O-methyltransferase inhibitors. Dopamine replacement therapies greatly reduce Parkinson's symptoms and enable patients to lead relatively normal lives; however, after several years of disease progression, treatment is complicated by the onset of motor fluctuations and dyskinesia, which leads to alternating periods of reduced mobility and abnormal involuntary movements. Dyskinesia almost always occurs as a side effect of long-term therapy with levodopa. Dyskinetic movements, dyskinesia (Iravani et al., 2012; Huot et al., 2013; Lewitt and Mouradian, 2014), is the term used to describe unintended, involuntary and uncontrollable movements, including twitches, jerking and twisting. Treating physicians generally respond to the problem caused by dyskinesias by either delaying treatment with L-dopa or under-treating the patient with L-dopa to delay the development of dyskinesias, but this tactic effectively removes the only effective PD therapy and is typically followed by an increase in rigidity or tremors. At this time, apart from amantadine, which is currently being used off-label and has severe side effects (Sawada et al., 2010;

Connolly and Lang, 2014; Ory-Magne et al., 2014), there is currently no approved treatment for L-dopa induced dyskinesias (LIDs).

Neurocea's lead product, NC001 ((formerly NP002), Nicotine Bitartrate) is designed to treat LIDs. Neurocea seeks to develop NC001, a proprietary pulsatile time-release formulation of nicotine (the active ingredient), that mimics the PK profile of the formulation used in a successful Phase 2 clinical trial of NP002 (Randomized, Double-Blind, Parallel Group, Placebo Controlled Safety, Tolerability and Efficacy Study of NP002 in Subjects With Idiopathic Parkinson's Disease With Dyskinesias Due to Levodopa Therapy) where drug was administered every six hours. The results showed a strong statistically and clinically significant benefit in several disease parameters versus placebo. Along with no relevant safety concerns, nicotine may to become the treatment of choice for LIDs. A formulation of nicotine (NC001) may allow the delivery of nicotine as 4 doses spaced 6 hours apart but delivered as no more than two pills taken every 12 hours. The formulation provides short-duration pulses of drug to the system, specifically so that the nicotine may be nearly absent from the blood system before the next pulse. In our testing, this has been shown to avoid the building of tolerance to nicotine. This formulation uses pharmaceutical polymers technology in combination with organic ionic salts where the permeability is controlled through ionic interactions in the coating.

Key Technology Objectives

As described in the research strategy, medication compliance is a particularly challenging problem for people with PD. Medications that require a dosage regimen every 4-6 hours cause sleep disturbance, missed doses and in the case of PD leads to increasing motor complications. This is well established in PD as can be seen by the multiple different new dopamine formulations that are being developed to minimize the problem with medication compliance.

The controlled release of a drug replace at the preferred absorption site optimizes delivery of the active ingredient within the therapeutic window (Stocchi F, et al. 1996), maximizing its therapeutic benefits. The drug product with 2 discrete drug release pulses is intended for use in clinical trials for treatment of LIDS. This formulation approach allows for reduced dosing frequency in order to provide the pharmacokinetic (PK) profile evaluated in the previous Phase 2 study. The formulation is a combination of nicotine drug substance and excipients, in combination with the specific manufacturing processes, in order to achieve the unique drug release profile for nicotine, resulting in the targeted PK profile.

The first pulse from the 2 pulse formulation is a traditional immediate release, intended to achieve rapid therapeutic effectiveness. This is be achieved by drug layering the nicotine drug substance onto a pellet substrate of microcrystalline cellulose (MCC) in a fluid bed dryer fitted with a Wurster column insert for efficient application of the materials. A brand of the MCC spheres that is commercially-available is Celphere. The drug substance is sprayed onto the MCC pellets along with a soluble polymer that helps bind the nicotine to the pellet. This is then be overcoated with an additional immediate-release polymer that can be purchased in different colors for aesthetics. A brand of commercially available aesthetic coating is Opadry.

The second pulse is drug-layered with the nicotine and soluble polymer in the same manner as the immediate-release component. The delayed-release pulse is also include an organic acid salt in the drug layer such as succinic acid. The functional film coat is then applied to the drug loaded pellets. The functional film coat is comprised of a copolymer of ethyl acrylate and methyl methacrylate containing methacrylic acid ester with quaternary ammonium groups, and triethyl citrate as a plasticizer. The ratios of the polymers and organic acid modifier determine the time of the release of the drug from the delayed-release component. A brand of commercially-available polymer is Eudragit RL and Eudragit RS. The functional film coat for the delayed release component is also applied in a fluid bed dryer fitted with a Wurster column. The organic acid modifier interacts with the copolymer in order to create pores for the water to leach into the formulation, and eventually, for the drug to be released.

Both populations of pellets can be filled into a capsule for administration, or blended with additional inactive ingredients and formed into a tablet. Both approaches have been used in commercial drug products.

This pulsatile formulation enables target drug delivery and improve disease management through better compliance and enhanced patient convenience. It provides a safe drug that does not make PD worse and allows physicians to treat PD with the most effective L-dopa therapy regimen.

Product Development Process Required to Support NDA

One of the great strengths of this project is that nicotine at the dose that we plan to commercialize has already been proven to be safe. As such, the opportunity for filing an NDA without additional preclinical safety pharmacology and toxicology or long term clinical safety is feasible through the use of the 505(b)(2) pathway. This pathway allows us to utilize data in the public domain to support the NDA. A 505(b)(2) is a new drug application that contains full safety and effectiveness reports, but allows some of the information required for approval to come from studies not conducted by or for the applicant. This method enables a shorter development path for new drugs leading to potential filing for an NDA in a fraction of the time and cost required by traditional paths.

In addition to these requirements, it is also necessary to provide a fully updated CMC section to the existing IND as described below in section "FDA communications". We calculated that we need 140 patients in treatment and 140 in placebo groups (280 patients total), which is sufficient (90% power) to detect a difference between NC001 and placebo in the UDysRS total score, assuming a two-sided two-sample t-test at the 5% level of significance. Sample size calculations were done based on the continuous outcomes. The mean change from baseline and standard deviation for each treatment group were calculated. The sample size calculations were done for 80% and 90% power. The first set of sample sizes is based on a one-sided alpha=0.05, and the second is a two-sided alpha=0.05. Sample sizes were calculated assuming a two-sample t-test. See Table 5.

TABLE 5

| Scale (Week 10 result; change from baseline) | NP002 mean | NP002 sd | Placebo mean | Placebo sd | NC001: one-sided alpha = 0.05 80% power | NC001: one-sided alpha = 0.05 90% power | NC001: two-sided alpha = 0.05 80% power | NC001: two-sided alpha = 0.05 90% power |
|---|---|---|---|---|---|---|---|---|
| UDysRS total | 15.4 | 15.97 | 9.4 | 14.81 | 166 | 228 | 210 | 280 |
| UDysRS part III | 5.2 | 6.33 | 2.5 | 4.33 | 102 | 140 | 130 | 172 |
| UDysRS walking | 4.4 | 5.46 | 0.8 | 5.00 | 54 | 74 | 70 | 92 |
| UDysRS historical | 8.0 | 9.46 | 4.3 | 6.68 | 124 | 170 | 156 | 210 |
| LF-ADL mean change | 3.0 | 4.05 | 1.5 | 3.40 | 156 | 216 | 198 | 264 |

Research Strategy

Figure 4:
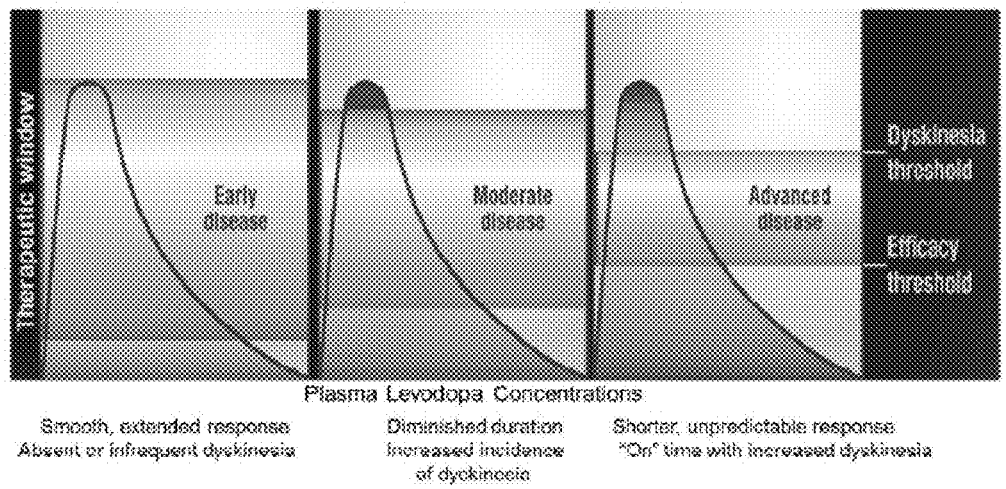
FIG. 4 illustrates symptoms and side effects that occurs at the levodopa therapeutic window diminishes.

Significance: This project has the potential to dramatically change the life expectancies, quality of life and quality of care for patients suffering from Parkinson disease (PD) by addressing a key limiting aspect of therapeutic intervention for PD. PD is a neurodegenerative disorder leading to loss of dopaminergic neurons in the substantia nigra pars compacta. The lack of dopamine causes the classic signs of PD, tremor and "freezing". Clinically this is manifest as bradykinesia, akinesia, rigidity and resting tremors (Rascol et al., 2011; Schapira and Jenner, 2011; Poewe et al., 2012; Connolly and Lang, 2014; Vijverman and Fox, 2014). A major breakthrough for PD came with the discovery that levodopa could reverse the tremor and "freezing" and allow patients to move normally. There is no doubt that PD symptoms are dramatically improved by current dopamine replacement strategies, which include various oral formulations of levodopa (L-dopa), the precursor of dopamine, as well as dopamine receptor agonists. While dopamine replacement therapies greatly reduce PD symptoms and enable patients to lead relatively normal lives, after a few years of treatment with levodopa, treatment is complicated by the onset of a dyskinetic movement disorder (Iravani et al., 2012; Huot et al., 2013; Lewitt and Mouradian, 2014). Dyskinetic movements, or dyskinesia, are terms used to describe unintended, involuntary and uncontrollable movements, including twitches, jerking, and twisting. The dyskinesias can be dramatic and debilitating. These abnormal movements are a direct complication of long-term therapy with levodopa and dopamine agonists and are therefore referred to as Levodopa Induced Dyskinesias (LIDs). In order to manage the dyskinesia, patients must reduce the dose of dopamine and therefore spend more time in a bradykinetic state suffering from rigidity and tremors. Patients often end up fluctuating between dyskinesia and bradykinesia, depending on the dopamine level; which is based on the time the patient took medication (FIG. 4).

Currently, there are no approved treatments for dyskinesia in spite of the fact that multiple agents have been tested preclinically and in clinical trials. While several drugs have been tested, there are only two current products in development. One is NC001, a formulation of nicotine, and the other is amantadine. Amantidine, an anti-viral agent with an unclear mechanism of action, was serendipitously discovered to reduce dyskinetic movements. Because amantadine is an approved drug (approved in 1966) for the treatment of influenza, it is available for use off-label to treat LIDs. However, it is used infrequently. The approved form of the drug has a very long half-life and has erratic absorption. This leads to significant, often intolerable side effects (Sawada et al., 2010; Connolly and Lang, 2014; Ory-Magne et al., 2014). The most severe side effects include hallucinations and livedo reticularis. The livedo reticularis can be irreversible and often can take years to reverse after cessation of the drug. However, a new formulation of amantadine (amantadine extended release) has been developed that may offer an improved pharmacokinetic profile leading to less severe side effects. This drug is currently in several Phase 3 trials sponsored by Adamas Pharmaceuticals. To our knowledge there are no other agents in the clinic for LIDs.

Nicotine Reduces LIDs in Both Rodent and Primate Models

Figure 5:
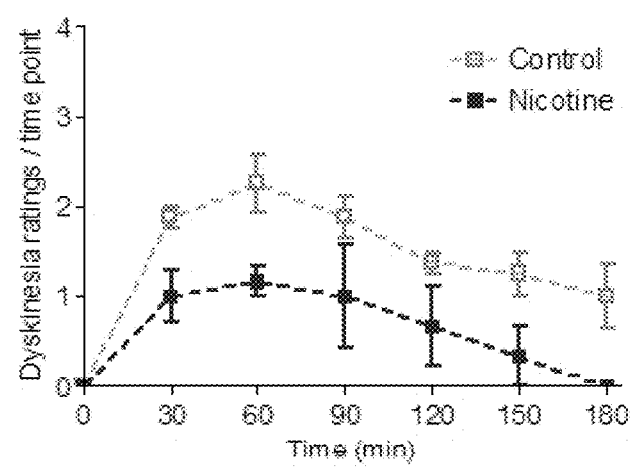
FIG. 5 illustrates a graph of dyskinesia ratings/time point on a Y axis and time (min) on an X axis in control and nicotine treated monkeys.
Figure 6:
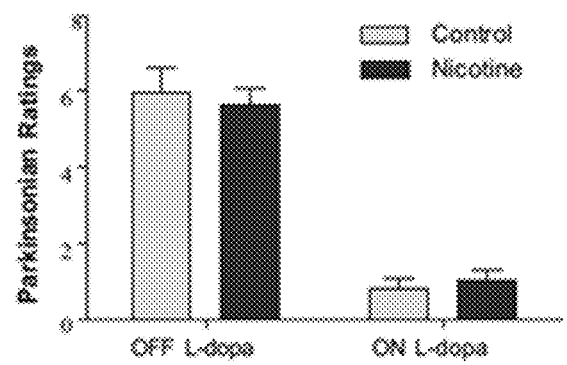
FIG. 6 illustrates a graph of Parkinsonian ratings on a Y axis in an OFF L-dopa (left bars on X axis) and ON L-dopa (right bars on X axis) in control and nicotine treated monkeys.

The rationale for investigating the anti-dyskinetic potential of nicotine stemmed from initial basic research findings from our group. In rats and mice, we found that nicotine reduced LIDs when administered by any one of several methods including oral application, injection and slow-release minipumps, with no decline in its efficacy over time (Quik et al., 2007; Bordia et al., 2010; Huang et al., 2011a). A critical discovery came when we also established that nicotine reduced LIDs in parkinsonian monkeys, the animal model that most closely mimics the motor deficits observed in PD (Bezard and Przedborski, 2011). Nicotine (which binds and activates all nicotinic receptors) resulted in a 60% decline in LIDs in monkeys without worsening of parkinsonism (Quik et al., 2007; Bordia et al., 2008) (FIG. 5 and FIG. 6). FIG. 5 shows that NP002 reduces levodopa-induced dyskinesia (LIDs) in a monkey model. FIG. 6 shows that NP002 does not increase the Parkinsonian symptoms in the OFF L-dopa or ON L-dopa. This reduction persisted for months, with no tolerance or loss of efficacy and no detectable side effects.

The neurobiological mechanisms underlying LIDs are not well understood. Extensive studies have implicated multiple neurotransmitter systems (Huot et al., 2013; Al Dakheel et al., 2014), including nicotine cholinergic receptors (nAChRs). There is extensive overlap in the organization and function of the nicotinic cholinergic and dopaminergic systems in the basal ganglia (Quik and Wonnacott, 2011). Nicotine is known to influence dopamine release and alter dopamine-related motor behaviors in animals. Our finding that nicotine could be used in an animal model of dyskinesia was only the first step to considering a path for a clinical use of nicotine. Nicotine is difficult to administer safely, and studies had suggested that rather high and sustained doses of nicotine were required for neuroprotection (Belluardo N et al., 2000; Picciotto M R and Zoli M, 2008; Quik M et al., 2007b). In fact, there had been anecdotal evidence that using the nicotine patch, which produces continuous exposure to nicotine, might be useful in slowing parkinsonian symptoms (currently there is a large NIH funded study evaluating high dose nicotine patch for neuroprotection in early stage PD patients.) However, we have noted that sustained activation of nicotine receptors does not seem to provide dyskinesia reduction (unpublished clinical observations in patients with PD and LIDs who have used nicotine patches over the counter or have been in neuroprotection trials using the patch).

A major challenge with nAChRs is that they become rapidly desensitized with continuous exposure to nicotine. Once desensitized, they lose their responsiveness to agonist drugs, and in addition, not all receptors desensitize at the same rate. So, for example, the cardiac receptors may desensitize more slowly than those in the brain. This leads to multiple problems with safety, addiction and withdrawal symptoms from continuous treatment with nicotine. In our clinical trial we utilized a dosing regimen that provided short-duration pulses of NP002 (nicotine) to the system, specifically so that the nicotine would be cleared from the blood system before the next pulse. Fortunately, nicotine is rapidly absorbed and has a very short half-life (Compton R F et al., 1997; Schneider N G et al., 2001; Hukkanen J et al., 2005). We sought to capitalize on this property by developing an oral formulation that could be swallowed, rapidly absorbed and cleared within about 2 hours. We then waited 6 hours before administering another dose of the medication. That way, the brain has at least 4 hours free of nicotine exposure, which should be sufficient to avoid nAChR desensitization.

Results: Phase 2 Clinical Trial of Intermittent Doses of Short-Acting Nicotine in Subjects with PD and LIDs This study (ClinicalTrials.gov identifiers NCT00957918) was conducted under an IND (#105268) with the FDA as a multi-center placebo-controlled, safety, tolerability, and exploratory efficacy study designed to be used as one of two studies to support regulatory approval for nicotine for the treatment of LIDs. The safety and tolerability of nicotine in subjects with idiopathic PD was assessed by adverse events (AEs), safety laboratory tests, physical examinations, electrocardiograms (ECGs), vital signs, and assessments of impulse control, nicotine withdrawal symptoms, and changes in primary parkinsonian symptoms using an escalating dose of nicotine delivered every six hours for 10 weeks. At the time the study was performed (2009), there was no FDA accepted instrument for measuring treatment efficacy for LIDs. Therefore, several secondary objectives were utilized to assess efficacy including the Unified Dyskinesia Rating Scale (UDysRS). Since the completion of this study the UDysRS has been validated in several studies and is considered by the FDA to be a validated instrument for determining if a drug is efficacious.

Figure 7:
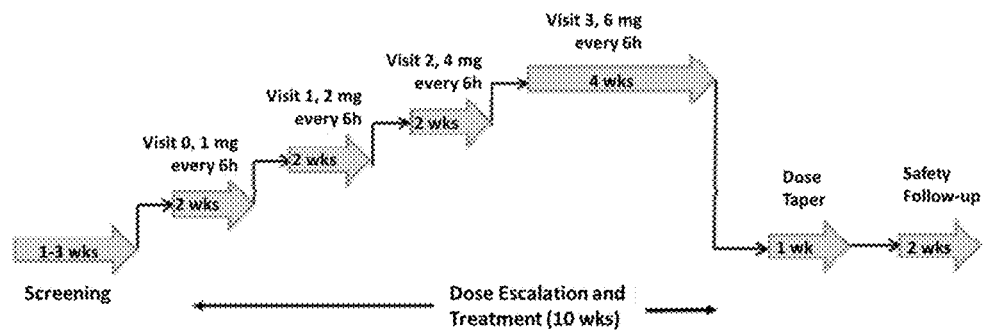
FIG. 7 illustrates a schematic of Phase 2 safety and tolerability study trial design.

A total of 65 male and female subjects with idiopathic PD with LIDs were randomized in the study. The study consisted of 4 phases (FIG. 7): screening phase (up to 3 weeks), double-blind treatment phase (10 weeks), taper phase (2 weeks), and follow-up phase (2 weeks). The approximate duration of the study for each subject was 17 weeks. Following the screening phase, study subjects were randomly assigned to receive either treatment with NP002 or placebo in a 1:1 ratio, administered as an oral capsule 4 times a day in a blinded fashion for 10 weeks. During the double-blind treatment phase, dosing was begun at Visit 0 at 1 mg every 6 hours (total daily dose [TDD]=4 mg/day) and escalated upwards at 2-week intervals as follows: 2 mg every 6 hours (TDD=8 mg/day) at Visit 1 (Week 2); 4 mg every 6 hours (TDD=16 mg/day) at Visit 2 (Week 4); 6 mg every 6 hours (TDD=24 mg/day) at Visit 3 (Week 6). Subjects were maintained on 24 mg/day for 4 weeks. The subsequent taper phase (2 weeks total), beginning at Visit 4 (Week 10), consisted of 9 days of drug taper and 5 days off drug prior to Visit 5 (final safety visit). All subjects had a follow-up phone call 1 week and 2 weeks after the final safety visit. Ondansetron was provided by the sponsor and dispensed with each dose escalation step with instructions to use it for nausea and vomiting only during the first 4 days following dose initiation or escalation. Subjects who tolerated a TDD of 16 mg/day but who did not tolerate 24 mg/day due to nausea or vomiting, at the investigator's election, were allowed to drop down to the 16 mg/day dose level. No other dose down-titration was allowed. See Table 6.

TABLE 6

Dose Escalation Schedule

|  | Visit 0 | Visit 1 (Week 2) | Visit 2 (Week 4) | Visit 3 (Week 6) | Optional | Visit 4 (Week 10) |
|---|---|---|---|---|---|---|
| Target mg per dose (or placebo) | 1 mg | 2 mg | 4 mg | 6 mg | Down titration 4 mg | Taper bottles |
| Total Daily Dose | 4 mg | 8 mg | 16 mg | 24 mg | 16 mg | 9-day taper |

Importantly, a total of 65 subjects (35 in the NP002 group and 30 in the placebo group) were randomized, and 48 subjects (25 in the NP002 group and 23 in the placebo group) completed the study. After randomization, 17 subjects withdrew from the study (10 subjects in the NP002 group and 7 subjects in the placebo group). No subject withdrew before taking any study medication. The most common reasons for withdrawal were AEs (n=11; 6 subjects in the NP002 group and 5 in the placebo group) and protocol violations (n=4; 2 subjects in the NP002 group and 2 in the placebo group). In addition, there were no issues with impulsivity or withdrawal symptoms. Importantly, neither the UPDRS Part III nor the Hoehn and Yahr scales showed any worsening during the study (and showed slight improvement), demonstrating that there was no worsening of Parkinson symptoms. Therefore, it was clear that we had established a safe and well tolerated way to administer nicotine to nicotine naïve patients with PD who were being treated with dopamine agents (see Table 7).

TABLE 7

Subject Disposition and Primary Reasons for Study Discontinuation (All Subjects)

|  | NP002 | Placebo | All |
|---|---|---|---|
| Randomized subjects, N | 35 | 30 | 65 |
| Subjects who received study treatment, n (%) | 35 (100.0) | 30 (100.0) | 65 (100.0) |
| Subjects who required dose reduction or discontinuation of study treatment,[a] n (%) | 7 (20.0) | 5 (16.7) | 12 (18.5) |
| Subjects who completed study per protocol,[b] n (%) | 25 (71.4) | 23 (76.7) | 48 (73.8) |

TABLE 7-continued

Subject Disposition and Primary Reasons for Study Discontinuation
(All Subjects)

|  | NP002 | Placebo | All |
|---|---|---|---|
| Subjects who discontinued the study, n (%) | 10 (28.6) | 7 (23.3) | 17 (26.2) |
| Primary reason for study discontinuation, n (%) |  |  |  |
| Adverse event | 6 (17.1) | 5 (16.7) | 11 (16.9) |
| Protocol violation | 2 (5.7) | 2 (6.7) | 4 (6.2) |
| Other[c] | 2 (5.7) | 0 (0.0) | 2 (3.1) |

Note:
Percentages were based on the number of subjects randomized in the study in each column.
[a]Treated subjects who had any adverse events with action taken = reduced/discontinued study drug.
[b]Subjects who completed the study according to the end-of-study CRF form.
[c]"Other" reason was "subject going on vacation" (both subjects)

NP002 is Efficacious for the Treatment of LIDs

Figure 8:
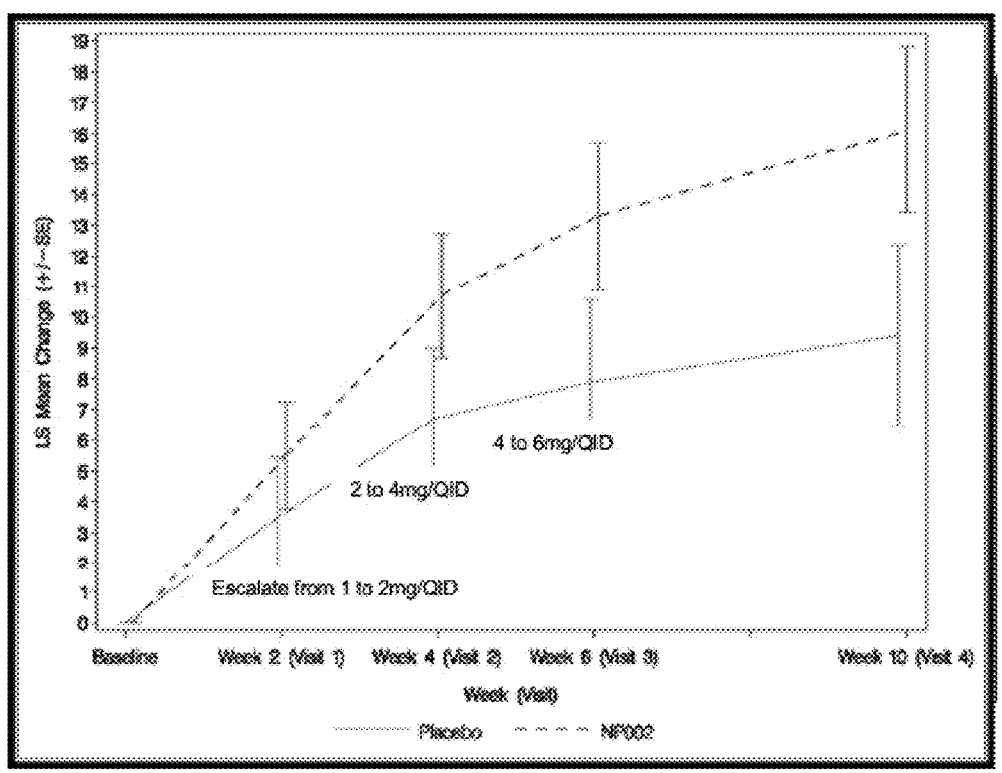
FIG. 8 illustrates a graph of LS mean change from baseline in UDysRS total. X axis represents time in weeks along with an associated visit in parentheses. Y axis represents the least-squares mean change from baseline based on a mixed model with associated standard error of that change. A range of the UDysRS total score is 0 to 104.
Figure 9:
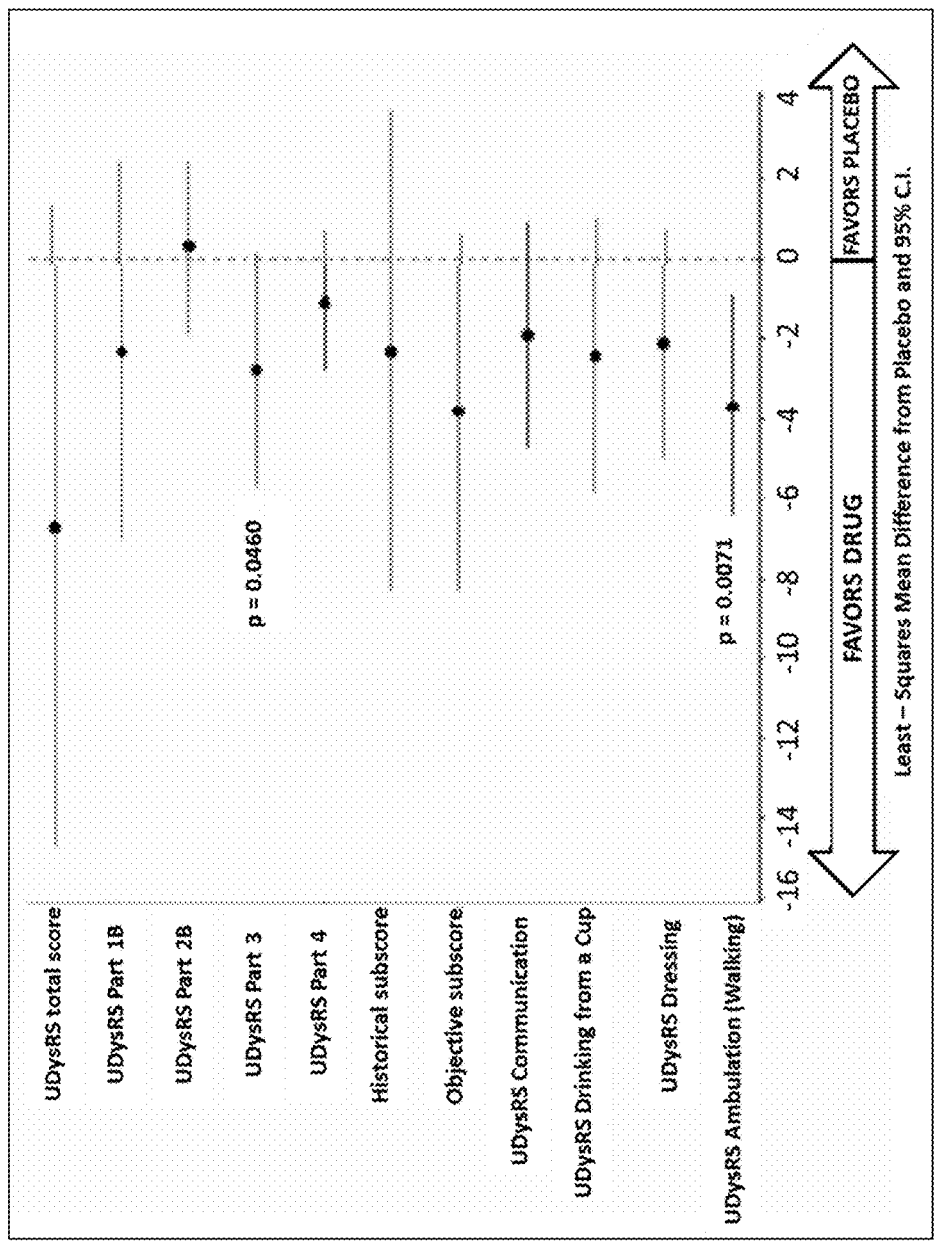
FIG. 9 illustrates a Forest plot of Least Square (LS) mean difference between placebo and NP002 in change from baseline to end of treatment period (week 10) in UDysRS total.

We found that NP002 was superior to placebo on ALL patient- and physician-rated assessments of efficacy, and in some cases achieved statistical significance (examples are shown in FIG. 8 and FIG. 9). FIG. 8 shows efficacy continues to improve and reaches separation after an additional 4 weeks of maximum dosing. FIG. 9 shows score and subscores favored drug over placebo for the total score as well as the subparts.

The improvements were judged to be clinically significant by leading Parkinson's experts, notably, Dr. Abraham Lieberman, Director of the Muhammad Ali Parkinson Center and the Movement Disorder Clinic of Barrow Neurological Institute at St. Joseph's Hospital and Medical Center, and Dr. William Langston, Scientific Director, Chief Scientific Officer and Founder of the Parkinson's Institute.

Statistically significant differences favoring nicotine compared to placebo were seen in dyskinesia disability (UDysRS part 3) and Walking (indicating improvement in gait and balance), the percentage of responders on the Lang-Fahn Activities of Daily Living (LF-ADL) scale and on the Patient Global Impression-Change (PGI-C) scale. There was a statistically significant difference between treatment groups in the number of LF-ADL responders (subjects with ≥25% reduction from baseline) at Visit 4 (Week 10) (p=0.0453). In addition, there was a statistically significant difference between treatment groups in the number of PGI-C responders (subjects with a score of 1, 2, or 3) at Visit 4 (Week 10) (p=0.0048). There were 21 (77.8%) PGI-C responders in the NP002 group compared to 9 (37.5%) responders in the placebo group. Corroborating this response, there was a statistically significant difference between treatment groups in the numbers of subjects in the different categories (1 through 7) of the PGI-C scale at Visit 4 (p=0.0230). Importantly, all scales designed to assess dyskinesia either were numerically and/or statistically significantly superior to placebo. In addition, using the UPDRS, we demonstrated that NP002 did not cause any worsening of the PD symptoms (trend favored nicotine compared to placebo and there was no indication of worsening PD and possible slight improvement). Therefore, we established that nicotine is efficacious for the treatment of LIDs.

In summary, this method of delivery of nicotine in our testing has been shown to avoid the building of tolerance and dependence on nicotine when patients were withdrawn from therapy. It is safe and it is efficacious. This critical in formulating the ultimate successful nicotine product for the treatment of LIDs.

Innovation

The use of every 6 hour dosing formulation is not viable in routine clinical use for this patient population. It would be an extraordinary challenge for a large clinical study, as compliance could be low, which would complicate interpretation of the data. We conducted patient and physician interviews and indeed we found that the patients are already dealing with significant medication challenges with regard to L-dopa. In spite of the fact that patients often require L-dopa every 4-8 hours, many patients are non-compliant, and this leads to major challenges in care. We also reviewed additional data and indeed found that large clinical trials (100 patients or greater) have major compliance constraints when medications must be given every six hours.

Approach

Importantly nicotine's biopharmaceutical properties lend themselves to improved dosage formulations. Nicotine is available as a free base and in various salt forms (Siegfried Ltd, 2009). The nicotine bitartrate dihydrate salt is freely soluble in aqueous media across the physiological pH range and is commercially available as pharmaceutical grade material. Nicotine is absorbed across human tissues, including the skin. It is well-absorbed in the gastrointestinal tract, with an oral bioavailability of approximately 30% (20% to 40% reported in literature) (Hukkanen, J. et al. 2005). Nicotine undergoes first-pass metabolism and is extensively metabolized into cotinine, resulting in the low and variable reported absolute bioavailability estimates. These high solubility and permeability characteristics lend themselves to development of modified-release (including pulsatile release) dosage forms including multiple bolus release profiles.

Phase 1 Aim 1

Figure 10:
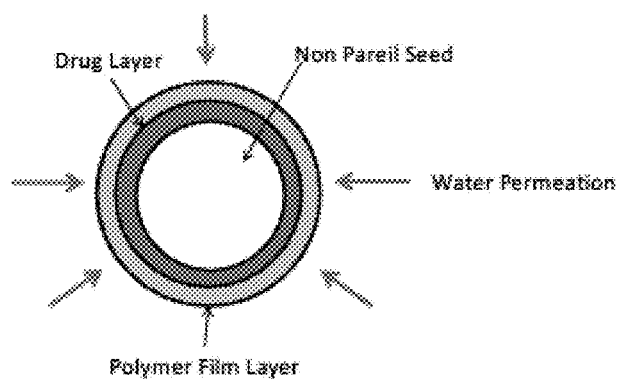
FIG. 10 illustrates a multiparticulate PH independent dosage form. Coating substrate is shown in white with drug containing layer. A rate controller polymer is layered on top of the drug containing layer.

Aim 1 is a solid, oral dosage form capable of delivering a bolus of nicotine to a human approximately every 6 hours. It is a 2 pulse formulation that delivers an immediate-release bolus at time zero, and a second immediate-release bolus of nicotine approximately six hours after ingestion. This 2 pulse dosage form is administered 2 times in a day spaced 12 hours apart (q12 hr) in order to mimic the PK profile previously evaluated in the Phase 2 studies. This formulation focuses on a multiparticulate immediate-release dosage form that is coated with a semi-permeable membrane. This membrane, once hydrated, allows water flow into the dosage form, but does not allow drug to leak out through the membrane. In addition to the active drug substance, the core of the dosage form may contain organic salts, swellable materials, or superdisintegrants that provides the driving force for the water uptake and help dictate the timing of the programmed drug release. An example of a single pellet from the multiparticulate formulation approach, which is well-suited for a low dose drug, is shown in FIG. 10. A 15% solution of nicotine is prepared including hypromellose (HPMC) as a binder and succinic acid as the organic acid modifier. This solution is coated onto nonpareil seeds using a fluid bed dryer fitted with a precision coater apparatus until a 20% solids weight gain is achieved on the pellets. The final drug layer formulation contains nicotine, HPMC, and succinic acid in a 5:3.5:1.5 ratios. If necessary, alternative binders may be used in order to improve the quality of the adherence of the drug layer to the nonpareil seed. This core drug-loaded pellet may be coated with an immediate release polymer such as Opadry for aesthetics and used as the immediate release component of the composite dosage form. For the delayed release pellets, a separate population of the core drug loaded pellets is further coated with a separate functional polymer film coat. An aqueous solution of Eudragit RS is prepared with triethyl citrate as the plasticizer and talc functioning as the antitack agent in a 6:1:3 ratios. This solution is coated onto the drug loaded pellets using a fluid bed dryer fitted with a precision coater to total solids weight gain of approximately 70%. The optimum weight gain is determined experimentally by using in vitro dissolution as the feedback mechanism. Alternative polymer materials such as Eudragit RL may also be included in the polymer film coating formulation to modify the lag time or release rate of the nicotine from the delayed release pellets. Length of the lag time and strength of the drug release can be tailored based on coating formulation and coat weight gain (Devane et al., patent).

Manufacturing Facility

Initial formulation development experiments are conducted on small, laboratory scale equipment and batch sizes (10-50 g/batch). These batches are manufactured at the laboratory or benchtop scale, and manufacturing instructions and conditions are documented in a notebook. This material is suitable for in vitro testing but not for clinical use.

Formulation Evaluation

Figure 11:
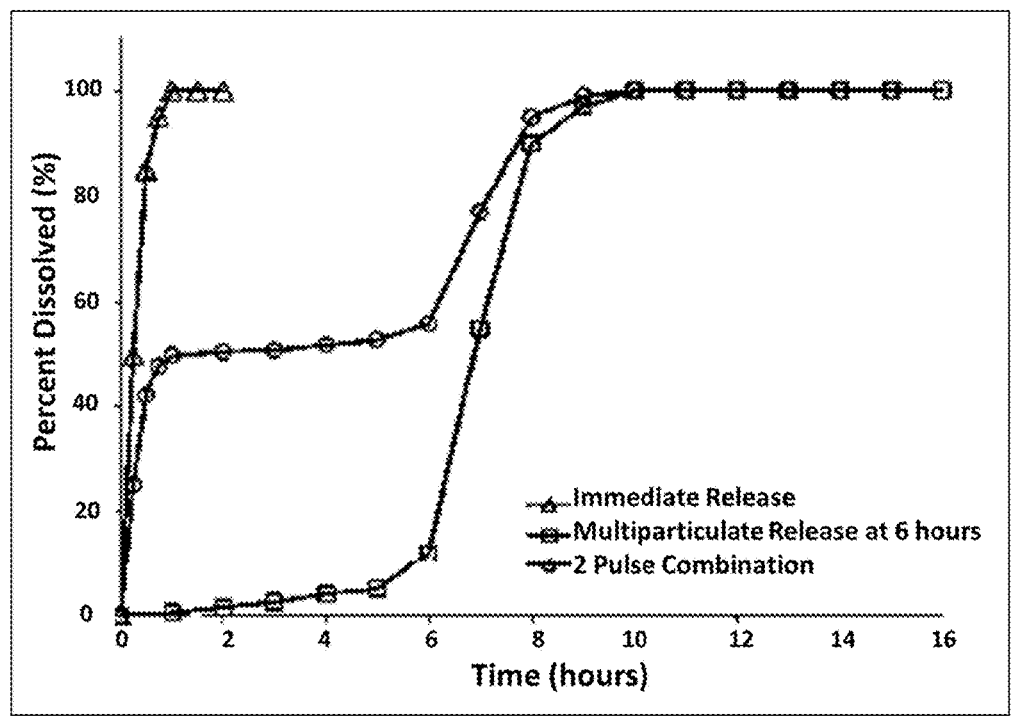
FIG. 11 illustrates a drug release profile for an immediate release (triangles), delayed release (squares), and a 2 pulse drug release profile (circles).

Formulation prototypes are evaluated using a standard drug product testing approach, including evaluation of drug product content assay, impurities evaluation, uniformity of dosage units, and in vitro drug nicotine release rate evaluation. An important tool for evaluation of solid, oral dosage forms, including modified-release dosage forms, is in vitro dissolution testing. Dissolution testing is the industry standard for evaluation of the release rate for all solid, oral dosage forms, both immediate-release and modified-release. It is used during development to assess the performance of the prototype formulations, during routine commercial batch release to ensure consistency for product that is marketed to patients, and can be used to predict the in vivo performance with an in vivo/in vitro correlation (IVIVC). Once an IVIVC has been established, the pharmacokinetic profile of the dosage form can be predicted by evaluation of the in vitro release rate. The dissolution test conditions can be tailored in order to mimic conditions in the gastrointestinal tract, and provide insight and sometime predict the in vivo drug release rate. Specifically, the immediate release formulations are evaluated in dilute HCl, with a pH of 1.1, to mimic the fasted stomach conditions, and a pH 4.5 buffer to mimic the fed stomach conditions. Delayed release formulations can be challenged in dilute HCl media, with a change to pH 6.8 media to mimic the movement from the stomach to the small intestine. See FIG. 11 are examples of theoretical in vitro dissolution profiles for an immediate-release dosage form, a dosage form with a bolus release at 6 hours, and a 2 pulse combination of these 2 dosage forms. FIG. 11 illustrates a drug release profile for an immediate release (triangles), delayed release (squares), and a 2 pulse drug release profile (circles). Triangles exhibit an immediate release of drug, reaching complete dissolution within 1 hour of a start of a dissolution challenge. A delayed-release component is indicated by squares and exhibits a similar release to an immediate-release rate but delayed by approximately 6 hours. A third profile is indicate by circles and is a composite of 2 different pellet populations and resulting a 2 pulse drug release profile.

Formulation Selection and Criteria for Success

The in vitro evaluation of the immediate release pulse and the delayed release components of the dosage form are evaluated in a dissolution bath with paddles rotating at 50 RPM at 37° C. The media that are employed are a dilute HCl solution at pH 1.1 to simulate the condition in the gastric cavity, and a 50 mM phosphate buffer solution, pH 6.8, that are used to mimic the intestinal conditions. A successful immediate release formulation releases at least 80% of the labelled amount of nicotine within 30 or 45 minutes. The delayed release formulation is evaluated by the amount of drug released at 6 hours (the leak) and how quickly the entire dose of the drug is released once the drug release is initiated. The nicotine concentration is measured in samples of the media removed from the dissolution vessel over time and injecting the sample onto a High Performance Liquid Chromatography (HPLC) system with UV detection. The amount of nicotine released is measured as a percentage of the target drug load in the dosage form (i.e. ~4 mg of drug released from an 8 mg total dose would provide a 50% dissolved result). A successful delayed release formulation releases at least 80% of the labelled amount of nicotine over approximately 30-45 minutes beginning 6 hours after the first release. The target is to minimize the amount of leak in the delayed-release formulation, and maximize the rate of drug release once the release is initiated. This results in a strong pulse of drug release and is intended to perform similarly to the immediate-release dosage form that is administered 6 hours after the first dose.

Phase 1 Aim 2: Manufacturing of GMP Clinical Trial Material

Four different formulations are developed under GMP guidelines ready for the human study. Clinical Trial Material (CTM) drug product is tested in order to assure their correct quality, identity, strength, purity, and potency. CTM is then produced in a section of the facility that is qualified and operated in accordance with Good Manufacturing Practices (GMPs). These batches are manufactured using materials that have been released by a quality unit, and the manufacturing instructions are specified in a pre-approved batch record. These batches are tested using methods that have been appropriately qualified, and they are released by a quality unit prior to dosing in a human clinical trial/

A barrier to delivering a third and potentially a fourth pulse from a single dosage form is the delay in drug release required, coupled with the location of the dosage form at 12 and 18 hours post-dose. As a multiparticulate dosage form is ingested and travels down the GI tract, the pellets or granules spread out in the intestine, starting with a variable gastric emptying event. As small groups of pellets leave the stomach, and spread out along the small and large intestine, they are be subjected to variable conditions, including pH and volume of media available for drug product dissolution. These variable conditions may lead to different populations of the multiparticulates releasing drug at different time, and may result in a weaker bolus. Development of a single, monolithic dosage form approach may address the multiparticulate pellet spread challenge.

Human Normal Volunteer Study

Up to four 12-hr release formulations are tested in man. A 12 mg Pulsatile Release (PR) is intended to provide 2 spikes over 12 hours. The Study is be a Bioequivalence Phase 1 study in 12 normal healthy normal males and females, who are non-smokers, or previous smokers who are currently non-smokers×3 months or social smokers who are willing and able to abstain from tobacco use for the duration of the study. We are using healthy normal volunteers to conduct the study, as the goal is to obtain the highest quality data with minimal interference from confounding factors. Healthy volunteer PK studies have been shown to be superior to PK studies in populations where extended overnight stays are challenging and compliance is low. For example, subjects who are ill may have a difficult time refraining from eating, and food may interfere with the interpretation of data.

Study Design

Comparative PK/bioavailability of immediate-release and four different 12-hr release formulations of nicotine:

Strength/Form (A) Immediate Release (IR) 6 mg q6 h×4 doses
(B) Pulsatile Release (PR) 12 mg Form 1 q12 h×2 doses
(C) Pulsatile Release (PR) 12 mg Form 2 q12 h×2 doses
(D) Pulsatile Release (PR) 12 mg Form 3 q12 h×2 doses
(E) Pulsatile Release (PR) 12 mg Form 4 q12 h×2 doses minimum concentration over the 24-hr interval, and half-life, is computed where possible. The main exposure parameters are compared statistically by an analysis of variance (ANOVA) according to the two, one-sided equivalence approach. Results are presented as the geometric mean ratio between the proposed modified-release nicotine regimens and the immediate-release formulation, with corresponding 90% confidence interval for the difference in means. Importantly, our team has extensive expertise in the use of nicotine in pre-clinical and clinical settings. The combined bioanalytical capabilities include method development, method transfer and an extensive compendium of assays including the most sensitive nicotine assay (LLOQ 0.2 ng/mL) on a global platform in the industry. Table 8 is a listing of the current nicotine assays available.

TABLE 8

Available Validated Bioanalytical Assays

| Compound Name | Technique | Species/Matrix | Range | Anti-coagulant |
|---|---|---|---|---|
| Nicotine; Cotinine | LC-MS/MS | Human Serum | 0.5-50 ng/mL; 1-200 ng/mL | N/A |
| Nicotine; Cotinine | LC-MS/MS | Human Plasma | 0.2-10 ng/mL; 1-100 ng/mL | EDTA |
| Nicotine, Cotinine | LC-MS/MS | Human Plasma | 1-50 ng/mL; 1-100 ng/mL | EDTA |
| Nicotine; Cotinine; trans-3'-Hydroxycotinine | LC-MS/MS | Human Plasma | 0.2-10 ng/mL; 1-100 ng/mL | EDTA, Heparin |
| Nicotine; Cotinine; trans-3'-Hydroxycotinine; Nicotine Glucuronide; Cotinine Glucuronide; trans-3'-Hydroxycotinine Glucuronide | LC-MS/MS | Human Urine | 10-1000 ng/mL; 10-1000 ng/mL 10-1000 ng/mL; 10-1000 ng/mL 20-2000 ng/mL; 50-5000 ng/mL | N/A |
| Nicotine; Cotinine; trans-3'-Hydroxycotinine; Nicotine Glucuronide; Cotinine Glucuronide; trans-3'-Hydroxycotinine Glucuronide | LC-MS/MS | Human Urine | 50-5000 ng/mL; 50-5000 ng/mL 50-5000 ng/mL; 50-5000 ng/mL 200-20000 ng/mL; 200-20000 ng/mL | N/A |

Each subject has a washout time of a minimum of 3 days prior to entering into the next period. The time of confinement include Day −1 through to AM of Day 2 (2 bed nights in each period).

Safety

Figure 12:
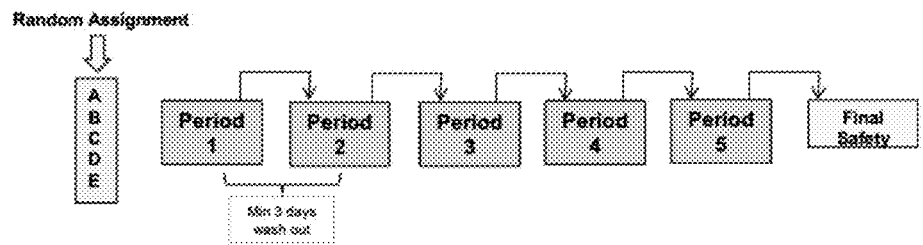
FIG. 12 illustrates a schematic of PK sampling schedule.

Safety assessments focuses on ensuring that all subjects entering the study are normal and healthy using a screening and pre-first-dose-vital Signs and Physical Exam, ECG and Standard Clinical Lab tests. During the study, close attention is paid to hemoglobin due to the large blood volume from PK sampling to ensure that subjects levels are within normal range at the beginning of each period and at the end of the $5^{th}$ period. PK Sampling: The PK Sampling Schedule is identical for each period and is as follows: Pre-dose (0 hr), 0.5, 1, 1.5, 2, 2.5, 3, 4, 6, 6.5, 7, 7.5, 8, 8.5, 9, 10, 12, 12.5, 13, 13.5, 14, 14.5, 15, 16, 18, 18.5, 19, 19.5, 20, 20.5, 21, 22, 24. See FIG. 12.

Analytical Assay and Statistical Analysis

Analyte(s): Nicotine and cotinine. Nicotine in plasma or serum, once quantified bioanalytically, is analyzed using descriptive statistics to summarize the concentration in samples by treatment and time point. Each individual subject, by treatment, concentration versus time profiles is analyzed using non-compartmental pharmacokinetic (PK) methods to derive the PK parameters of interest. Of main interest, is the peak (Cmax) exposure, overall systemic exposure (AUC) over a 24-hour period for the various treatment regimens. In addition, the time to peak (Tmax), Criteria for Success The benchmark of success for Phase 2 is the identification of a formulation of nicotine that can be given to patients once or twice daily and deliver a nearly identical PK profile as the dosage regimen of NP002 used in the Phase 2 study.

Example 13: Development of Nicotine Formulations

This project has the potential to dramatically change the quality of life for patients suffering from Parkinson disease (PD). PD is a neurodegenerative disorder that results from a progressive loss of dopaminergic neurons in the substantia nigra pars compacta. It affects 1.5% of the global population over 65 years of age. The lack of dopamine causes the classical motor symptoms of bradykinesia, rigidity and resting tremors. These symptoms are dramatically improved by current dopamine replacement strategies, which include levodopa (L-dopa), the precursor of dopamine and dopamine receptor agonists, as well as monoamine oxidase B (MAO B) inhibitors and catechol O-methyltransferase inhibitors. Dopamine replacement therapies greatly reduce Parkinson's symptoms and enable patients to lead relatively normal lives; however, after several years of continuous therapy, treatment with these agents is complicated by the onset of motor fluctuations and dyskinesia, which leads to alternating periods of reduced mobility, gait and balance abnormalities. Known as Levodopa induced dyskinesia or LID, this syndrome almost always occurs as a side effect of long-term therapy with levodopa. Dyskinesia is the term used to describe unintended, involuntary and uncontrollable movements, including twitches, jerking and twisting. Treating physicians are sufficiently concerned about the risk of LID developing in their patients that they often delay treatment with L-dopa or use suboptimal doses of the drug in an effort to delay the development of dyskinesias. However these tactics effectively remove the only effective PD therapy and are typically followed by an increase in bradykinesia, rigidity or tremors. Among the top priorities recommended to the National Institute of Neurological Disorders and Stroke (NINDS) Council as critical for Parkinson Disease (PD) research is the development of effective treatments for L-dopa-resistant features of PD. These include the development of effective treatments for abnormal PD associated motor symptoms such as dyskinesia as well as gait and postural instability leading to falls.

NC001, a 2-pulse, time released dosage form of nicotine (the active ingredient), mimics the pharmacokinetic (PK) profile of the formulation used in a successful Phase 2 clinical trial of nicotine (Randomized, Double-Blind, Parallel Group, Placebo Controlled Safety, Tolerability and Efficacy Study of nicotine in Subjects With Idiopathic Parkinson's Disease With Dyskinesias Due to Levodopa Therapy) in which drug ((nicotine) was administered every six hours. The results of the clinical trial showed a strong statistically and clinically significant benefit in reducing dyskinetic movements versus placebo. (NC001) may allow the delivery of nicotine as 4 doses spaced 6 hours apart, delivered orally no more than twice a day for a total of 24 mg/day. The formulation provides short-duration pulses of drug (total of 4 pulses daily) to the system, specifically so that the brain is free of nicotine for at least 4 hours between pulses. Two capsules a day should help assure patient compliance. This formulation is developed using pharmaceutical polymers in combination with organic ionic salts where the permeability is controlled through ionic interactions in the coating.

Impact

Injuries associated with falls plague PD patients both in terms of human suffering and economic losses. Annual fall incidence rates in PD range from 50-70% and recurrent falls are a major cause of disability. The resulting loss of independence and costs of treatment add substantially to the healthcare expenditures in PD which is estimated to be $27 billion annually. This will rise substantially in the coming decades as the population ages.

Therapies that are currently under development for PD—including both dopaminergic and non-dopaminergic compounds—are focused on improvement of motor fluctuations and reducing "off" times (when Levodopa wears off—a state of decreased mobility) without worsening dyskinesia or causing problems with impulse control, anxiety or depression. While reducing motor fluctuations is important for patients with PD, reduced motor fluctuations are aimed at reducing the "off" state, and are not aimed at reducing LID nor are they effective at reducing gait balance and falls. New drugs such as Rytari and Duopa were approved for reduction of "off" times. In the experience of physicians at the Parkinson Institute and Clinical center (PICC), patients treated with Rytari since its launch have improved "off" times as per the drug's label but their LID have persisted. Duopa, also launched last year, requires invasive interventions and many patients are not keen to continuously wear an infusion-based gastrointestinal pump. Physicians are reserving this invasive option for patients who are having significant challenges with "off" time due to poor absorption of L-dopa. These types of patients often have gastroparesis and other GI dysfunction due to destruction of the myenteric neurons as part of the disease. By bypassing the stomach, L-dopa is absorbed and "off" times are reduced. LID can be worsened with Duopa due to higher exposure to L-dopa. Careful titration is required. Finally, Deep Brain Stimulation (DBS) especially of the Subthalamic nucleus (STN), does alleviate dyskinesias and provides relief for about 5-7 years. Beyond the gradual loss of efficacy over time, a difficulty with this treatment is that implantation of the DBS device is an expensive and invasive procedure, with a small but definite risk of stroke.

Other products that help manage the motor symptoms of PD but do not reduce LID include dopamine agonists, which mimic the effects of dopamine in the brain, and include pramipexole (Mirapex), ropinirole (Requip) and, apomorphine (Apokyn). Not as effective in treating PD as L-dopa, these compounds are often used in combination with L-dopa to smooth the "off" and "on" effects of L-dopa. The MAO B inhibitors, which represent a different class of therapeutics, prevent the breakdown of brain dopamine, and include selegiline (Eldepryl, Zelapar) and rasagiline (Azilect). Catechol O-methyltransferase (COMT) inhibitors, principally Entacapone (Comtan), mildly prolongs the effect of L-dopa therapy by blocking an enzyme that breaks down the drug. Side effects include an increased risk of dyskinesia. Anticholinergics, such as benztropine (Cogentin) and trihexyphenidyl, were used for many years to help control the tremor associated with PD, but their modest benefits are often offset by serious side effects. A review article in Nature Drug Discovery states that there will be no groundbreaking therapies for PD that will change the market landscape until the genes or proteins that mediate the neurodegeneration of dopaminergic neurons in the substantia nigra are identified and disease-modifying candidates targeting these mutations are developed. Such a development is not expected to occur for at least another ten years. Therefore, the use of these medications to treat the motor symptoms of PD is likely to continue for many years.

Key Technology Objectives:

As described in the research strategy, medication compliance is a particularly challenging problem for people with PD. Medications that require a dosage regimen every 4-6 hours cause sleep disturbance and missed doses, which, in the case of PD, leads to increasing motor complications. This is well established in PD where 46% of patients were reported to be non-compliant with their medication. Therefore it is critical for us to develop a new formulation that provides the targeted PK profile with twice a day capsule, each delivering 2 pulses for a total daily dose of 24 mg.

The controlled release of a drug at the preferred absorption site optimizes delivery of the active ingredient within the therapeutic window, maximizing its therapeutic benefits. The side effects of nicotine are related to plasma $C_{max}$ and, therefore, spreading the total dose over 4 daily pulses blunts the $C_{max}$ and reduces the potential for side effects. Although patients are rarely troubled by LID during sleep, it is unlikely that the mechanism for LID is turned off during sleep. Therefore, a twice daily capsule that provides Q6H pulses of nicotine is a reasonable approach. This formulation allows for reduced dosing frequency in order to provide the same PK profile evaluated in the previous Phase 2 study. The first pulse from the drug capsule (consisting of 2 pulses) provides a traditional immediate release, intended to achieve rapid therapeutic effectiveness. This is achieved by layering the nicotine drug substance onto a pellet substrate of microcrystalline cellulose (MCC) in a fluid bed dryer fitted with a Wurster column insert for efficient application of the materials. A brand of the MCC spheres that is commercially-available is Celphere. The drug substance is sprayed onto the MCC pellets along with a soluble polymer that helps bind the nicotine to the pellet. This is then overcoated with an additional immediate-release polymer that can be purchased in different colors for aesthetics. A brand of commercially available aesthetic coating is Opadry.

The second pulse of the drug capsule (time released) is drug-layered with the nicotine and soluble polymer in the same manner as the immediate-release component. The delayed-release pulse also includes an organic acid salt in the drug layer such as succinic acid. The functional film coat, which is then applied to the drug loaded pellets, is comprised of a copolymer of ethyl acrylate and methyl methacrylate containing methacrylic acid ester with quaternary ammonium groups, and triethyl citrate as a plasticizer. The ratios of the polymers and organic acid modifier determine the time of drug release from the delayed-release component. Two commercially-available polymers appropriate for this use are Eudragit RL and Eudragit RS. The functional film coat for the delayed release component is also applied in a fluid bed dryer fitted with a Wurster column. The organic acid modifier interacts with the copolymer in order to create pores for the water to leach into the formulation, and eventually, for the drug to be released. Both populations of pellets can be filled into a capsule for administration, or blended with additional inactive ingredients and formed into a tablet. Both approaches have been used in commercial drug products and our team has direct expertise in these approaches.

The success of the NC001 development and commercialization project is made possible because of the close collaboration between our research and development group and internationally recognized leaders in the diagnosis and treatment of Parkinson's disease. Dr. Abe Lieberman, Co-Principle Investigator, is the Director of the Muhammad Ali Parkinson Center and the Movement Disorder Clinic of Barrow Neurological Institute at St. Joseph's Hospital and Medical Center, was the principle investigator of our phase 2 studies. Neurocea's team has decades of drug development experience. Dr. Azhir, Principle Investigator, has successfully worked with the FDA to design and direct small and large phase 1, 2 and 3 clinical studies. Neurocea's CMC team, as evidenced by the substantial data in our IB and IND filings, are experienced and expert in drug development. Neurocea's formulation advisors have a particular expertise with pulsatile formulation and also have decades of formulation experience. Xcelion has over 20 years of experience in formulation development of GMP materials for clinical trial material (CTM) drug products.

This 2-pulse, time released dosage form enables targeted drug delivery and improve disease management through better compliance and enhanced patient convenience. It provides a safe drug that does not desensitize the critical receptors and allows physicians to treat PD with the most effective L-dopa therapy regimen.

Product Development Process Required to Support the NDA

One of the great strengths of this project is that nicotine at the dose that we plan to commercialize has already been proven to be safe. As such, the opportunity for filing an NDA without additional preclinical safety pharmacology and toxicology or long term clinical safety data is feasible through the use of the 505(b)(2) pathway. This pathway may allow the utilization of data in the public domain to support the NDA. A 505(b)(2) is a new drug application that contains full safety and effectiveness reports, but allows some of the information required for approval to come from studies not conducted by or for the applicant. This method enables a shorter development path for new drugs leading to potential filing for an NDA in a fraction of the time and cost required by traditional paths. We have met with the FDA and we understand that we need a single confirmatory Phase 3 human study to support the NDA. The FDA also noted that the existing public domain data on the preclinical safety of nicotine is sufficient to support our NDA with the exception of the need for a 3 month repeat dose toxicity study for drug-drug interactions in animals. In addition to these requirements, a fully updated CMC section may also be provided to the existing IND. Based on Phase 2 data with nicotine, our original nicotine formulation, the effect size and the standard deviation are similar to those observed in phase 2. Therefore, we calculated that we need 140 patients in treatment and 140 in placebo groups (280 patients total), which is be sufficient (90% power) to detect a difference between NC001 and placebo in the UDysRS total score, assuming a two-sided two-sample t-test at the 5% level of significance. Sample size calculations were done based on the continuous outcomes. The mean change from baseline and standard deviation for each treatment group were calculated. The sample size calculations were done for 80% and 90% power. The first set of sample sizes is based on a one-sided alpha=0.05, and the second is a two-sided alpha=0.05. Sample sizes were calculated assuming a two-sample t-test. See Table 9.

TABLE 9

| Scale (Week 10 result; change from baseline) | Nicotine | | Placebo | | NC001: one-sided alpha = 0.05 | | NC001: two-sided alpha = 0.05 | |
|---|---|---|---|---|---|---|---|---|
| | mean | sd | mean | sd | 80% power | 90% power | 80% power | 90% Power |
| UDysRS part III | 5.2 | 6.33 | 2.5 | 4.33 | 102 | 140 | 130 | 172 |
| UDysRS walking | 4.4 | 5.46 | 0.8 | 5.00 | 54 | 74 | 70 | 92 |

Impact of Non-Commercial Considerations to the Overall Significance of the Project PD is characterized by a loss of nigrostriatal dopaminergic neurons. Nicotinic receptors are located in the striatum and peduculopontine nuclei. They are ligand gated ion channels that regulate the release of dopamine. These receptors are stimulated by nicotine and acetylcholine. The nicotinic receptor subtype is localized primarily on dopaminergic terminals which regulates dopamine release. Nicotine generally exerts its effect by acting at nAChRs for which multiple receptors exist throughout the body. As an approach to understand the receptors relevant for nicotine's anti dyskinetic effect, many nAChR subtype agonists have been tested in the clinic, but none of them have been found effective in treating LID (see below) nor have they had any effect on gait, balance and falls.

From a scientific point of view, successful treatment of LID with a 2-pulse (total of 4 pulses daily), time released dosage form nicotine formulation gives us new insights into the mechanisms underlying gait, postural instability, falls, and LID. It may provide us with a more accurate assessment of LID, and more importantly, we may have a safe and effective drug that, in addition to reducing LID, reduces falls and addresses a >$27 billion/year medical cost of complications in PD patient care.

Nicotine has been available as a drug product over-the-counter for many years. In addition, because of extensive anecdotal evidence, many neurologists have been convinced of nicotine's usefulness in the treatment of PD Market Analysis Among the top priorities presented to the National Institute of Neurological Disorders and Stroke (NINDS) Council as final recommendations of critical needs for PD research is to develop effective treatments for L-dopa-resistant features of PD. These include motor symptoms such as dyskinesia, gait and postural instability leading to falls. In the U.S., there are approximately 1.5 million Parkinson's patients. Injuries associated with falls plague PD patients both in terms of human suffering and economic losses. Annual fall incidence rates in PD range from 50-70% and recurrent falls are a major cause of disability. The resulting loss of independence and costs of treatment add substantially to the healthcare expenditures in PD which is estimated to be $27 billion annually. This cost will rise substantially in the coming decades as the population ages. An intervention that is cost effective in reducing falls will have major benefits for the entire community. In our phase 3 registration study, we will determine whether treatment with NC001 (when added to levodopa) in addition to reducing dyskinesia will improve gait, postural stability, and reduce falls. Occurrence of LID appears to be related to dose and duration of treatment with levodopa and severity and duration of disease. In addition, patients who develop PD at a younger age have an earlier onset and higher rate of LID. Based on the number of PD patients and the percentage of patients who suffer from gait, postural instability, dyskinesia problems and falls as stated in the references above, we conclude that there are approximately 750,000 PD patients with these problems and other L-dopa related motor symptoms in the United States. Internationally, the potential market is at least double the US market.

Figure 3:
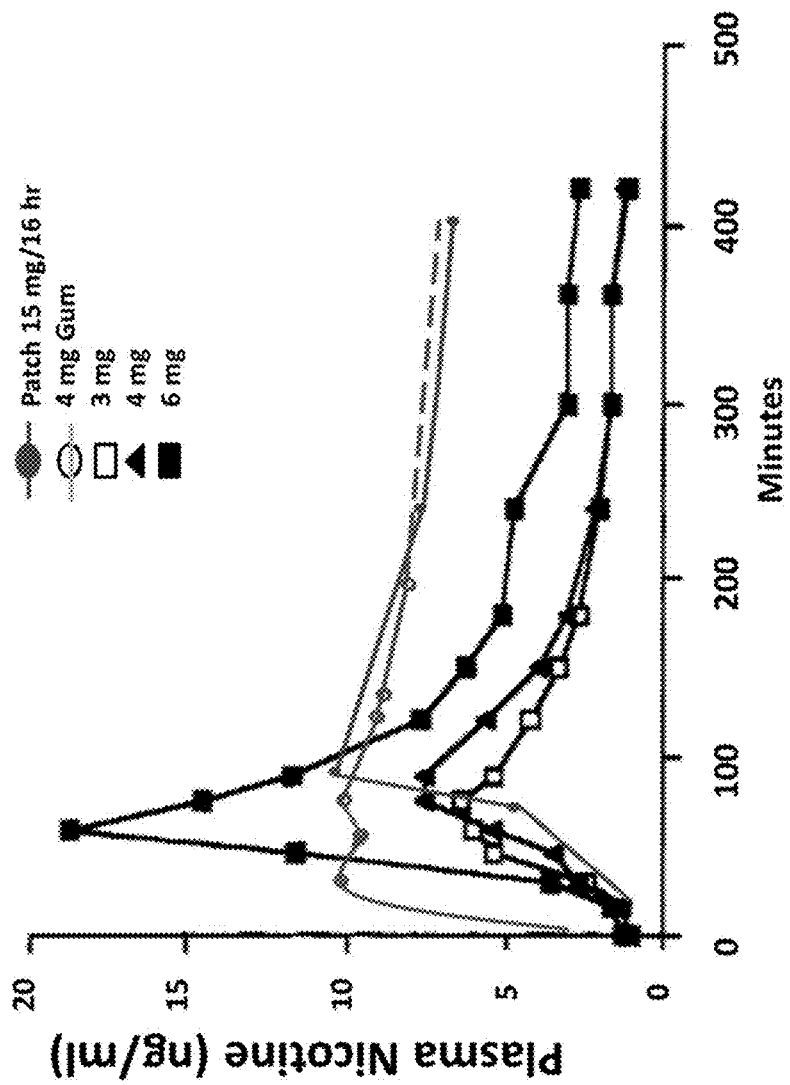
FIG. 3 illustrates a pharmacokinetic profile of different modes of administration of nicotine, including by transdermal patch (15 mg/16 hr), transbuccal gum (4 mg, assuming hourly administration), or oral tablet (3 mg, 4 mg, or 6 mg).

Physician Behavior:

Nicotine is currently available in many forms as aids for smoking cessation. These products are generally formulated to sustain the effect of nicotine over some period of time to provide lasting protection from cravings (see Research Strategy). These products (patch and gum) are generally formulated to deliver sustained and continuous blood levels of nicotine to provide lasting protection from cravings (FIG. 3). Nicotine, used this way, will result in desensitization of receptors and cause tolerance and dependence, and therefore will fail to provide sustained benefit for PD associated gait disorders. Nicotine tolerance may prevent the drug from being efficacious in the treatment of LID, NC001 is designed to provide short-duration pulses of drug to the system, specifically so that the nicotine will be nearly absent from the brain at least for 4 hours before the next pulse, thus preventing the receptor from becoming desensitized. NC001 achieves this profile, in particular, by timed release dosing, delivering 4 pulses 6 hours apart. In our testing, this has been shown to avoid the building of tolerance to nicotine, and there has been no indication of dependence when patients were withdrawn from therapy. These attributes are critical in formulating a successful nicotine product for the treatment of gait, postural instability, dyskinesia and fall reduction in PD and is used for years.

Development of Nicotine Formulations to Prevents Falls in Parkinson Disease (PD)

The major goal of the study is to validate a time release formulation of nicotine (NC001) that further decreases the likelihood of inducing desensitization and would increase patient compliance by changing the dosing from 4 to 2×/day dosing. This time release formulation encourages adherence in treatment especially important given that at the present time as many as 40-60% PD patients do not adhere to their L-dopa 3-4×/day dosing regimens.

We found that pulsatile administration of nicotine is critical for treatment of LID. Drug administration compliance is a critical issue for PD patients. As many as 40-60% of PD patients do not take their medications as prescribed. Therefore it is essential to simplify drug administration and develop a method of drug delivery that results in a far higher rate of compliance. Prior to the Phase 2 clinical trial of nicotine there was a lack of appreciation not only for the need to improve the safety profile of nicotine AND to ensure sustained efficacy without inducing desensitization, but also to develop a twice a day, modified dosage formulation to insure compliance.

The 2-pulse, timed released oral formulation of nicotine that delivers a total of 24 mg/day in two doses provides the needed exposure and blood profile; ensure maximal effectiveness, safety, and compliance while avoiding desensitization of receptors and building tolerance.

Studies described in humans below confirm that nicotine has significant anti-LID activity, but more importantly, nicotine significantly reduces symptoms associated with gait disturbances associated with falls in PD patients.

Preliminary Studies

Rationale for studying nicotine as a potential therapeutic agent for LIDs and PD associated gait disturbances: The rationale for using nicotine to reduce falls and dyskinesias stems from studies in rodents and monkeys rendered parkinsonian by 1-Methyl-4-Phenyl-1,2,3,6 Tetrahydropyridine (MPTP). In this model nicotine administered orally reduced LIDs through post-synaptic stimulation of nicotinic acetyl cholinesterase receptors (n-AChRs). This observation led to a study in PD patients with LIDs. A challenge with n-AChRs is they become rapidly desensitized with continuous exposure to nicotine and once desensitized, they lose their responsiveness. This can lead to withdrawal symptoms especially from continuous exposure utilizing nicotine patches. Nicotine is rapidly absorbed, has a short half-life and can be rapidly cleared (too rapidly with inhaled nicotine, making this route unsuitable). Thus in clinical trials a dosing regimen was used that provided short-duration pulses of orally administered nicotine after the agent is cleared from the blood from the previous pulse. Nicotine administered orally with a twice daily drug (4 short pulses) has a peak effect. Most of the drug is released within an hour (in each pulse), and the residual drug does desensitize the receptors. This results in the brain being free of nicotine for at least 4 hours, preventing the receptors from becoming desensitized, as occurs with the nicotine patch, which provides continuous exposure to nicotine.

Nicotine Reduces LIDs in Both Rodent and Primate Models

The initial basis for investigating the anti-dyskinetic potential of nicotine stemmed from initial basic research findings from studies in animal mode. In rats and mice, we found that nicotine reduced LIDs when administered by any one of several methods, including oral application, injection and slow-release mini pumps, with no decline in its efficacy over time. A critical discovery came when we also established that nicotine reduced LIDs in parkinsonian monkeys, the animal model that most closely mimics the motor deficits observed in PD. Nicotine (which binds and activates all nicotinic receptors) resulted in a 60% decline in LIDs in monkeys without worsening of parkinsonism (see FIG. 5 and FIG. 6). This reduction persisted for months, with no tolerance or loss of efficacy and no detectable side effects.

How can Nicotine be Administered Safely and Efficaciously to Humans for the Treatment of PD Associated LIDs Associated Gait and Balance Symptoms?

The neurobiological mechanisms underlying LIDs are not well understood. Extensive studies have implicated multiple neurotransmitter systems, including nicotine cholinergic receptors (nAChRs). There is extensive overlap in the organization and function of the nicotinic cholinergic and dopaminergic systems in the basal ganglia. Nicotine is known to influence dopamine release and alter dopamine-related motor behaviors in animals. Our finding that nicotine is effective in animal models of dyskinesia was only the first step to considering a path for a clinical use of nicotine. Nicotine is difficult to administer safely, and studies had suggested that rather high and sustained doses of nicotine were required for neuroprotection.

In parallel with the efforts to identify how to use nicotine in the clinic, the field had advanced substantially in its understanding of the biology of nicotinic receptors. A major challenge with nAChRs is that they become rapidly desensitized with continuous exposure to nicotine. NC001 is novel oral formulation of nicotine that was designed to be administered twice daily, delivery 4 short pulses of nicotine and not desensitize the receptors. Other formulations of nicotine (such as patch) are formulated to deliver sustained and continuous blood levels of nicotine, which causes desensitization of receptors. Once desensitized, these receptors lose their responsiveness to agonist drugs, and in addition, not all receptors desensitize at the same rate, for example, the cardiac receptors may desensitize more slowly than those in the brain. This leads to multiple problems with safety, addiction and withdrawal symptoms from continuous treatment with nicotine. We reasoned that it was critical to deliver the molecule in a way that avoids desensitization (see FIG. 3).

Nicotine is available in many forms as an aid for smoking cessation. These products are generally formulated to deliver sustained and continuous blood levels of nicotine to provide lasting protection from cravings. Nicotine has the potential to cause tolerance and dependence, but because it is prescribed as a short-term treatment, this is less of an issue. Therefore, it was critical to establish that nicotine could be delivered safely to PD patients being treated with multiple different types of dopaminergic therapies AND that a dose could be found that would be delivered in such a way that would be efficacious treating LIDs without causing tolerance and dependence.

Clinical Testing of Nicotine in PD Patients

Rationale: Given the data shown in FIG. 3 for our Phase 2 clinical trial we required a method of drug delivery that provided 4 short-duration pulses of nicotine to the system, specifically so that the nicotine would be cleared from the blood system before the next pulse. Fortunately, orally delivered nicotine is rapidly absorbed and has a very short half-life. We sought to capitalize on this property by developing an oral formulation that could be swallowed, rapidly absorbed and substantially cleared within about 2 hours. The timing between doses was 6 hours, an ample time to clear each dose so as not to desensitize AChR receptor function. We also hypothesized that this method of dosing might lead to an improved safety profile. Finally, we recognized that a formulation given every six hours, while not likely to be an optimal commercial formulation, would be sufficient to test our hypothesis that short pulses of nicotine would be clinically efficacious in PD patients and would allow us to titrate the dose upwards over several weeks and establish how to deliver the drug safely and efficaciously (please see attachment IND Module 2.3PQOs CMC details of formulation, clinical trial material and stability testing). As described below, our trial proved this hypothesis to be correct.

Phase 2 Nicotine Study in Patients with PD and LIDs
Clinical Trial Description and Safety Results This study was conducted under IND #105268 as a multi-center placebo-controlled, safety, tolerability, escalating dose, and exploratory efficacy study designed to be used as one of two studies to support regulatory approval for nicotine (NP002) for the treatment of LIDs. The safety and tolerability of nicotine in subjects with idiopathic PD was assessed by adverse events (AEs), safety, laboratory tests, physical examinations, electrocardiograms (ECGs), vital signs, and assessments of impulse control, nicotine withdrawal symptoms, and changes in primary parkinsonian symptoms using an escalating dose of nicotine delivered every six hours for 10 weeks. Efficacy was measured with the Unified Dyskinesia Rating Scale (UDysRS), a semi-quantitative assessment, FDA-validated instrument to assess gait, balance and dyskinesia in PD. A total of 65 patients, nicotine-naïve on levodopa with LIDs from several clinical sites were randomized. Following screening, patients were randomly assigned to nicotine administered orally or placebo in a 1:1 ratio 4 times a day in a blinded fashion. Dosing was begun at 1 mg every 6 hours to a final dose of 24 mg per day. Patients who tolerated a total daily dose of at least 16 mg per day continued in the study. Six patients in the nicotine group and 5 in the placebo group withdrew because of adverse effects, which were minor and reversible.

Subjects were maintained on 24 mg/day for 4 weeks. The subsequent taper phase (2 weeks total), beginning at visit 4 (Week 10), consisted of 9 days of drug taper and 5 days off drug prior to Visit 5 (final safety visit). All subjects had a follow-up phone call 1 week and 2 weeks after the safety visit. Subjects who tolerated 16 mg/day but who did not tolerate 24 mg/day due to nausea or vomiting, at the investigator's election, were allowed to drop down to the 16 mg/day dose level. No other down-titration was allowed. Importantly, a total of 65 subjects (35 in the Nicotine group and 30 in the placebo group) were randomized, and 48 subjects (25 in the Nicotine group and 23 in the placebo group) completed the study. After randomization, 17 subjects withdrew from the study (10 subjects in the nicotine group and 7 subjects in the placebo group). No subject withdrew before taking any study medication. The most common reasons for withdrawal were AEs (n=11; 6 subjects in the Nicotine group and 5 in the placebo group) and protocol violations (n=4; 2 subjects in the Nicotine group and 2 in the placebo group). In addition, there were no issues with impulsivity or withdrawal symptoms. Importantly, neither the UPDRS Part III nor the Hoehn and Yahr scales showed any worsening during the study (and showed slight improvement), demonstrating that there was no worsening of Parkinsonian symptoms. Therefore, it was clear that we had established a safe and well tolerated way to administer nicotine to nicotine naïve patients with PD who were being treated with dopamine agents (see attached CSR).

Phase 2 Clinical Trial Efficacy Evaluations: Nicotine is Efficacious for the Treatment of Gait, Postural Stability, and LIDs Given Every 6 Hours Nicotine was superior to placebo on ALL patient- and physician-rated assessments of efficacy, and achieved statistical significance in reduction of gait, balance and dyskinesia (FIG. 8 and FIG. 9). Statistically significant differences favoring nicotine compared to placebo were seen in dyskinesia disability (UDysRS part 3) and Walking (indicating improvement in gait and balance), the percentage of responders on the Lang-Fahn Activities of Daily Living (LF-ADL) scale and on the Patient Global Impression-Change (PGI-C) scale. There was a statistically significant difference between treatment groups in the number of LF-ADL responders (subjects with ≥25% reduction from baseline) at Visit 4 (Week 10) (p=0.0453). In addition, there was a statistically significant difference between treatment groups in the number of PGI-C responders (subjects with a score of 1, 2, or 3) at Visit 4 (Week 10) (p=0.0048). There were 21 (77.8%) PGI-C responders in the nicotine group compared to 9 (37.5%) responders in the placebo group. Corroborating this response, there was a statistically significant difference between treatment groups in the numbers of subjects in the different categories (1 through 7) of the PGI-C scale at Visit 4 (p=0.0230) Importantly, all scales designed to assess posture, gait and dyskinesia either were numerically and/or statistically significantly superior to placebo. In addition, using the UPDRS, we demonstrated that nicotine did not cause any worsening of the PD symptoms. In fact, there was a trend favoring nicotine compared to placebo. Therefore, we have established that nicotine delivered in pulsatile doses of 6 mg (every 6 hours) is efficacious and safe for the treatment of LIDs, and does not induce desensitization.

Summary of Clinical Testing:

In summary, this method of nicotine delivery avoids the building of tolerance(desensitization) and dependence on nicotine when patients were withdrawn from therapy. It is safe and it is efficacious for treatment of gait disturbances associated with PD and LIDs.

Nicotine was superior to placebo in all patient and physician rated assessments of efficacy. Nicotine was statistically superior to placebo in the Gait-subtest of the UDysRS, indicating improvement in gait and postural stability. Whether this is because of a primary improvement in gait and postural stability through cholinergic mechanisms in the striatum and brainstem (pedunculopontine nuclei) or whether it is secondary to a reduction in LIDs is, at present, unclear. This led us to conclude that nicotine delivered in pulsatile doses of 6 mg (every 6 hours) is a safe and well tolerated drug to use in PD patients who have LIDs and gait disturbances with greater likelihood of experiencing falls.

Approach:

The overall goal of this proposal is to develop a time release formulation of an oral formulation of nicotine previously shown to be efficacious in a phase 2 clinical trial for use in PD patient clinical trials for modulation of gait and balance abnormalities that lead to falls.

Rationale:

Nicotine's biopharmaceutical properties lend themselves to improved dosage formulations. Nicotine is available as a free base and in various salt forms. The nicotine bitartrate dihydrate salt is freely soluble in aqueous media across the physiological pH range and is commercially available as pharmaceutical grade material. Nicotine is absorbed across human tissues, including the skin. It is well-absorbed in the gastrointestinal tract, with an oral bioavailability of approximately 30% (20% to 40%) reported. These high solubility and permeability characteristics lend themselves to development of a 2-pulse, modified dosage form. The dosage form is a 12 mg form of nicotine that delivers a double-pulse of 6 mg nicotine 6 hours apart. This modified dosage form of nicotine taken orally twice daily is thus critical for developing a successful nicotine product for the treatment of gait, postural stability, dyskinesias and falls in PD. Such a drug should greatly increase patient compliance and improve the quality-of-life of PD patients. This is a fast track Phase 1-2 proposal.

Figure 13:
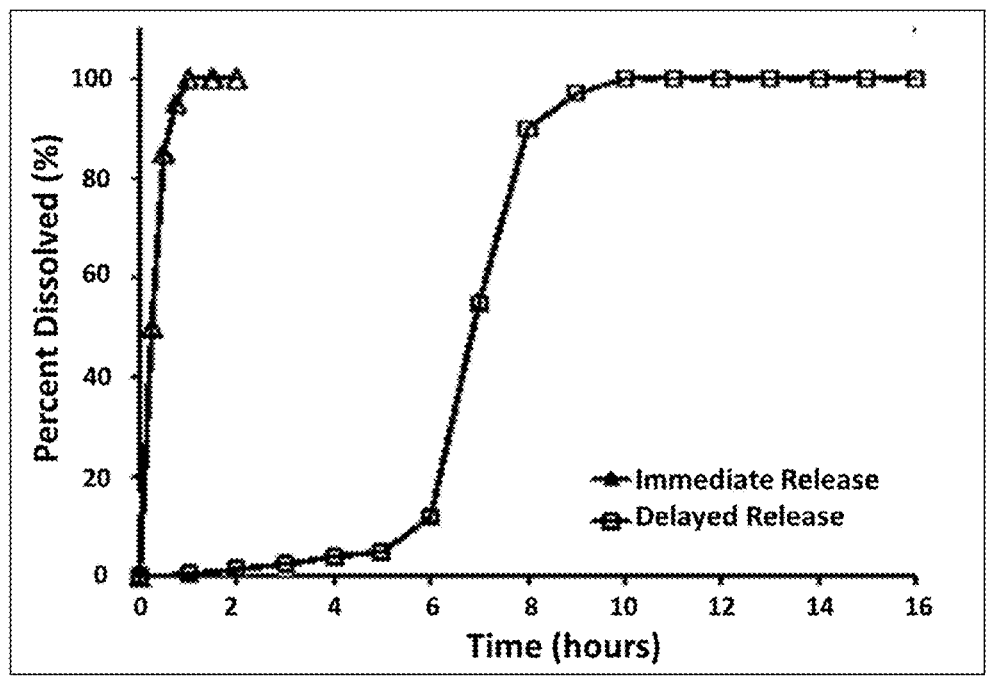
FIG. 13 illustrates a drug release profile for an immediate release (triangles) and delayed release (squares).
Figure 14A:
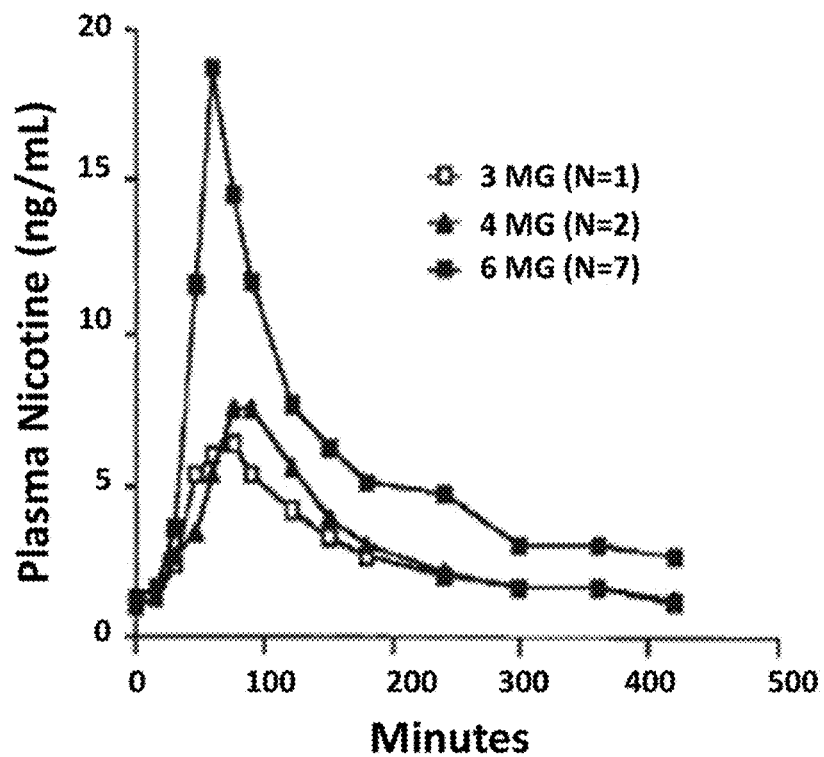
FIG. 14A illustrates a graph of single dose nicotine PK profiles.
Figure 14B:
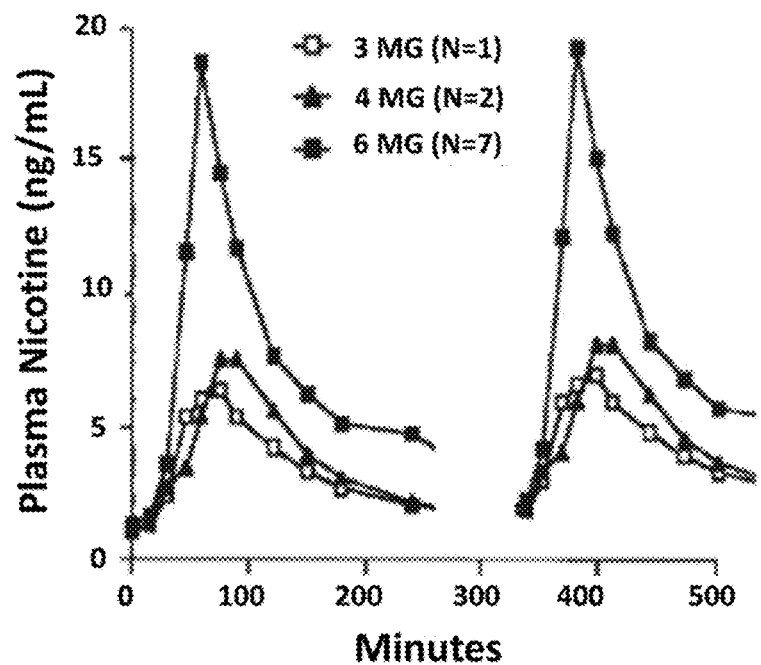
FIG. 14B illustrates a hypothetical nicotine PK profiles from a 2-pulse modified dosage form.

Phase 1:

Develop and select several multiparticulate immediate-release nicotine dosage forms that are coated with a semipermeable membrane that delivers an in vitro dissolution profile that delivers 2 pulses of nicotine spaced 6 hours apart. In the Phase 2 study (NCT 000957918), immediate release nicotine was administered every 6 hours which resulted in an improvement of UDysRS total, a measure of LIDs. Oral administration of capsules containing nicotine bitartrate results in rapid absorption with a $T_{max}$ of ~90 minutes (FIG. 6). By ~6 hours (360 min), the plasma concentration of nicotine returns close to baseline. The Phase 1 nicotine formulation is taken twice daily, every 12 hours. The goal is that this modified dosage form would immediately release a bolus of nicotine and then release a second bolus of nicotine approximately 6 hours later. FIG. 14B depicts the target nicotine PK profile after administration of a single capsule of the 2-pulse, modified dosage form. The prototype formulations generated in this Aim is tested using in vitro dissolution and the ideal drug release profile presented in FIG. 13. FIG. 13 illustrates a drug release profile for an immediate release (triangles) and delayed release (squares). The drug release profile indicated by the triangles exhibits an immediate release of the drug reaching complete dissolution within 1 hour of the start of the dissolution challenge. The delayed-release component, indicated by the squares, exhibits a similar release rate to the immediate-release, but the initial drug release is delayed by approximately 6 hours.

Phase 2,

Aim 2 tests the performance of up to three prototype 2-pulse modified dosage forms created in Phase 1, and GMP manufactured in Phase 2, Aim 1. Healthy volunteers are administered these formulations, and the ideal PK profile would be similar to that presented in FIG. 14A and FIG. 14B. FIG. 14A illustrates a graph of single dose nicotine PK profiles. FIG. 14B illustrates a hypothetical nicotine PK profiles from a 2-pulse modified dosage form.

As described above, the formulations generated in phase 1 are tested using in vitro dissolution testing. An example of the desired in vitro dissolution profile of the individual components and the composite is shown in FIG. 15.

Figure 16:
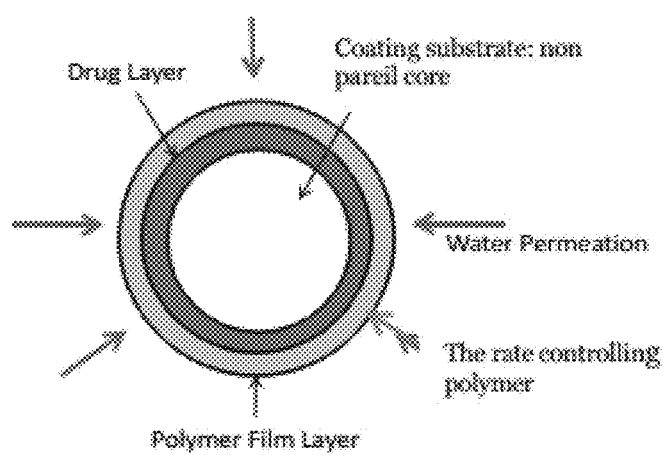
FIG. 16 is a second illustration of a pH independent core pellet dosage form. A coating substrate is shown with a rate controlling polymer layer (gray) on top of a drug contain layer.

The non pareil core shown in FIG. 16 is the substrate for application of the drug layer to the dosage form. The uniform size and shape of the core is ideal for drug layer mechanical strength, and drug product uniformity. The drug layer contains the active drug substance and a polymer to adhere the nicotine to the core pellet. The polymer film layer is the functional film coat that controls the dissolution of the nicotine from the drug product. The functional film coat slowly allows water to permeate into the core pellet, and the rate of this water intrusion is dictated by the film coat components and the thickness of the film coat. An example of a core pellet which is well suited is shown in FIG. 16.

Figure 15:
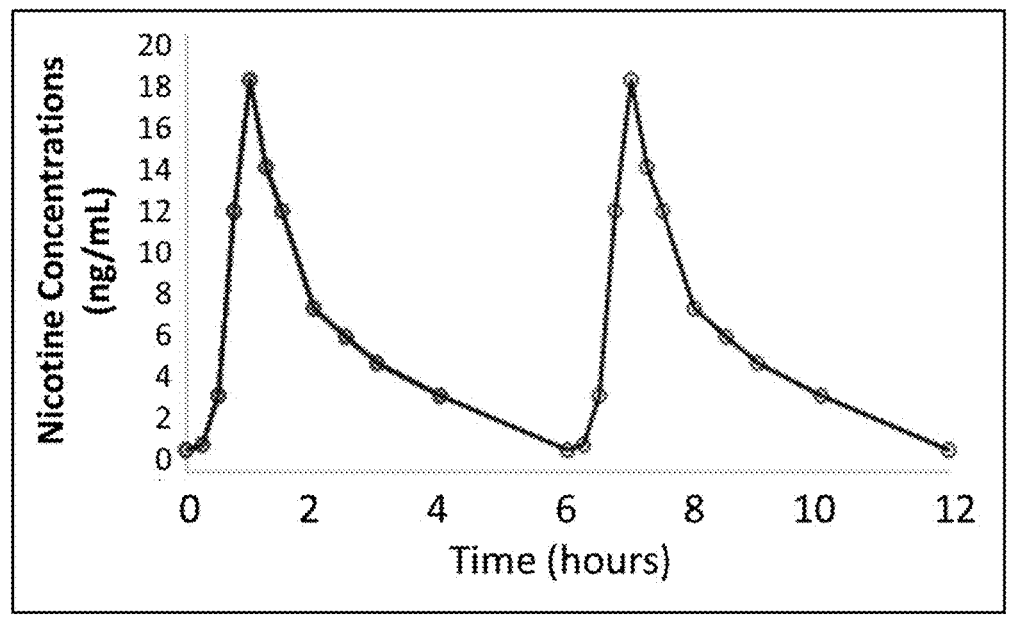
FIG. 15 is a graph of a target 2-pulse PK profile from a nicotine modified-release capsule, 12 mg (6 mg IR and 6 mg DR).

The target PK profile from the dissolution profiles shown in FIG. 13 is shown in FIG. 15.

Core Pellet Formulation:

A 15% solution of nicotine bitartrate dihydrate is prepared including hypromellose (HPMC) as a binder and succinic acid as the organic acid modifier (see section 2.3 of the IND CMC attached for more detail on drug substance). This solution is coated onto nonpareil seeds using a fluid bed dryer fitted with a precision coater apparatus until a 20% solids weight gain is achieved on the pellets. The drug layer on the core pellet formulation contains nicotine, HPMC, and succinic acid in a 5:3.5:1.5 ratio. If necessary, alternative levels of HPMC or binders may be used in order to improve the quality of the adherence of the drug layer to the nonpareil seed. The final drug layered pellet formulation is selected based on 1) visual observation of the pellets, 2) characterization of the drug content on the pellets relative to the target assay value and 3) the drug release characteristics of each formulation. The coating should be smooth and uniform under microscopic evaluation, resulting in good uniformity for the drug content in the dosage form. In addition, a smooth substrate for additional functional film coating is desired for efficient coating and acceptable adherence. The assay value should be within +/−5% of the target drug content. Both the visual and assay tests are indicators for quality of the manufacturing process. The drug release should be rapid from the core pellets, with a target of >85% dissolved by 15 minutes.

Immediate-Release Particle Formulation:

The core drug-loaded pellets is coated with an immediate release polymer such as Opadry for aesthetics and used as the immediate release component of the composite dosage form. The Opadry powder can be reconstituted as a suspension at about 10% for application onto the Core Pellet to manufacture the Immediate Release composition for the composite drug product. The suspension would be coated onto the Core Pellet formulation using a fluid bed dryer fitted with a precision coater as described above. This coating can be clear, white, or another color chosen for aesthetic purposes.

Modified Release Particle Formulation:

For the delayed release pellets, a separate population of the Core Pellets are further coated with a separate functional polymer film coat. An aqueous dispersion of Eudragit RS is prepared with triethyl citrate as the plasticizer and talc functioning as the antitack agent in a 6:1:3 ratio. This dispersion is coated onto the drug loaded pellets using a fluid bed dryer fitted with a precision coater to total solids weight gain of approximately 70%. The optimum weight gain is determined experimentally by using in vitro dissolution as the feedback mechanism. Formulations are selected for further evaluation based on their drug release profile. The formulations may be differentiated by: 1) Amount and/or type of organic salt included in the formulation to activate the release of the drug, 2) Weight gain of the polymer formulation on the Core Pellets, 3) Inclusion of swellable materials under the modified release polymer film coat and 4) Alternative polymer materials such as Eudragit RL.

The amount of organic salt can impact the rate at which the polymer hydrates to allow water intrusion into the formulation. The polymer weight gain also serves to modify the rate of water intrusion, as well as the strength of the film coat. A thicker coating results in slower water uptake and a delayed drug release due to the strength of the film coating. Swellable materials can be added to increase the pressure on the film coat to speed the drug release. Other polymers may be used to modify the permeability characteristics of the film coat. Adding Eudragit RL increases the permeability of the film coat relative to Eudragit RS, increasing the water uptake rate and reducing the lag time of the drug release. These formulation materials and conditions may be utilized to modify the lag time or release rate of the nicotine from the modified release pellets.

Composite, Multi Particulate Drug Product:

The immediate release and modified release components particles are filled into small size (#3) capsule shells. Length of the lag time and strength of the drug release can be tailored based on coating formulation and coat weight gain.

Formulation Evaluation:

Initial formulation development experiments are conducted on small, laboratory scale equipment with small batch sizes (10-50 g/batch). These batches are manufactured at laboratory or benchtop scale, and manufacturing instructions and conditions are documented in a notebook. This material is suitable for in vitro testing but not for clinical use. Formulation prototypes are evaluated using several approaches, including evaluation of content, impurities, uniformity of dosage units, and in vitro drug (nicotine) release rate. Other quality attributes such as water content and microbiological content are evaluated. Stability testing can be supported by excipient compatibility studies, but is demonstrated on the actual drug product at room temperature (25° C./60% RH) and accelerated (40° C./75% RH) conditions. The stability program evaluates the physical stability of nicotine (assay and related substances) and the performance of the dosage form (appearance and dissolution).

Dissolution Testing:

Dissolution testing is the industry standard for evaluation of release rate used during development to assess the performance of both the immediate release particles, the modified release particles as well as the prototype capsule formulations. The dissolution sample concentration is measured using HPLC with UV detection similar to what was used for release and stability testing of the clinical materials previously evaluated in the Phase 2 study (see attached IND section 2.3PQOS Assay, Content Uniformity and Related Substances of Nicotine in Nicotine Capsules by HPLC AC-AM-00337 for original methods, although more refined methods are now available). If the initial prototypes do not meet the target profile, the formulation development process becomes iterative, using the feedback from the first round of development to guide the formulation modifications. Prototype formulations are evaluated for drug release in dilute HCl media, pH 1.1 to mimic the fasted stomach conditions, as well as pH 6.8 buffer to mimic the intestinal conditions. In addition, the lead prototypes are also evaluated in simulated intestinal fluids (FaSSIF and FeSSIF), as well as pH 4.5 acetate buffer to mimic the fed stomach. The formulation approach is designed to perform independently of media pH, resulting in minimal food effect on the PK resulting from administration of the dosage form.

Formulation Selection Criteria for Success

Figure 17:
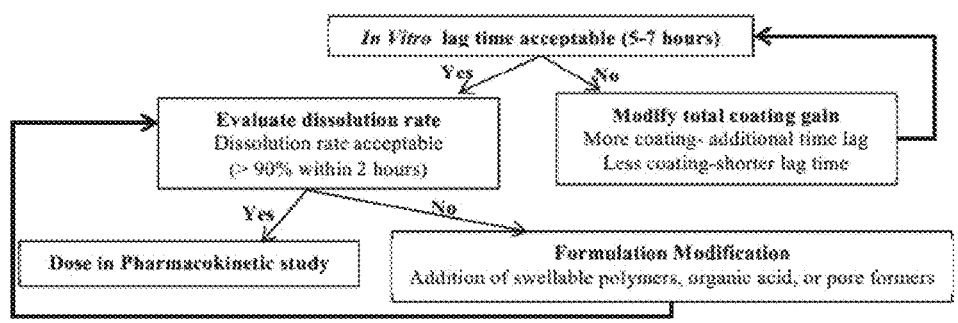
FIG. 17 illustrates a decision tree for evaluation of in vitro dissolution performance of nicotine delayed.

Modified Release Particle Evaluation:

A delayed release formulation releases at least 90% of the labelled amount of nicotine over approximately 30-45 minutes beginning 6 hours after the first release. 10% residual drug does not desensitize the receptors. Since nicotine is cleared rapidly, this method of administration of nicotine results in the brain being free of nicotine for at least 4 hours, preventing the receptors from becoming desensitized. The target goal is to minimize the amount of leak in the delayed-release formulation, and maximize the rate of drug release once the release is initiated. This results in a strong pulse of drug release and is intended to perform similarly to the immediate-release dosage form that is administered 6 hours after the first dose. The modified release formulation is evaluated by the amount of drug released at 6 hours (the leak) and how quickly the entire dose of the drug is released once the drug release is initiated. The nicotine concentration is measured in samples of the media removed from the dissolution vessel over time and injecting the sample onto a High Performance Liquid Chromatography (HPLC) system with UV detection. The amount of nicotine released is measured as a percentage of the target drug load in the dosage form (i.e., 4 mg of drug released from an 8 mg total dose would provide a 50% dissolved result). The in vitro dissolution performance of the nicotine delayed release formulation is evaluated according to the decision tree shown in FIG. 17. Each formulation prototype is evaluated against these criteria and identified for PK study dosing or modified to meet the dissolution lag time and release rate criteria.

The formulations that meet the evaluation criteria from the in vitro dissolution test are carried forward into in vivo pharmacokinetic testing in humans. The in vitro dissolution test may not exactly correlate with the in vivo performance in humans; therefore 3 prototype formulations are evaluated in the initial PK study. These formulations differ in targeted lag time and the qualitative composition of the functional film coat. The levels of swellable polymer pore formers and organic acid are modified to evaluate which combination provides the most rapid in vivo dissolution. Understanding the interaction of these components is key to designing and selecting the final drug product prototype for advancement into clinical trials.

GastroPlus Modeling:

Another tool that can be used for evaluation and understanding of formulation performance is GastroPlus. GastroPlus is a commercially-available modeling and simulation software program based on Advanced Compartmental Absorption and Transit (ACAT) model. This is a physiologically based PK model that can provide understanding of in vivo performance of formulations, including in vivo dissolution and absorption. Impact of active transport across the intestinal wall, changes in motility, and drug metabolism can also be included in the model. Models can also be developed based on the fed or fasted stomach for a thorough knowledge of the impact of food on the formulation performance. The inputs to the model are: drug substance, physical and chemical characteristics and formulation dissolution rate. PK data from IV dosing, oral solution, or immediate release formulations are also useful to develop the model. The FDA actively encourages use of GastroPlus in evaluation of clinical pharmacology and biopharmaceutical performance of applicants' NDAs.

Phase 2 Aim 1: Manufacturing of GMP Clinical Trial Material:

Four formulations (nicotine and the three prototype formulations identified in the phase 1) are manufactured under GMP guidelines for the human study. This work is conducted at Xcelience in Tampa, Fla. Xcelience has over 20 years of experience in formulation and analytical method development, as well as manufacture and distribution of GMP materials for Phase 1 and Phase 2 studies. Importantly, they have direct experience with nicotine formulation development activities. The investigators have worked directly with Xcelience to commercialize similar dosage form products. The manufacturing parameters are further developed for the manufacturing scale equipment, and these experiments is documented in a laboratory notebook In vitro dissolution testing is not always predictive of in vivo performance. As a multiparticulate dosage form is ingested and travels down the GI tract, the pellets or granules may spread out in the intestine, starting with a variable gastric emptying event. As small groups of pellets leave the stomach, and spread out along the small and large intestine, they may be subjected to variable conditions, including pH and volume of media available for drug product dissolution. These variable conditions may lead to different populations of the multiparticulates releasing drug at different times, and that could result in a weaker bolus. This potential effect could provide a barrier to a strong bolus release at the targeted interval (12 or 18 hours post-dose). However, once we have the human PK data, we can develop a better In vivo/In vitro Correlation (IVIVC) for a second round of formulation development. We have budgeted for this possibility.

Human Normal Volunteer Study:

The pulsatile formulation of nicotine requires an immediate release (IR) component as well as a 6 hour delayed release (DR) component. The relative absorption of both components (IR and DR) needs to be similar. This depends on the nature and transit in the GI tract. Although preliminary data could be obtained in rat or monkey, gastric emptying and intestinal transit/absorption are sufficiently different in rat and monkey compared to human. Therefore, a simple cross-over PK study in human would provide rapid and definitive information about the performance of the formulation. A 12 mg, 2-pulses (6 mg each), modified dosage formulation delivered twice/day is intended to provide 2 spikes over 12 hours. The side effects of nicotine are related to plasma $C_{max}$. Spreading the total dose over 4 daily administrations blunts the $C_{max}$ and potentially reduces the potential for side effects. Although patients are rarely troubled by LIDs during sleep, it is unlikely that the mechanism for LIDs is turned off during sleep. Therefore, a twice daily capsule that provides Q6H pulses of nicotine is a reasonable approach that covers the waking day, when dyskinesias are most prominent and disabling and "allow" the receptors to become "resensitized" overnight. The study is a Bioequivalence Phase 1 study in 12 normal healthy males and females, who are non-smokers, or previous smokers who are currently non-smokers×3 months, or social smokers who are willing and able to abstain from tobacco use for the duration of the study. We are using healthy normal volunteers to conduct the study, as the goal is to obtain the highest quality data with minimal interference from confounding factors. Healthy volunteer PK studies have been shown to be superior to PK studies in populations where extended overnight stays are challenging and compliance is low. For example 2 subjects who are ill may have a difficult time refraining from eating, and food may interfere with the interpretation of data. Since the gastric empty effect varies from patient to patient, each patient acts as their own control.

Study Design:

Comparative PK/bioavailability of immediate-release and 2-pulse, modified dosage forms:

Strength/Form:

A) Immediate Release (IR) 6 mg q6 h×4 doses

B) 2-pulse, modified dosage form (PR) 12 mg prototype Form 1 q12 h×2 doses

C) 2-pulse, modified dosage form (PR) 12 mg prototype Form 2 q12 h×2 doses

D) 2-pulse, modified dosage form (PR) 12 mg prototype Form 3 q12 h×2 doses

Each subject has a washout time of a minimum of 3 days prior to entering into the next period. The time of confinement include Day 1 through to AM of Day 2 (2 bed nights in each period).

Safety:

Safety focuses on insuring that all subjects entering the study are normal and healthy, using a screening and pre-first-dose Vital Signs and Physical Exam, ECG and Standard Clinical Lab tests. During the study, close attention is paid to hemoglobin due to the large blood volume from PK sampling to ensure that subjects' levels are within normal range at the beginning of each period and at the end of the 5$^{th}$ period.

Figure 18:
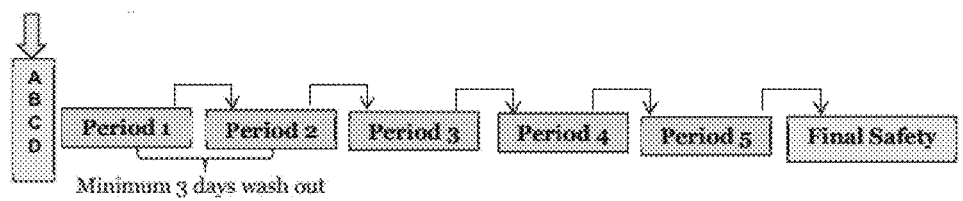
FIG. 18 illustrates a schematic of PK sampling schedule.

PK Sampling:

The PK schedule is identical for each period and is as follows: Pre-dose (0 hr), 0.5, 1, 1.5, 2, 2.5, 3, 4, 6, 6.5, 7, 7.5, 8, 8.5, 9, 10, 12, 12.5, 13, 13.5, 14, 14.5, 15, 16, 18, 18.5, 19, 19.5, 20, 20.5, 21, 22, 24. See FIG. 18.

Random Assignment

Analytical Assay & Statistical Analysis:

Analyte(s): The combined bioanalytical capabilities include method development, method transfer and an extensive compendium of assays, including the most sensitive nicotine assay (LLOQ 0.2 ng/mL) on a global platform in the industry.

Once quantified, nicotine concentrations in plasma or serum are summarized, by treatment, at each time point using descriptive statistics. Each individual subject's concentration versus time profiles are analyzed by treatment using non-compartmental PK methods to derive the PK parameters of interest. Of primary interest are the peak ($C_{max}$) exposure and the overall systemic exposure (AUC) determined over the overall 24-hour dosing period and within each of the four 6-hour intervals (0-6 hr, 6-12 hr, 12-18 hr, and 18-24 hr). The shape of the curves are compared in addition to several other parameters. Additional parameters to be measured include: the time to peak ($T_{max}$) (24-hour overall and within each 6-hour interval), minimum concentration over the 24-hr interval (Cmin), and half-life (T½). Exposure parameters are compared statistically by an analysis of variance (ANOVA) according to the two one-sided equivalence approaches. Results are presented as the geometric mean ratio of the parameter values for the comparison between each of the proposed modified-release nicotine regimens and the immediate release formulation, with a corresponding 90% confidence interval for the difference in means. Importantly, the team has extensive expertise in the use of nicotine in pre-clinical and clinical settings and expertise in the analysis of PK data.

Criteria for Success:

The benchmark of success for Phase 2 is the identification of a formulation of nicotine that can be given to patients twice daily and deliver a nearly identical PK profile to the immediate release dosage regimen of nicotine used in the Phase 2 study. The curves are compared visually in addition to review of the statistical outputs. "Targeted" PK profiles in Bioequivalence Studies can be identified using LC-MS with human serum, plasma, and urine. The PK is reviewed within the overall 24-hour dosing interval, including $C_{max}$, $T_{max}$, AUC0-24, Cmin and T½, and within each 6-hour "pulse" dose, including $C_{max}$ 0-6, $T_{max}$ 0-6 and AUC0-6, $C_{max}$ 6-12, $T_{max}$ 6-12 and AUC6-12, $C_{max}$ 12-18, $T_{max}$ 12-18 and AUC12-18, $C_{max}$ 18-24, $T_{max}$ 18-24 and AUC18-24. Immediate and late exposure to nicotine from the 2 doses of each of the 4 test pulse formulations are evaluated relative to the 4 doses of the IR reference formulation in each of the 6-hour intervals and overall for the corresponding exposure parameters. Other calculations that can be used to determine if there is a close match exposure from 4 unique IR intervals given every 6 hours. For example, based on the data, it may be more appropriate to evaluate similarity within each interval, either using the default bioequivalence (BE) criterion (for "identical" profiles) or another pre-specified criterion ("similarity" profiles) such as 90% Confidence Intervals (CIs) around the ratios of geometric least-squares means (GMR) for the comparison of each time-matched $C_{max}$ and AUC between test Form 1, 2, 3 or 4 versus the IR formulation contained within the standard BE boundary of (0.80, 1.25). However, a wider CI may be considered justifiable from safety and efficacy prospective: i.e. (0.7, 1.43) if we were to define success as having peak and overall exposures in each of the 4 intervals within ±30% of the IR exposure (matched interval). In addition, because we are evaluating 2 pulses of drug release from each test formulation, an immediate release pulse and a 6 hour delayed release pulse, the early vs. late release characteristics are compared within each test formulation using nonparametric comparison of relative $T_{max}$ values (e.g. both AM and PM doses combined, as $T_{max}$ from late release ($T_{max}$ 6-12 and $T_{max}$ 18-24) vs early release ($T_{max}$ 0-6 and $T_{max}$ 12-18) for a given formulation).

Example 14: Effect of NC001 a Central Cholinergic Agonist on Gait, Postural Stability, Dyskinesias and Fall Reduction in Parkinson Disease (PD)

Study Objective

The main objective of this study is to determine whether treatment with NC001 ((formerly NP002), Nicotine Bitartrate) versus placebo in addition to dopaminergic drugs will, in addition to reducing dyskinesias, improve postural stability and reduce falls. This will be achieved by demonstrating improvement in the motor portion of the Movement Disorder Society-Unified Parkinson Disease Rating Scale (MDS-UPDRS) and selected subtests of the MDS-UPDRS in either "on" or "off" or both "on or off" periods. The subtests will include the "Gait," the "Pull test," and the "Freezing of Gait" (FOG) sub-tests. These will be supplemented by selected subtests of the Barrow Neurological Institute (BNI) Balance Scale including "Standing on One Leg," "Turning," "Tandem Gait," "Step Length," and "Velocity." Since there are limitation to these semi-quantitative sub-tests in assessing gait and postural stability, these tests will be complemented by quantitative tests at home and in the clinic. All tests in the clinic will be performed with the patients wearing IMUs. This will allow us to correlate information from the semi-quantitative subtests of the MDS-UPDRS and BNI Balance Scale in both "on" and "off" periods with information from the quantitative IMUs.

The above information will be completed by information on static and dynamic balance in "on" and "off" states utilizing the Neurocom Equitest and by information from actual falls in both "on" and "off" states utilizing the Slip-Simulator. Patients undergoing Neurocom Equitest and Slip Simulator testing will wear IMUs. This will enable us to correlated information from static and dynamic balance testing and actual fall testing with information from the IMUs with a goal of developing a wearable sensor that can predict falls.

Testing in the clinic will be complemented by testing at home that will include 3 days of monitoring utilizing the same wireless IMUs utilized in the clinic. The IMU technology incorporating accelerometers and gyroscopes will assess gait, static and dynamic stability, dyskinesias and energy expenditure. This will be corroborated by a 3-day standardized diary documenting dyskinesias and falls. IMUs may provide an accurate assessment of the severity and percent time occurrence of dyskinesias than current methods. 6 months of NC001 supplementation may improve gait and postural stability, reduce falls, and reduce LID.

Study Design

We propose a Phase II single center, double-blind, randomized, placebo-controlled, cross-over, efficacy, safety, and tolerability study. The study includes a target enrollment of 40 male and female patients with typical PD with recurrent falls (>2 per year). Approximately 30% of these patients, 12 patients, will have LID. Patients will be administered NC001 or placebo in a 1:1 ratio as an oral capsule 4 times a day in a blinded fashion for 6 months, and then after a crossover for another 6 months. Prior to supplementation an initial base-line evaluation will be conducted. Afterwards, study will consist of evaluation every 2 months for 6 months, a cross-over, and then an evaluation every 2 months for 6 months. Efficacy will be measured with a set of stability, posture, gait, and activity measures that have been linked to fall risk including the Neurocom System, wearable sensors with accelerometers and gyroscopes and the Slip-Simulator.

This study will give us new insights into the mechanisms underlying gait, postural instability, falls, and LID. It will provide us with a more accurate assessment of LID. An assessment useful for studying other means of reducing dyskinesias such as deep brain stimulation. Approximately 30% of patients will have LID, 70% will not. As LID occur when patients are in an "on" state, and not in an "off" state, an improvement in gait (measured by IMUs), an improvement in static and dynamic postural stability (measured by the Neurocom Equitest), and a reduction in falls (measured by the Slip Simulator) in the 70% of patients without LID and the 30% of patients with LID in their "off" state, when all patients are without LID, will establish whether the improvement in postural stability and reduction in falls is a primary effect of NC001 or a secondary effect (through reduction in LIDs). Such a distinction would imply separate and distinct cholinergic mechanisms for fall reduction versus LID reduction. This in itself would be an important observation.

Study Population

Number of Subjects

This study will be an interventional one in which 40 people with PD (please see sample size determination) for ≥5 years or more, who have impaired postural stability and have fallen ≥2 a year, will be randomly assigned to NC001 or an identical placebo in addition to their regular PD dopaminergic medication. All patients will be on levodopa/carbidopa. They may be on additional dopaminergic drugs including dopamine agonists and/or monoamine type B oxidase inhibitors. All or most of these patients may have response fluctuations: "wearing off" Some patients will have freezing of gait (FOG). Approximately 30% of patients will have LID.

Inclusion/Exclusion Criteria

Participants will be screened from a patient population from the Muhammad Ali Parkinson Center part of the Barrow Neurological Institute, St. Joseph's Hospital and Medical Center.

Inclusion Criteria:

Patient has voluntarily signed and dated an informed consent form (ICF), approved by an Independent Ethics Committee (IEC)/Institutional Review Board (IRB), and provided Health Insurance Portability and Accountability Act (HIPAA) (or other applicable privacy regulation) authorization prior to any participation in the study.

Patient is male or female and is ≥30 and ≤83 years of age.

Hoehn and Yahr Stage II, III in an "on" state.

Fell >2 in past year.

Montreal Cognitive Assessment (MOCA) score≥24.

Stable dose of levodopa, dopamine agonist and/or monoamine oxidase B inhibitor, amantadine i.e. unchanged for 3 months.

Patient is ambulatory and able to walk ≥10 meters with/without the use of an assistive device.

Exclusion Criteria:

Patients with atypical Parkinson disorders that while infrequent, result in a high number of falls especially early in the disease. These include: Progressive Supranuclear Palsy (PSP), Multiple System Atrophy (MSA), Primary Freezing of Gait (PFG), and Corticobasal Degeneration.

Patients with dementia MOCA≤23. Although dementia is part of PD and can be a risk for falling, more than half of our patients with PD and dementia are without a caregiver for at least 4 hours and we're uncertain if they report all their falls.

Patients with a drop in blood pressure≥systolic (20 pts) and diastolic (10 pts)

Patients with major orthopedic problems of their hips or knees, and patients who needed hip or knee replacements.

Patient with schizophrenia, a schizo-affective disorder or a bipolar disorder.

Patients with hallucinations, psychoses or delusions.

Patients with a history of recent stroke or myocardial infarction

Patients with a known sensitivity to nicotine or nicotine-containing products.

Patients taking any of the following medications or substances within a minimum of 30 days prior to first dose: any form of nicotine, Cytochrome P450 2A6 (CYP2A6) inducers or inhibitors during the course of the study or within 30 days of the planned initial dose of study drug, neuroleptics, anticholinergics (with the exception of inhaled anticholinergics, e g, ipratropium, tiatropium), or stimulants Apomorphine due to its contraindication with ondansetron (used to treated nausea that may, initially, accompany administration of nicotine.

Warfarin

Study Procedures

Patients will undergo testing to quantitatively assess gait, postural stability and falls including the Neurocom to assess static and dynamic balance, the Slip Simulator, to assess reactions to an actual fall, and wearable sensors to assess gait, postural stability and dyskinesias in the clinic and at home.

Patients will be seen at baseline, 2 months, 4 months and 6 months. At each visit they will undergo "on" and "off" testing, as well as blood pressure monitoring. After six months, with each patient serving as their own control, patients on NC001 will be changed to placebo, and patients who were on placebo will be changed to NC001. After the cross-over, and a "washout" and re-titration is completed, all patients will be will undergo evaluation in both "on" and "off" states. The patients will then be seen at 2 months, 4 months and 6 months, and initial visits as before.

Administration and Titration of NC001

Parkinson disease is characterized by a loss of nigrostriatal dopaminergic neurons. Nicotinic receptors are located in the striatum and peduculopontine nuclei. They are ligand gated ion channels that regulate the release of dopamine. These receptors are stimulated by nicotine and acetylcholine. The nicotinic receptor subtype is localized primarily on dopaminergic terminals which regulates dopamine release.

NC001 or placebo in a 1:1 ratio will administered as an oral capsule 4 times a day in a blinded fashion for 6 months, and then after a crossover for another 6 months. During the double-blind treatment phase dosing will be begun at 1 mg every 6 hours, total daily dose 4 mg and escalated upward at 2 week intervals as follows:

2 mg every 6 hours total daily dose 8 mg for 2 weeks
Four mg every 6 hours total daily dose 16 mg for 2 weeks
Six mg every 6 hours total daily dose 24 mg thereafter.
Nausea, if present, will be treated with ondansetron.

Patients will be maintained on this dose for the duration of the study (6 months) until the cross-over. Because patients who are on placebo will not have been exposed to nicotine, the original escalation schedule will be repeated. A two week washout period at crossover, will consist of a 9 day taper and 5 days drug free. The taper is the reverse of the escalation at a rate of every 3 days as follows:

16 mg for 3 days
8 mg for 3 days
4 mg for 3 days

Schedule of Tests

All patients at each visit will be questioned on fall frequency and severity, they will be instructed to call if they fall. All patients whether they call or not will be called once a week and questioned about falls. In clinic measures will consist of the motor portion of the UPDRS in both an "on" and "off" state including the subtests of "Gait", "Freezing of Gait" (FOG), and the "Pull test." Measures will consist of subtests from the BNI Balance Examination including the "One Legged Stance Test", "Turning 360 Degrees", "Tandem Gait", "Step Length and Velocity" after walking 10 meters. Step length and velocity will be corrected for patient height and calculated from wearable sensors. Testing will consist of utilizing the Neurocom Equitest with patients in an "off" and "on" state. The Neurocom Equitest is used to assess motor control time (MCT) a measure of reactivity to a perturbation. Testing will consist of walking and slipping on the Slip Simulator in both "on" and "off states. During all testing in the clinic patients will wear an IMU. This will allow us to correlate information from our semi-quantitative clinical tests, our information from the Neurocom Equitest, and our information from the Slip Simulator with information from the IMUs. This may lead to the development of a single, simple wearable device that will monitor gait, postural stability, and dyskinesias and falls.

At home measures will consist of monitoring patients utilizing wearable sensors incorporating accelerometers and gyroscopes. These sensors provide information on gait, postural stability, falls and dyskinesias. The information from the sensors will be correlated with standardized 3 day diaries.

Withdrawal

Participants are free to withdraw from the study at any time and for any reason. Should the researchers determine that the participant should be removed from the study, the participants will be thanked and excused and will be provided with pro-rated compensation.

Analytical Methods

Pathological changes in walking, postural stability and, postural transition patterns and durations can be used as an indicator of health/fall-risk status. The use of wearable sensors, Inertial Measurement Units (IMU) reduces the human source of error in gait/postural timing events and is well suited for the current research. We have tested concurrent validity of IMU based system measuring time events and transition phases in walking and sit-to-stand postural movements against those taken from 3-dimensional motion capture system. Wavelet de-noising of IMU signals highlighted postural events and transition durations that further provided clinical information on postural control and motor coordination. Moreover, IMU can be efficiently used in monitoring of an individual's daily movements and provide information regarding movement frequencies and intensities, and can lead to better diagnosis of gait and postural instabilities and assessments of falls risk in the environment and situations in their own living environments.

Independent Variables: Patients will be evaluated in an "off" period (16 hours off of levodopa/carbidopa), and then in an "on" period (one hour after usual morning dose of levodopa/carbidopa).

In-Clinic Assessments: Dependent Variables:

Fall Evaluations:

Number and severity of falls including patient Diary.

MDS UPDRS:

MDS-UPDRS motor portion, Gait, FOG, and Pull test subtests (questions 3.9-3.14).

BNI Balance Subtests:

Turning 360 degrees, One Legged stance, and tandem gait. Patients will also be evaluated on their ability to walk 10 meters. Step-length and velocity will be determined by wearable sensors.

FOG Questionnaire:

FOG question 2.13 from MDS-UPDRS, and MDS-UPDRS motor subtest of FOG (3.11).

TUG test:

timed up & go test.

Question-1 from Orthostatic Hypotension Symptom Assessment

Apathy in Parkinson's Disease Questionnaire

UDysRS:

Unified Dyskinesia Rating Scale

Postural Stability:

Postural stability is paramount in contributing to safely performing activities of daily living. Indeed, deterioration in this control system is correlated with an increased risk of falls. In this study, outcome measures that define stability, and possibly fall risk, will include several linear measures such as sway area, center of pressure (COP) velocity, Antero-Posterior, Medio-Lateral sway range and several nonlinear measures such as approximate entropy and sample entropy. The postural stability measures will be performed in quiet standing, with standardized foot placement and the patients looking in the forward direction with arms at their sides. Two visual conditions will be performed: eyes-open (EO) and eyes-closed (EC). Each measurement will last for 30-60 seconds and will be repeated three times for each condition. A 3 minute rest will be provided between measurements.

Motor Control Time (MCT):

Utilizing the Neurocom system, we will assess motor control or reaction time to various postural perturbations. Postural stability can be defined as positional control of the whole body in space for purpose of balance and orientation. Postural orientation is an ability to maintain appropriate relationship between body and body segments and is dependent upon goals of movement task and the environmental context.

Human postural stability is governed by vestibular, visual, proprioceptive inputs, and integrated central processing. The background level of muscle tone activity changes in certain antigravity postural muscles to counteract the force of gravity. This increased activity in antigravity muscles is known as postural tone. Visual inputs and vestibular systems influence postural tone in various muscles while transition movement occurs (e.g., sit to stand).

Postural adjustments associated with movement, anticipatory postural adjustments (APAs), are preplanned by the central nervous system (CNS) and counteract the perturbation to postural stability during the movement. In otherwords, prior to voluntary limb movement, APAs maintain postural stability by compensating for destabilizing forces associated with moving a limb and thus prepare sensory and motor systems for postural demands based on previous learning. The CNS combines independent but related muscles into units called muscle synergies, which act together thus reducing the demand on the CNS. Although it is unknown how at higher levels the CNS manages APAs to optimize stability in movements, at lower level changes in postural strategies articulated by the postural demand of a task (stand-to-sit, sit-to-lay and other daily activities) can be quantified and investigated with the Neurocom Equitest. This measure is indicative of the final response of the neuromuscular system. Many researchers have related postural stability with understanding balance, motor control and gait problems in the elderly. Postural instability delay can lead to difficulty in maintaining balance upon a postural disturbance and may increase the risk of falls.

Gait and Posture Transition Assessments:

Patients will walk for a minute and, perform postural transition movements including dual tasking. Two factors of gait and postural stability that are relevant to balance control and dynamic stability during ambulation are: double-support time and walking speed indicative of gait adaptation to improve stability, and longer postural transition time indicative of pathology leading to increased falls. Additionally, an increase in the variability of one or both of these parameters may predispose people to fall, especially when balance mechanisms are stressed. Double support time and transitional aspects of postures over several walking cycles will be used to assess gait and mobility decrements. We will measure both walking speed and postural transitions as proxy for functional mobility status. Walking speed was chosen because it has been shown to be an independent predictor of falls leading to hospitalization. Postural transition parameter is important since movements from sit-to-stand and rising from a lying position are among the most common activities associated with daily life and the most mechanically demanding functional tasks in daily activities People with PD often fall during these transitions. Monitoring of postural transitions using the IMU will be used to assess fall risk. These transitions "slowness in getting out of a", "inability to rise from a chair of knee height without using the arms.".

In order to get away from traditional linear tools that may mask the true structure of motor variability, a non-linear dynamical analysis will also be applied to quantify stability differences and fall risks associated with the treatment conditions.

Dynamic stability was chosen to directly represent individuals' resistant to local perturbations and it has been shown to be an independent predictor of fall-prone adults. Thus using the IMU system, we can measure biomechanical variables that can assess individuals' fall risk characteristics with high accuracy and that are comparable to the motion capture laboratories. After the classification procedure, gait and mobility parameters such as the double support time and postural transition durations are calculated using the methods below.

To illustrate, Trunk Gyro-X (trunk angular velocity with flexion/extension) signals during standing, walking and various other postures during 7 minute activity is measured. A 3-seconds walking data from sternum TEMPO is denoised and, Heel Strike and Toe Off events are identified. Double support time is computed as the duration between heel strike by the contacting foot and toe-off by the contralateral foot. The trunk vertical accelerations will represent the whole body COM transitional acceleration occurring shortly after the heel strike event. Postural transition times will include initial flexion phase-t1, mid-transition phase-t2, and late extension phase-t3 (postural durations=sum of all phases). Walking speed will be calculated from 10 meter walkway using the IMU during the walking protocol.

At-Home Assessments (Three Consecutive Days): Dependent Variables

In this study, mobility characteristics associated with activity of daily living such as sitting down, lying down, rising up, and walking will be assessed. Additionally, characteristics of postural transitions such as sit-to-stand will be assessed at their own living environments utilizing an IMU. Furthermore, intensity of activities, energy expenditure, sleep quality/movements and fall frequencies will be recorded using an IMU system.

Physical Activity:

Being physically active is increasingly being acknowledged as a way to limit or prevent fall risks and disability. Objective and accurate information about the physical activities is a fundamental importance for our research. Prior to the event detection, IMU signal must be clearly represented and filtered to remove noises and artifacts from the signal. IMU signals are non-stationary and need denoising, and an efficient technique for non-stationary signal processing is the wavelet transform. The wavelet transform can be used as a decomposition of a signal in the time-frequency scale plane. Raw and denoised signals are measured. A robust algorithm to detect postural events occurring in daily life of an individual without any user-specified parameters will be deployed.

Walking Detection:

Moving window median will be used on denoised gyro-y and gyro-z and walking threshold will be established. Median windows helped in removing short postural transitions such as stand-to-sit, sit-to-stand, sit-to-lay, lay-to-sit etc. from the dynamic events such as walking Lay Down Detection:

Lay down event will be classified when detected dynamic events register acc-z greater than 0.5 g and acc-y less than 0.5 g. This threshold will be used as a major gravity component shifts from sensitive y-direction to sensitive z-direction of IMU when lying in supine posture.

Sit/Stand Event Detection:

Sit-to-stand events and stand-to-sit events will be classified as those dynamic events which were neither classified as walking nor as lying down. This will be done by replacing the data interval where walking and laying down events occur by calibration data points and using the static threshold in truncated acc-z and truncated gyro-x.

Figure 19:
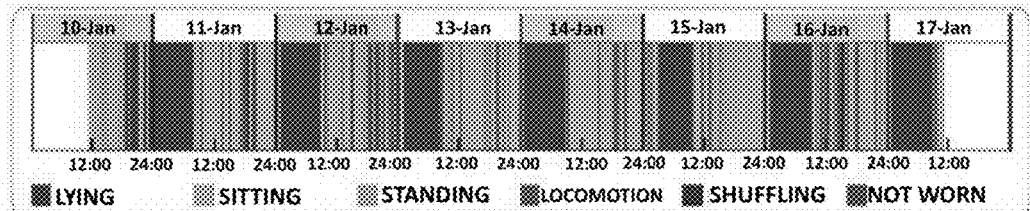
FIG. 19 illustrates activity of seven days including different types of physical activities.
Figure 20:
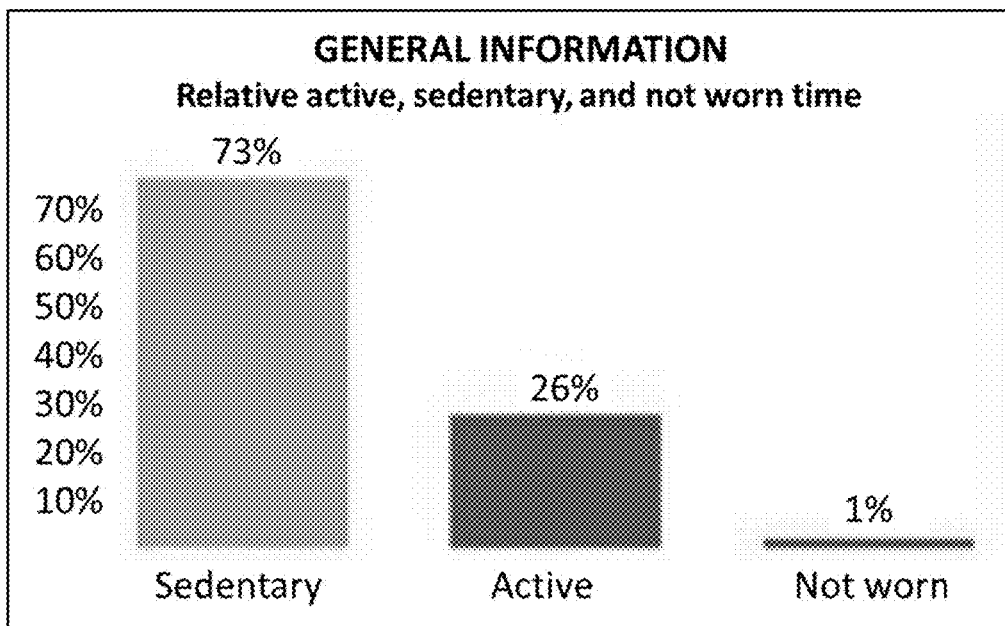
FIG. 20 illustrates sedentary and active movements during a seven day period.

Outcome Measures of Physical Activity:

Physical activities will be recorded for three consecutive days. Sedentary as well active components of movement throughout the day will be recorded (FIG. 19 and FIG. 20). FIG. 19 shows activity of seven days including different types of physical activities.

Energy Expenditure:

An Inertial Measurement Unit (IMU) will quantify energy expenditure (EE). The IMU consists of a tri-axial accelerometer. Data will be stored in the devices to allow data collection over a three day period and to capture data in a non-clinical environment—subjects can perform normal daily activities in their own environment. Subjects will be instructed how to operate and attach the device for measurement of daily physical activities. The device will be worn on the back (L5/S1), attached to a waistline belt, providing minute-by-minute acceleration in three orthogonal axes by which EE of physical activity (EEact) will be estimated. The output of the accelerations, and the subject's physical characteristics will be utilized to estimate this EEact (EEact=EE–Resting Energy Expenditure). Individual parameters are generalized for each subject—body mass, height, gender, and age—so that with the use of linear and nonlinear models and acceleration output, one can predict EE and subsequently, EEact (Chen et al., 1997). Subject's resting energy expenditure (REE) in kilocalories per minute (4.19 kJ/min) is determined by individual physical characteristics and predictive equations (1) and (2).

$$\text{Men:} \quad \frac{[473 \times \text{weight (lb)}] + [971 \times \text{height (in.)}] - [513 \times \text{age (yr)}] + 4687}{100,000} \quad (1)$$

$$\text{Women:} \quad \frac{[331 \times \text{weight (lb)}] + [352 \times \text{height (in.)}] - [353 \times \text{age (yr)}] + 49,584}{100,000} \quad (2)$$

Linear Model:

EEact (in kJ/min) is calculated based on the combined acceleration of all three directions (axes) $\sqrt{x^2+y^2+z^2}$. The V component consists of acceleration in the z-axis, isolated from the x- and y-axes. The rationale behind separating the axes is due to the fact that the z-axis is affected by gravity while the other dimensions are unburdened by this factor. The H component is defined as the square root of the sum of squared signals of the x- and y-axes $\sqrt{x^2+y^2}$. Both $a_L$ and $b_L$ represent regression parameters in the linear equation and k comprises time (i.e. EEact at the kth minute).

$$EEact(k) = a_L \times H(k) + b_L \times V(k) \quad (3)$$

Nonlinear Model:

In the nonlinear model, V and H signal were applied by the two power parameters (p1 and p2) to determine the nonlinear relationship between EEact and body acceleration. By comparing it with measured EEact, errors can be determined and used as the optimization factor. Please refer to the Chen et al. (1997) study for further information.

$$EEact(k) = a_N \times H(k)p1 + b_N \times V(k)p2 \quad (4)$$

Figure 21:
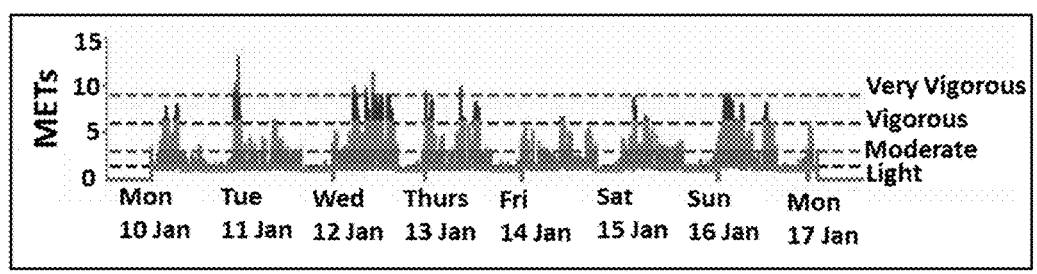
FIG. 21 illustrates activity levels associated with seven days including various activities such as light, moderate, vigorous, and very vigorous activities.

Finally, the energy expenditures will be categorized according to the METs levels (light, moderate, vigorous, and very vigorous) and, itemized activity levels across the day (FIG. 21). FIG. 21 shows activity levels associated with seven days including various activities such as light, moderate, vigorous and very vigorous activities.

Figure 22:
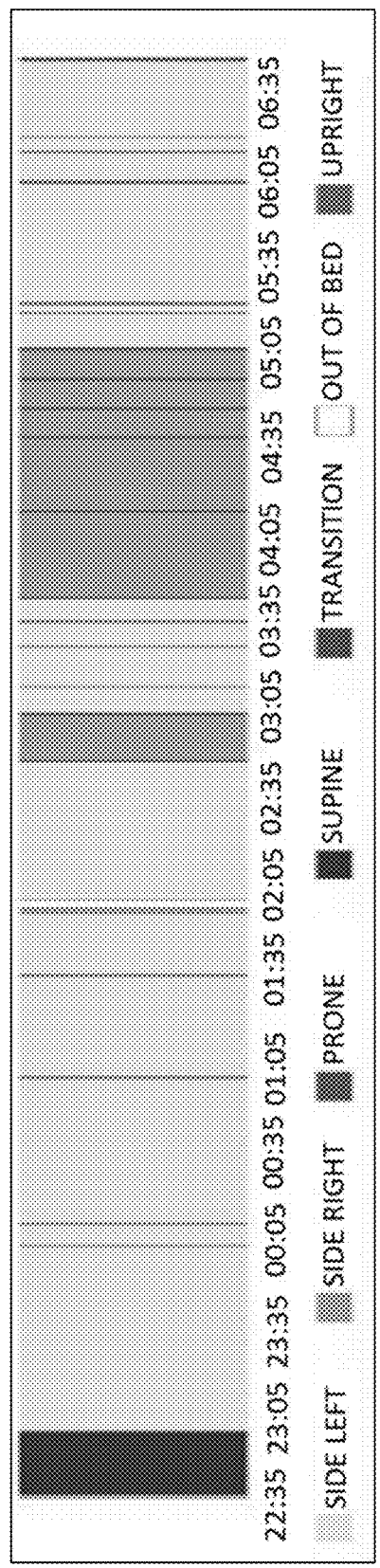
FIG. 22 illustrates various activities associated with sleep.

Sleep Movements:

Insufficient or poor quality sleep may result in drowsiness and loss of concentration that may increase fall risks. The sleep movement measures and classifies movement information related to night's rest. The movement intensity is used to identify transitions during night's rest. Of each transition the magnitude and average velocity are calculated, using the change of inclination of the trunk. Average movement intensity during movement time is calculated and is illustrated (FIG. 22). Night's rest detection, going out of the bed, and different postures during sleep will be quantified. FIG. 22 shows various activities associated with sleep.

Freezing of Gait (FOG):

For objective identification of FOG we are going to use the FOG index which was proposed by Moore et al., utilizing shank IMU. To define freezing of gait index, we will look for a large increase in the signal energy of leg movement in 3-8 Hz frequency band during FOG. We will use the power spectrum analysis over 6 s intervals of the vertical linear acceleration of the left shank. A FOG index at time t will be defined as the square of the area under the power spectra of a 6 s window of data (centered at time t) in the 'freeze' band, divided by the square of the area under the spectra in the locomotor band (0.5-3 Hz). For defining the threshold we will use the individual calibration Statistical Statement Estimation of required sample size using the MDS UPDRS scores proceeds from estimates of variability in significant effects associated with differentiating non-fallers and frequent fallers. Power calculations are performed here by focusing on sample sizes large enough to determine parameter differences between two groups with high probability. Utilizing the standard two-sided T-test: Power=P{|t*|>t(1−a/2; n−2)|d)} where d is the noncentrality parameter, or a measure of the distance between the means of A and B (13.4): d=|A−B|/s√(2/n) where s is the standard deviation of the distribution of MDS UPDRS scores (largest SD=12.6) and n is the number of subjects in each group. Specifying that a=0.05, 15 patients (in a crossover design), should be sufficient to detect the specified differences in gait and posture scores with risks of Type I error of 0.05 and Type II error of <0.20 (Power>0.80). Given the exclusionary criteria we will collect 20 participants' data.

Group Assignment:

A research assistant, who will not be involved in any assessments, will assign residents to the treatment or placebo groups. To further limit selection bias and affirm the groups are as identical as possible, we will employ an adaptive trial whereby stratification and randomization are defined after establishing the spread of baseline levels. Subjects will be assigned to one of two groups.

Compliance Assurance:

Several steps will ensure that the treatment procedure is followed. First, the supplementations will be distributed to subjects at each clinic visit and collected at subsequent clinic visit. Second, a form will be signed by the research assistant after each distribution and collection of the supplement. Third, the form will be inspected by the PI to monitor compliance. If not compliant, the participant will be given a choice to complete their trial and/or end the experimental protocols.

Data Processing and Statistical Considerations:

Primary outcome measure is pull-test and ability to stand on one-leg, and stability measures (defined by postural sway, motor control time, and dynamic stability). Secondary outcome measures are related to dependent variables of interest in determining fall risks.

The PI will monitor the results after every clinic visit using the participants' data to ensure technical success of testing. To avoid the problem of increased Type I error due to interim data analysis, a correction to the required p-values will be applied. For all statistical comparisons, transformations will be used for data that are not normally distributed, and non-parametric tests will be employed if extreme violations of normality are discovered. Transformations will be applied if the homogeneity of variances assumption is violated (Leven's test). Corrections for multiple follow-up comparisons will be done using Bonferroni correction.

Testing Specific Aim and Optimal Dosing:

A linear mixed effects models will be performed on all longitudinal measurements. Additionally, repeated measures ANOVA will also be performed (in case of no dropouts, and as an additional sensitivity analysis). The measurements associated with endpoint assessments will be used in the final model. Primary endpoints will base on the level of p<0.05 in any batteries of tests.

Benchmarks for Success:

The first three weeks of the trial will be devoted to assessing the baseline conditions and establishing rater reliability. Assessor training should be relatively straightforward because all outcome measures have been empirically verified and have well-developed methods/instructions and scoring systems, increasing the chance of high inter-rater reliability (Chohen's Kappa). The next six months will be spent assessing subject outcomes with interim analyses performed early in the trial to test treatment efficacy. To reach our target enrollment of 20 participants, we will examine our recruitment goals every week, and if our recruitment effort falls 10% below the required rate to reach our target enrollment, the research team will discuss about including additional facilities.

Adverse Event

During the treatment, caregivers will report on a questionnaire whether any problems or adverse events were encountered. At clinic visits, the research nurse will inquire about problems or adverse events. Additionally, blood pressure and heart rate will be monitored and documented prior to the testing. If an adverse event does occur, an adverse event form will be filled in which includes the description of the type of adverse event, the grade of the adverse event (e.g., mild/severe) and if the adverse event is related to the treatment. Each adverse event will be discussed with the PI, who will, with the consultation, determine whether the patient's supplementation should be halted or discontinued. If a serious adverse event occurs, a special serious adverse event form will be filed describing the event, the intensity, if a hospitalization was needed, the outcome of the event (e.g., recovered/ongoing), and the actions taken. If the serious adverse event is rated to be related to the supplementation, the PI and the IRB will determine whether the entire trial should be halted until further determination can be made about its safety.

What is claimed is:

1. A method of treating fall-related symptoms in a subject with neurodegenerative disease, the method comprises administering to the subject a dosage form comprising nicotine or salt thereof.

2. The method of claim 1, wherein the fall-related symptoms comprise fall frequency, frequency of injuries related to fall, or severity of fall with injuries.

3. The method of claim 2, wherein the subject treated with the dosage form comprising nicotine has a reduced fall frequency, reduced frequency of injuries related to fall, or reduced severity of fall with injuries.

4. The method of claim 1, wherein the subject has recurrent falls.

5. The method of claim 1, wherein the subject has fallen at least once in past year.

6. The method of claim 1, wherein improvement of symptoms comprises utilizing one or more of evaluation tests selected from the group consisting of: Unified Parkinson's Disease Rating Scale (UPDRS), Barrow Neurological Institute (BNI) Falls Evaluation, Hoehn & Yahr Staging System, Romberg test, turning test, standing on one leg, tandem gait, step length and velocity.

7. The method of claim 6, wherein the evaluation utilizing the Unified Parkinson's Disease Rating Scale (UPDRS) is selected from the group consisting of: Walking and Balance from questions 2.12 from Movement Disorder Society Unified Parkinson's Disease Rating Scale (MDS UPDRS), Freezing of Gait from questions 2.14 from Movement Disorder Society Unified Parkinson's Disease Rating Scale (MDS UPDRS), Dyskinesias from questions 32-35 from original Unified Parkinson's Disease Rating Scale (UPDRS), Response Fluctuation from questions 36-39 from original Unified Parkinson's Disease Rating Scale (UPDRS), Sleep Disturbance from question 40 from original Unified Parkinson's Disease Rating Scale (UPDRS), Movement Disorder Society Unified Parkinson's Disease Rating Scale (MDS UPDRS) 142 points, Axial, Midline part of Movement Disorder Society Unified Parkinson's Disease Rating Scale (MDS UPDRS), Gait Subtest from Movement Disorder Society Unified Parkinson's Disease Rating Scale (MDS UPDRS, Postural Stability Subtest from Movement Disorder Society Unified Parkinson's Disease Rating Scale (MDS UPDRS), and Freezing of Gait Subtest (FOG) from Movement Disorder Society Unified Parkinson's Disease Rating Scale (MDS UPDRS).

8. The method of claim 6, wherein the improvement of symptoms comprises evaluation utilizing Reason for Fall from the Barrow Neurological Institute (BNI) Falls Evaluation.

9. The method of claim 6, wherein the improvement of symptoms comprises evaluation utilizing Severity of Fall from the Barrow Neurological Institute (BNI) Falls Evaluation.

10. The method of claim 1, wherein the subject has Parkinson's disease.

11. The method of claim 1, wherein said dosage form is formulated for oral, intravenous, intraarterial, parenteral, buccal, topical, transdermal, rectal, intramuscular, subcutaneous, intraosseous, transmucosal, inhalation, or intraperitoneal administration.

12. The method of claim 1, wherein said dosage form is formulated for oral administration.

13. The method of claim 1, wherein said dosage form is formulated as a unit dosage.

14. The method of claim 13, wherein the unit dosage is a liquid, gel, semi-liquid, semi-solid, or solid form.

15. The method of claim 1, wherein said dosage form is formulated in a tablet or capsule.

16. The method of claim 13, wherein said unit dosage is formulated as a food, a beverage, or a dietary supplement.

17. The method of claim 1, wherein administration of said dosage form results in a pharmacokinetic profile having plasma nicotine levels below about 7.5 ng/ml at a time point about 120 minutes after administration of said dosage form.

18. The method of claim 1, wherein administration of said dosage form results in a pharmacokinetic profile having plasma nicotine levels below about 7.5 ng/ml at a time point about 180 minutes after administration of said dosage form.

19. The method of claim 18, wherein the pharmacokinetic profile has plasma nicotine levels below about 5 ng/ml at about 180 minutes after administration.

20. The method of claim 17, wherein the pharmacokinetic profile has plasma nicotine levels below about 5 ng/ml at about 120 minutes after administration.

* * * * *